(12) United States Patent
Lingappa et al.

(10) Patent No.: US 10,036,755 B2
(45) Date of Patent: Jul. 31, 2018

(54) MULTIPROTEIN ASSEMBLIES

(71) Applicant: Prosetta Antiviral, Inc., San Francisco, CA (US)

(72) Inventors: Vishwanath R. Lingappa, San Francisco, CA (US); Debendranath Dey, San Francisco, CA (US)

(73) Assignee: Prosetta Antiviral, Inc., San Francisco, CA (US)

( * ) Notice: Subject to any disclaimer, the term of this patent is extended or adjusted under 35 U.S.C. 154(b) by 98 days.

(21) Appl. No.: 14/677,819

(22) Filed: Apr. 2, 2015

(65) Prior Publication Data
US 2015/0226748 A1   Aug. 13, 2015

Related U.S. Application Data

(63) Continuation of application No. 13/457,481, filed on Apr. 26, 2012, now abandoned.

(60) Provisional application No. 61/479,351, filed on Apr. 26, 2011, provisional application No. 61/514,825, filed on Aug. 3, 2011.

(51) Int. Cl.
*C12N 7/00* (2006.01)
*G01N 33/68* (2006.01)
*C12P 21/02* (2006.01)

(52) U.S. Cl.
CPC .............. *G01N 33/68* (2013.01); *C12N 7/00* (2013.01); *C12P 21/02* (2013.01); *C12N 2740/16051* (2013.01); *C12N 2760/16151* (2013.01); *C12N 2770/24251* (2013.01); *C12N 2770/36151* (2013.01); *G01N 2333/065* (2013.01); *G01N 2500/02* (2013.01); *G01N 2500/20* (2013.01)

(58) Field of Classification Search
None
See application file for complete search history.

(56) References Cited

U.S. PATENT DOCUMENTS

| | | |
|---|---|---|
| 4,604,458 A | 8/1986 | Hung |
| 5,643,768 A | 7/1997 | Kawasaki |
| 6,593,103 B1 | 7/2003 | Lingappa et al. |
| 6,723,893 B1 | 4/2004 | Brown et al. |
| 6,765,088 B1 | 7/2004 | Carsten et al. |

(Continued)

FOREIGN PATENT DOCUMENTS

| | | |
|---|---|---|
| CN | 101092446 A | 12/2007 |
| DE | 196 40 758 | 4/1998 |

(Continued)

OTHER PUBLICATIONS

Klein et al. Unique Features of Hepatitis C Virus Capsid Formation Revealed by De Novo Cell-Free Assembly. Journal of Virology, Sep. 2004, p. 9257-9269.*

(Continued)

*Primary Examiner* — Michelle S Horning
(74) *Attorney, Agent, or Firm* — Morgan, Lewis & Bockius LLP

(57) ABSTRACT

The present invention provides compositions and methods of use in investigations of the formation of mulitprotein assemblies implicated in disease. Also provided are assays for screening candidate compounds of potential utility in preventing and/or treating such diseases by preventing the assembly of or disrupting the function of multiprotein assemblies.

13 Claims, 25 Drawing Sheets

(56) References Cited

U.S. PATENT DOCUMENTS

| | | |
|---|---|---|
| 6,821,742 B2 | 11/2004 | Lingappa et al. |
| 6,905,843 B1 | 6/2005 | Endo et al. |
| 7,041,462 B2 | 5/2006 | Lingappa et al. |
| 7,048,915 B2 | 5/2006 | Kuroita et al. |
| 7,074,595 B2 | 7/2006 | Endo et al. |
| 7,235,382 B2 | 6/2007 | Endo et al. |
| 7,273,615 B2 | 9/2007 | Endo et al. |
| 7,348,134 B2 | 3/2008 | Lingappa et al. |
| 7,407,948 B2 | 8/2008 | Griffiths et al. |
| 7,638,269 B2 | 12/2009 | Lingappa et al. |
| 7,674,593 B2 | 3/2010 | Endo et al. |
| 7,932,043 B2 | 4/2011 | Korth et al. |
| 8,734,856 B2 | 5/2014 | Endo |
| 2003/0022243 A1 | 1/2003 | Kondejewski et al. |
| 2003/0104577 A1 | 6/2003 | Lingappa et al. |
| 2003/0105152 A1 | 6/2003 | Ingram et al. |
| 2003/0158204 A1 | 8/2003 | Galey et al. |
| 2003/0162246 A1 | 8/2003 | Endo |
| 2006/0177813 A1 | 8/2006 | Endo |
| 2006/0264423 A1 | 11/2006 | Wood et al. |
| 2007/0087330 A1 | 4/2007 | Lingappa |
| 2007/0128633 A1 | 6/2007 | Zozulya et al. |
| 2008/0057523 A1 | 3/2008 | Sy et al. |
| 2010/0204215 A1 | 8/2010 | Galey et al. |
| 2010/0310461 A1 | 12/2010 | Sberg et al. |
| 2012/0301904 A1 | 11/2012 | Lingappa et al. |

FOREIGN PATENT DOCUMENTS

| | | |
|---|---|---|
| EP | 1 314 781 A1 | 6/2003 |
| EP | 1 316 617 A1 | 6/2003 |
| EP | 1 619 247 A1 | 11/2004 |
| GB | 2083488 | 3/1982 |
| JP | 2006-42601 A | 2/2006 |
| JP | 2006-136330 A | 6/2006 |
| KR | 10-2003-0031992 | 4/2003 |
| WO | WO 2002/018586 A1 | 3/2002 |
| WO | WO 2002/096896 | 12/2002 |
| WO | WO 2004/033628 | 4/2004 |
| WO | WO 2005/019828 | 3/2005 |
| WO | WO 2005/054217 | 6/2005 |
| WO | WO 2006/032847 | 3/2006 |
| WO | WO 2006/032879 | 3/2006 |
| WO | WO 2006/034219 | 3/2006 |
| WO | WO 2008/124550 | 10/2008 |

OTHER PUBLICATIONS

Fernández et al., "Targeted tandem affinity purification of PSD-95 recovers core postsynaptic complexes and schizophrenia susceptibility proteins" 5 Molecular Systems Biology Article 269, 1-19 (2009).

Kramer et al., "Selective detection, quantification, and subcellular localization of α-synuclein aggregates with a protein aggregate filtration assay", 44 BioTechniques 403-411 (2008).

Ambros, Ralf F., et al. "An Enzymatic Activity in Uninfected Cells That Cleaves the Linkage between Poliovirion RNA and the 5' Terminal Protein," Cell, vol. 15, Dec. 1978, pp. 1439-1446.

Bruening, George, et al. "In Vitro and in Vivo Translation of the Ribonucleic Acids of a Cowpea Strain of Tobacco Mosaic Virus," Virology 71, pp. 498-517 (1976), Department of Plant Pathology, Cornell Univ.

Benoît Van den Eynde, et al. "The Gene Coding for a Major Tumor Rejection Antigen of Tumor P815 Is Identical to the Normal Gene of Syngeneic DBA/2 Mice," J. Exp. Med. The Rockefeller Univ. Press, vol. 173, Jun. 1991, pp. 1373-1384.

Benoît Van den Eynde, et al. "A New Antigen Recognized by Cytolytic T Lymphocytes on a Human Kidney Tumor Results from Reverse Strand Transcription," J. Exp. Med. The Rockefeller Univ. Press, vol. 190, No. 12, Dec. 20, 1999, pp. 1793-1799.

Ann H. Erickson, et al. "Cell-Free Translation of Messenger RNA in a Wheat Germ System," Methods in Enzymology, vol. 96, pp. 38-50.

Molla et al in "Cell-Free, De Novo Synthesis of Poliovirus" (Science, Dec. 13, 1991, vol. 254, pp. 1647-1651).

Rozkovics Dissertation entitled A novel tyrosyl-RNA phosphodiesterase utilized by picornaviruses: Engineered substrates and biochemical analysis (first available Sep. 21, 2010).

C. Spencer Yost, et al. "A Stop Transfer Sequence Confers Predictable Transmembrane Orientation to a Previously Secreted Protein in Cell-Free Systems," Cell, vol. 34, pp. 759-766, Oct. 1983.

Tebbenkamp et al., "Protein Aggregate Characterization in Models of Neurodegenerative Disease" 566 Methods in Moleculate Biology 85-91 (2009).

U.S. Appl. No. 11/473,460, filed Jun. 22, 2006, U.S. Pat Pub No. 2007-0015211 (Jan. 18, 2007).

U.S. Appl. No. 11/567,142, filed Dec. 5, 2006, U.S. Pat Pub No. 2007-0202537 (Aug. 30, 2007).

U.S. Appl. No. 11/955,337, filed Dec. 12, 2007, U.S. Pat Pub No. 2009-0155761 (Jun. 18, 2009).

U.S. Appl. No. 12/062,491, filed Apr. 3, 2008, U.S. Pat. Pub. No. 20110178071 (Oct. 16, 2008).

U.S. Appl. No. 12/699,831, filed Feb. 3, 2010, U.S. Pat. Pub. No. 20100211327 (Aug. 19, 2010).

U.S. Appl. No. 13/099,006, filed May 2, 2011, U.S. Pat. Pub. No. 2012-0157435 (Jun. 21, 2012).

U.S. Appl. No. 13/316,423, filed Dec. 9, 2011.

U.S. Appl. No. 13/423,141, filed Mar. 16, 2012, U.S. Pat. Pub. No. 20120238543 (Sep. 20, 2012).

U.S. Appl. No. 13/433,378, filed Mar. 29, 2012, U.S. Pat. Pub. No. 20120302556 (Nov. 29, 2012).

U.S. Appl. No. 13/451,608, filed Apr. 20, 2012, U.S. Pat. Pub. No. 20120270854 (Oct. 25, 2012).

U.S. Appl. No. 13/566,897, filed Aug. 3, 2012, U.S. Pat. Pub. No. 2013-0053267 (Feb. 28, 2013).

U.S. Appl. No. 13/950,232, filed Jul. 24, 2013.

U.S. Appl. No. 61/760,599, filed Feb. 4, 2013.

U.S. Appl. No. 61/822,257, filed May 10, 2013.

U.S. Appl. No. 61/824,895, filed May 17, 2013.

U.S. Appl. No. 61/824,904, filed May 17, 2013.

Amaral et al. Phenothiazines: potential management of Creutzfeldt-Jacob disease and its variant, Int. Journal of Antimicrobial Agents 18 (2001) 411-0417.

Arhel et al., Host Proteins Involved in HIV Infection: New Therapeutic Targets, Biochimica et Biophysica Acta, vol. 1802: 313-321, 2010.

Baker-Wagner et al., "Evidence for Host Drug Targets Essential for Dengue Virus Capsid Formation", poster presented at the International Conference on Antiviral Research (ICAR) in San Francisco, CA, Apr. 25-Apr. 28, 2010.

Bewley, G.C., cDNA and deduced amino acid sequence of murine Cu—Zn superoxide dismutase, Nucleic Acids Research, vol. 16 No. 6 Mar. 25, 1988 (Mar. 25, 1988), p. 2728.

Bieniasz, P., Restriction Factors: a Defense Against Retroviral Infection, Trends in Microbiology, vol. 11: 286-291, 2003.

Coetzer et al., Erythrocyte Membrane Proteins in Hereditary Glucose Phosphate Isomerase Deficiency, J. Clinical Investigation 63 (4) : 552-561 (1979), abstract only.

Copeland et al., "Protein-Protein Interactions Occurring During HIV Capsid Assembly in a Cell-free Protein Synthesizing System", poster presented at the International Conference on Antiviral Research (ICAR) in San Francisco, CA, Apr. 25-Apr. 28, 2010.

Creighton T.E. Proteins, Structures and Molecular Properties, 2nd E. pp. 31-35.

Dooher et al., Cell-Free Systems for Capsid Assembly of Primate Lentiviruses from Three Different Lineages, The Journal of Medical Primatology, vol. 33: 272-280, 2004.

Francis et al., "Efficacy of a Small Molecule Inhibitor of Ebola Capsid Assembly in an Animal Model", poster presented at the International Conference on Antiviral Research (ICAR) in San Francisco, CA, Apr. 25-Apr. 28, 2010.

Haurum J.S., Recombinant polyclonal antibodies: the next generation of antibody therapeutics? Drug Discovery Today, 11(13/14), Jul. 2006.

(56) References Cited

OTHER PUBLICATIONS

Karpuj et al., "Small Molecule Therapeutics of Viruses of Families Bunyaviridae and Arenaviridae", poster presented at the International Conference on Antiviral Research (ICAR) in San Francisco, CA, Apr. 25-Apr. 28, 2010.

Khattab, M., Targeting Host Factors: a Novel Rationale for the Management of Hepatitis C Virus, World Journal of Gastroenterology, vol. 15: 3472-3479, 2009.

Klein et al., HIV Gag-leucine zipper chimeras form ABCE1-containing intermediates and RNase-resistant immature capsids similar to those formed by wild-type HIV-I Gag., The Journal of Virology, vol. 85:7419-35, 2011.

Klein et al., Identification of Residues in the Hepatitis C Virus Core Protein That Are Critical for Capsid Assembly in a Cell-Free System., Journal of Virology, vol. 79: 6814-6826, 2005.

Klein et al., Unique Features of Hepatitis C Virus Capsid Formation Revealed by De Novo Cell-Free Assembly., Journal of Virology, vol. 78: 9257-9269, 2004.

Komano et al., The Interaction of HIV-1 with the Host Factors., Japanese Journal of Infectious Diseases, vol. 58: 125-130, 2005.

Lawrason et al., Correlation between the mean corpuscular volume and reticulocytosis in phenlhydrazine anemia in swine, Blood 4: 1256-1263 (1949).

Lingappa et al., "Overlap in Virus Specificity Leads to the Discovery of Small Molecules Active Against Rabies Virus, Monkey Pox Virus and Cytomegalovirus", poster presented at the International Conference on Antiviral Research (ICAR) in San Francisco, CA, Apr. 25-Apr. 28, 2010.

Lingappa et al., "Cell-free Protein Synthesizing Systems as Tools for Discovery of Drugs Inhibiting Viral Capsid Assembly", poster presented at the International Conference on Antiviral Research (ICAR) in San Francisco, CA, Apr. 25-Apr. 28, 2010.

Lingappa et al., "Small Molecule Inhibitors of De Novo Cell-free Capsid Assembly Effective Against Flaviridae and Togaviridae", poster presented at the International Conference on Antiviral Research (ICAR) in San Francisco, CA, Apr. 25-Apr. 28, 2010.

Lingappa et al., A Eukaryotic Cytosolic Chaperonin Is Associated with a High Molecular Weight Intermediate in the Assembly of Hepatitis B Virus Capsid, a Multimeric Particle., The Journal of Cell Biology, vol. 125: 99-111, 1994.

Lingappa et al., A Multistep, ATP-Dependent Pathway for Assembly of Human Immunodeficiency Virus Capsids in a Cell-Free System., The Journal of Cell Biology, vol. 136: 567-581, 1997.

Lingappa et al., Comparing Capsid Assembly of Primate Lentiviruses and Hepatitis B Virus Using Cell-Free Systems., Virology, vol. 333: 114-123, 2005.

Lingappa et al., Recent Insights into Biological Regulation from Cell-Free Protein-Synthesizing Systems., The Mount Sinai Journal of Medicine, vol. 72: 141-160, 2005.

Long, Experimental Anemia Produced by Phenylhydrazine Derivatives, J. Clinical Investigation 11 (4) : 329-339 (1926).

Lumsden et al., The Kinetics of Hematopoiesis in the Light Horse III. The Hematological Response to Hemolytic Anemia, Can. J. Comp. Med. 39: 32-339 (Jul. 1975).

Mascarenhas et al., The Capsid Protein of Human Immunodeficiency Virus: Interactions of HIV-1 Capsid with Host Protein Factors, FEBS Journal, vol. 276: 6118-6127, 2009.

Palacios et al., Panmicrobial oligonucleotide array for diagnosis of infectious diseases, Emerging Infectious Diseases, vol. 13 No. 1, p. 73-81, Jan. 2007.

Papin et al., Methylene blue photoinactivation abolishes West Nile virus infectivity in vivo, Antiviral Research, Elsevier Science BV., Amsterdam, NL, vol. 68, No. 2, Nov. 1, 2005 (Nov. 1, 2005), pp. 84-87.

Pardo C A et al., Superoxide dismutase is an abundant component in cell bodies, dendrites, and axons of motor neurons and in a subset of other neurons, Proceedings of the National Academy of Sciences, vol. 92, No. 4, Feb. 14, 1995 (Feb. 14, 1995), pp. 954-958.

Petsch et al., "Discovery of Novel Small Molecule Inhibitors of Multiple Influenza-A Strains in Vivo", poster presented at the International Conference on Antiviral Research (ICAR) in San Francisco, CA, Apr. 25-Apr. 28, 2010.

Rakhit Rishi et al., "An immunological epitope selective for pathological monomer-misfolded SOD1 in ALS." Nature Medicine Jun. 2007, vol. 13, No. 6, pp. 754-759.

Rakhit Rishi et al., Monomeric Cu, Zn-superoxide dismutase is a common misfolding intermediate in the oxidation models of sporadic and familial amyotrophic lateral sclerosis, The Journal of Biological Chemistry Apr. 9, 2004, vol. 279, No. 15, pp. 15499-15504.

Ray Soumya S. et al: Small-molecule-mediated stabilization of familial amyotrophic lateral sclerosis-linked superoxide dismutase mutants against unfolding and aggregation, Proceedings of The National Academy of Sciences of the United States of America Mar. 8, 2005, vol. 102, No. 10, Mar. 8, 2005 (Mar. 8, 2005) pp. 3639-3644.

Reed et al., HIV-1 Gag co-opts a cellular complex containing DDX6, a helicase that facilitates capsid assembly, The Journal of Cell Biology, vol. 198(3):439-56, 2012.

Robuschi, L. Sperimentale (1940) 94, 99-124.

Rosenberg et al., Messenger RNA Loses the Ability to Direct in Vitro Peptide Synthesis following incubation with Cisplatin, Molecular Pharmacology 33 (6): 611-616 (1988).

Shapira et al., A Physical and Regulatory Map of Host-Influenza Interactions Reveals Pathways in H1N1 Infection, Cell, vol. 139: 1255-1267, 2009.

Sherman L. et al., Nucleotide Sequence and Expression of Human Chromosome 21-encoded superoxide Dismutase mRNA, Proceedings of the National Academy of Sciences, Washington, DC, US, vol. 80, Sep. 1983 (Sep. 1983), pp. 5465-5469.

Singh et al., Effect of Mutations in Gag on Assembly of Immature Human Immunodeficiency Virus Type 1 Capsids in a Cell-Free System., Virology, vol. 279: 257-270 (2001).

Stremlau, S., Why Old World Monkeys Are Resistant to HIV-1., Science, vol. 318: 1565-1566 (2007).

Stertz et al., Human host factors required for influenza virus replication, Nature, Feb. 11, 2010;463(7282):813-7.

Tai M M et al., Conformation specific antibodies directed against the Bovine Prothrombin Calcium Complex, Journal of Biological Chemistry, vol. 255, No. 7, pp. 2790-2795 (1980).

Visalli et al., DNA Encapsidation as a Target for Anti-Herpesvirus Drug Therapy., Antiviral Research, vol. 59: 73-87, (2003).

Voet et al. Biochemistry, 2nd. Ed. pp. 107-112.

Wainwright, Methylene blue derivatives—suitable photoantimicrobials for blood product disinfection? Review Article, International Journal of Antimicrobial Agents 16 (2000) 381-394.

Wang et al. Microarray-based detection and genotyping of viral pathogens, PNAS, vol. 99, No. 24, p. 15687-15692, Nov. 26, 2002.

Zimmerman et al., Identification of a Host Protein Essential for Assembly of Immature HIV-1 Capsids, Nature, vol. 415: 88-92 (2002).

* cited by examiner

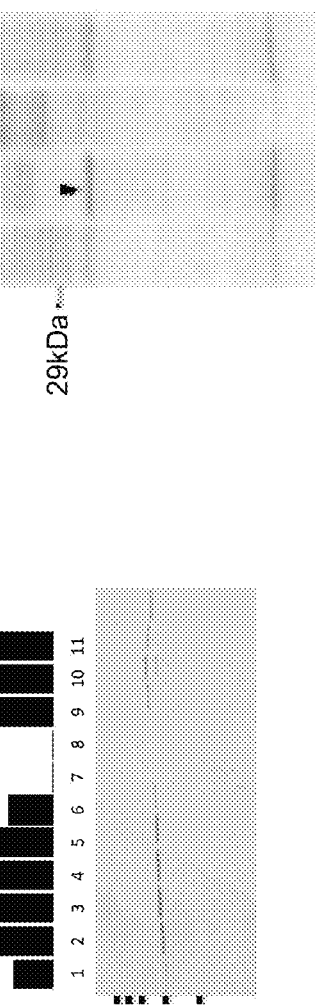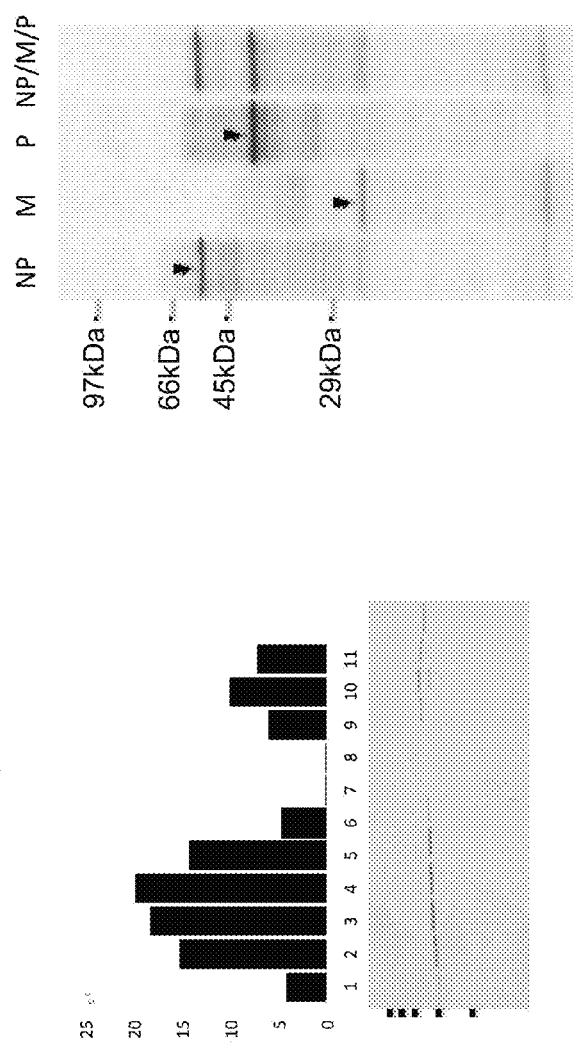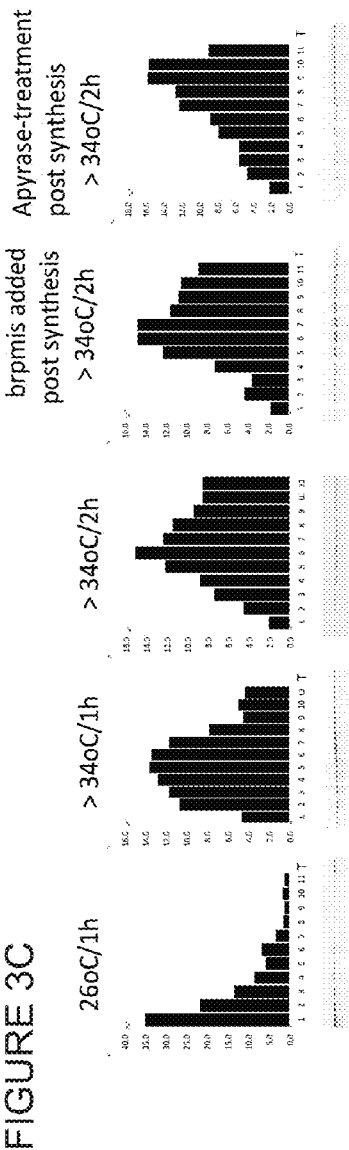
FIGURE 3A
FIGURE 3B
FIGURE 3C

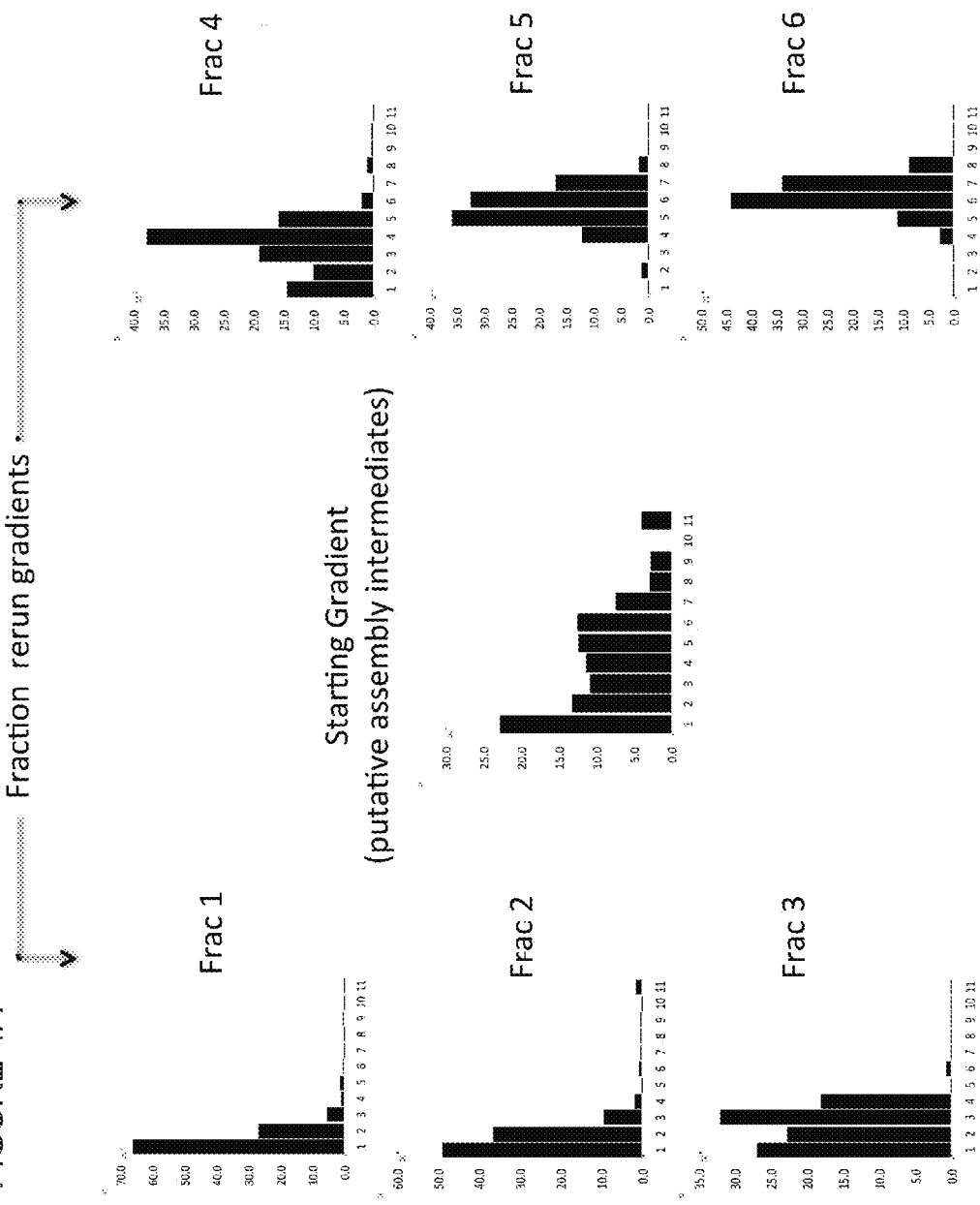

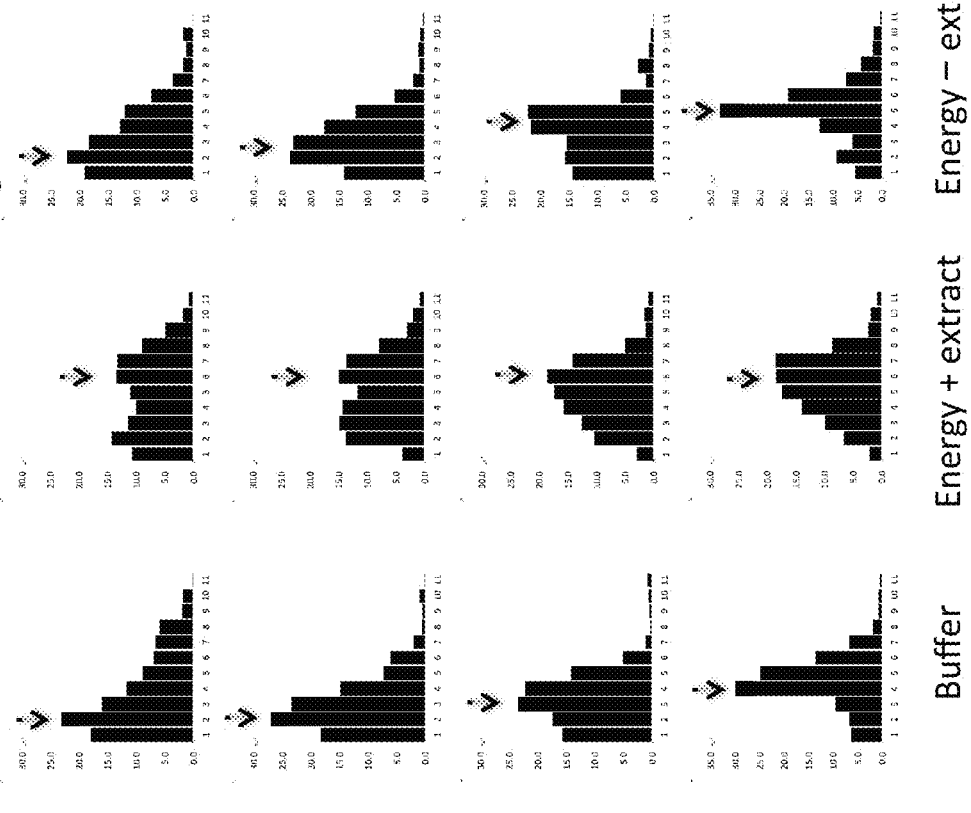

Figure 10 RABV NP mRNA lacking a termination codon expressed in the cell-free system allows stepwise dissection of the earliest steps of the putative capsid assembly pathway 10A — Puromycin B + Puromycin C + Puromycin > 34°C/2h Figure 11 Post-translational assessment of mechanism of action of A in the cell-free plate screen.
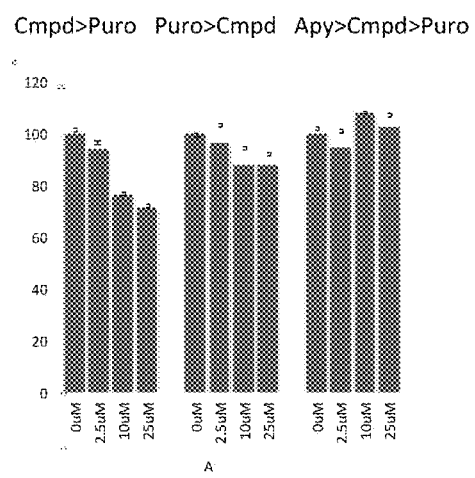

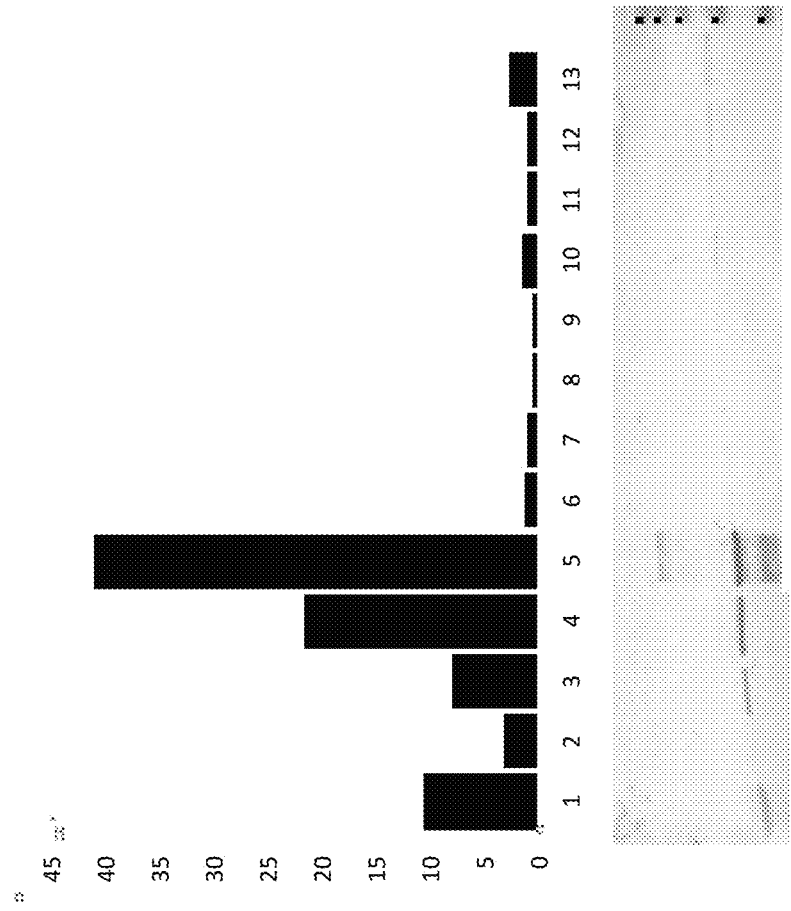

WB of WG extract column 1 A eluates for ABCE1

WB of brpmis column 1 A eluates for ABCE1

Figure 16 Model for RABV capsid assembly and point of action of PAV-866

Figure 17

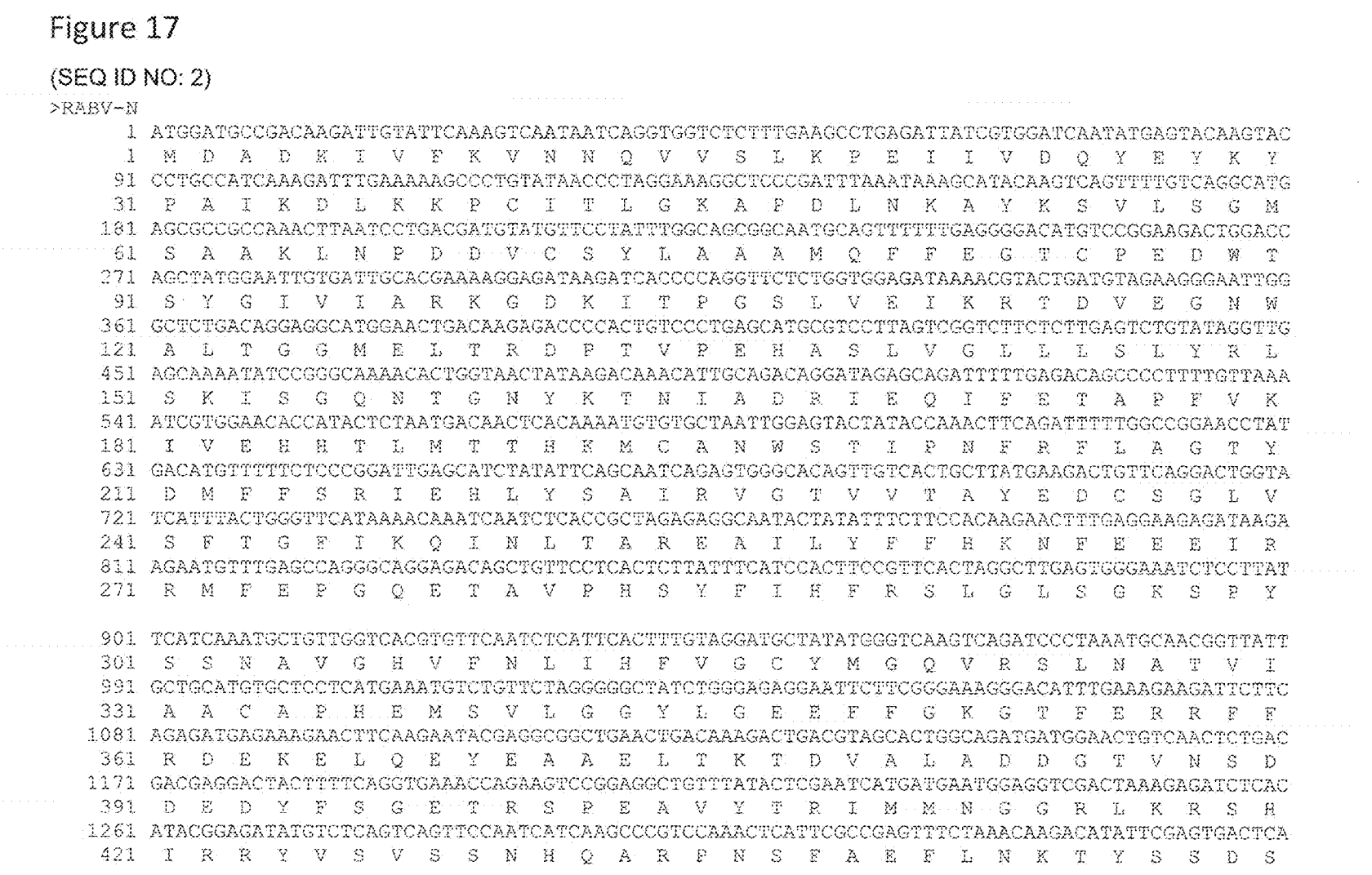

(SEQ ID NO: 2)

>RABV-N

```
   1 ATGGATGCCGACAAGATTGTATTCAAAGTCAATAATCAGGTGGTCTCTTTGAAGCCTGAGATTATCGTGGATCAATATGAGTACAAGTAC
   1  M  D  A  D  K  I  V  F  K  V  N  N  Q  V  V  S  L  K  P  E  I  I  V  D  Q  Y  E  Y  K  Y
  91 CCTGCCATCAAAGATTTGAAAAAGCCCTGTATAACCCTGAAAGCATACAAGTCAGTTTTGTCAGGCATG
  31  P  A  I  K  D  L  K  K  P  C  I  T  L  G  K  A  P  D  L  N  K  A  Y  K  S  V  L  S  G  M
 181 AGCGCCGCCAAACTTAATCCTGAC

Figure 18

Sequence of RABV N mRNA WITHOUT STOP CODON: (SEQ ID NO: 3)

```
   1 AUGGAUGCCGACAAGAUUGUAUUCAAAGUCAAUAAUCAGGUGGUCUCUUUGAAGCCUGAGAUUAUCGUGGAUCAAUAUGAGUACAAGUAC
 1 M  D  A  D  K  I  V  F  K  V  N  N  Q  V  V  S  L  K  P  E  I  I  V  D  Q  Y  E  Y  K  Y
  91 CCUGCCAUCAAAGAUUUGAAAAAGCCCUGUAUAACCCUAGGAAAGGCUUCCGAUUAAAUAAGGCAUACAAGUCAGUUUGUCAGGCAUG
31 P  A  I  K  D  L  K  K  P  C  I  T  L  G  K  A  P  D  L  N  K  A  Y  K  S  V  L  S  G  M
 181 AGCCCGGCCAAACUAAUCCUGACGAUGGAUGUCCUAUUGGCAGCGGCAAUGCCAGUUUUUGAGGGACAUGUCCGAAGACUGGACC
61 S  A  A  K  L  N  P  D  D  V  C  S  Y  L  A  A  M  Q  F  P  E  G  T  C  P  E  D  W  T
 271 AGCUAUGGAAUGUGACACGCAGAAAAGGACAAGAUCAUCACCCCAGGUUCCUGUGGAGAUAAAACGUACGAUGUAGAAGGGAAUUGG
91 S  Y  G  I  V  I  A  R  K  G  D  K  I  T  P  G  S  L  V  E  I  K  R  T  D  V  E  G  N  W
 361 GCUCUGACAGGAGGCAUGGAACUGACAAGAGACCCCACUGUCCUAGCCAUGGGACUCCUGAGCUCUGUAUAGGUUG
121 A  L  T  G  G  M  E  L  T  R  D  P  T  V  P  E  H  A  S  L  V  G  L  L  S  L  Y  R  L
 451 AGCAAAAAUCCGGCAAAACUGGUAACUGGUAACACUGGUAACAUUGCAGACAGGACAGAUUUUGAGACAGCCCUUUGUAAA
151 S  K  I  S  G  Q  N  T  G  N  Y  K  T  N  I  A  D  R  I  E  Q  I  F  E  T  A  P  F  V  K
 541 AUGUGGAACACCAUACUCAACAACUCACAAAAUGUGUGCUAAAUGGAGUACAGUUCAGAUUUCAGAUUUUGGCCGGAACCUAU
181 I  V  E  H  H  T  L  M  T  T  H  K  M  C  A  N  W  S  T  I  P  N  F  R  F  L  A  G  T  Y
 631 GACAAUGUUUUUCUCCCGGAUUGAGCAAUCAGAGAGUGCACAGUUGUCACUGCCUAUGAAGAGACAGUUCAGGACUGGUA
211 D  M  F  F  S  R  I  E  H  L  Y  S  A  I  R  V  G  T  V  V  T  A  Y  E  D  C  S  G  L  V
 721 UCAUUUACUGGGUCAUAAAACAAAUCUCACCGCCUAGAGAGGCAAUACACCCUUAGCAAGAACUUCUUCCACAAGAACUUUGAGGAAGAUAAGA
241 S  F  T  G  F  I  K  Q  I  N  L  T  A  R  B  A  I  L  Y  F  F  H  K  N  F  E  E  I  R
 811 AGAAUGUUUGAGCCCAGGCAGGAACAGCGCUUCCUCACUGAUCUGGCUACUCACUUCCGUUCACUUAGGCCUUGAGUGGAAAUCCCUUAU
271 R  M  F  E  P  G  Q  E  T  A  V  P  H  S  Y  P  I  H  P  R  S  L  G  L  S  G  K  S  P  Y
 901 UCAUCAAUGGCUGUUGGUCACGUGGUCAAUCUGCAUUCACUUUGUAGGAUGCUAUGGGUCAAGCCAGAUCCUAAAUGCAACGGUUAUU
301 S  S  N  A  V  G  H  V  F  N  L  I  H  F  V  G  C  Y  M  G  Q  V  R  S  L  N  A  T  V  I
 991 GCUCAUGGUGCUCCUCAUGAAUUCAAGAGAAUACGAGGCGGUCUGAACUGACAAAGACAAGACACUGGCAGAUGAUGGAACGUCAACUGAC
331 A  C  A  P  H  E  M  S  V  L  G  G  Y  L  G  E  F  F  G  K  G  T  F  E  R  R  F  F
1081 AGAGAUGAGAAGAACUUCCAGAGGAAGACUGUUGACAGGUCAGGCUGAAGCUUGGAGAUCUGAAGGCUUCGGGAACAUGACUGAC
361 R  D  E  K  E  L  Q  E  Y  E  A  A  E  L  T  K  T  D  V  A  L  A  D  D  G  T  V  N  S  D
1171 GACGAAGGACUACUUUCAGGGAAAACCAGAAGUCCGGAGGCCUGACUUUAAAUCUGGAAAAUGGAGUCGACUAAAGAGAUCUCAC
391 D  E  D  Y  F  S  G  E  T  R  S  P  E  A  V  Y  T  R  I  M  M  N  G  G  R  L  K  R  S  H
1261 AUACGGAGAUAUGUCGUCAGUGUAAGGCCCAAACAUCAAGCCCGUCCAAUUCCAGUUCUUCAAACAAGACAUAUCGAGUGACUCA
421 I  R  R  Y  V  V  S  V  S  S  N  H  Q  A  R  F  N  S  F  A  E  F  L  N  K  T  Y  S  S  D  S
```

Figure 19

SEQUENCE OF RABV-N mRNA WITH stop codon: (SEQ ID NO: 4)

AUGGAUGCCGACAAGAUUGUAUUCAAAGUCAAUAAUCAGGUGGUCUCUUUGAAGCCUGAGAUUAUCGUGGAUCAAUAUGAGUACAAGUACCCUGCCAU
CAAAGAUUUGAAAAAGCCCUGUAUAACCCUAGGAAAGGCUCCCGAUUUAAAUAAAGCAUACAAGUCAGUUUUGUCAGGCAUGAGCGCCGCCAAACUUA
AUCCUGACGAUGUAUGUUCCUAUUUGGCAGCGGCAAUGCAGUUUUUUGAGGGGACAUGUCCGGAAGACUGGACCAGCUAUGGAAUUGUGAUUGCACGA
AAAGGAGAUAAGAUCACCCCAGGUUCUCUGGUGGAGAUAAAACGUACUGAUGUAGAAGGGAAUUGGGCUCUGACAGGAGGCAUGGAACUGACAAGAGA
CCCCACUGUCCCUGAGCAUGCGUCCUUAGUCGGUCUUCUCUUGAGUCUGUAUAGGUUGAGCAAAAUAUCCGGGCAAAACACUGGUAACUAUAAGACAA
ACAUUGCAGACAGGAUAGAGCAGAUUUUUGAGACAGCCCCUUUUGUUAAAAUCGUGGAACACCAUACUCUAAUGACAACUCACAAAAUGUGUGCUAAU
UGGAGUACUAUACCAAACUUCAGAUUUUUGGCCGGAACCUAUGACAUGUUUUUCUCCCGGAUUGAGCAUCUAUAUUCAGCAAUCAGAGUGGGCACAGU
UGUCACUGCUUAUGAAGACUGUUCAGGACUGGUAUCAUUUACUGGGUUCAUAAAACAAAUCAAUCUCACCGCUAGAGAGGCAAUACUAUAUUUCUUCC
ACAAGAACUUUGAGGAAGAGAUAAGAAGAAUGUUUGAGCCAGGGCAGGAGACAGCUGUUCCUCACUCUUAUUUCAUCCACUUCCGUUCACUAGGCUUG
AGUGGGAAAUCUCCUUAUUCAUCAAAUGCUGUUGGUCACGUGUUCAAUCUCAUUCACUUUGUAGGAUGCUAUAUGGGUCAAGUCAGAUCCCUAAAUGC
AACGGUUAUUGCUGCAUGUGCUCCUCAUGAAAUGUCUGUUCUAGGGGGCUAUCUGGGAGAGGAAUUCUUCGGGAAAGGGACAUUUGAAAGAAGAUUCU
UCAGAGAUGAGAAAGAACUUCAAGAAUACGAGGCGGCUGAACUGACAAAGACUGACGUAGCACUGGCAGAUGAUGGAACUGUCAACUCUGACGACGAG
GACUACUUUUCAGGUGAAACCAGAAGUCCGGAGGCUGUUUAUACUCGAAUCAUGAUGAAUGGAGGUCGACUAAAGAGAUCUCACAUACGGAGAUAUGU
CUCAGUCAGUUCCAAUCAUCAAGCCCGUCCAAACUCAUUCGCCGAGUUUCUAAACAAGACAUAUUCGAGUGACUCAUAA

Figure 19a

Name: Rabies_NP-STOP (SEQ ID NO: 5)
Sequences of oligos used used to make the stop minus construct:

5'TGAGTCACTCGAATATGTC

Figure 19b

Name: pTnT-F1 (SEQ ID NO: 6)
Upstream of the SP6 promoter sequence in pTnT:

5'GGCTCGACAGATCTTAAGGCT

MULTIPROTEIN ASSEMBLIES

CROSS-REFERENCE TO RELATED APPLICATIONS

The present application is a continuation of U.S. patent application Ser. No. 13/457,481, filed Apr. 26, 2012, which claims benefit under 35 U.S.C. § 119(e) to U.S. Provisional Patent Application No. 61/479,351, filed Apr. 26, 2011 and U.S. Provisional Patent Application No. 61/514,825, filed Aug. 3, 2011, all entirely incorporated herein by reference for all purposes.

FIELD OF THE INVENTION

The instant invention relates generally to the field of chemotherapeutics and assays for determining whether a candidate chemotherapeutic is useful in preventing, curing or retarding the advancement of a disease. More particularly, this invention relates to compositions and methods for the identifying novel chemotherapeutics effective against viral infections. Still further, the present invention relates to screening assays using a protein-ribosome complex for the screening and identification of novel chemotherapeutics.

BACKGROUND OF THE INVENTION

Protein synthesis is carried out by an elaborate translation complex, which is composed of a ribosome, accessory protein factors as well as mRNA and charged tRNA molecules. Like DNA and RNA synthesis, protein synthesis can be divided into initiation, chain elongation and termination stages. Initiation involves the assembly of the translation complex at the start codon in the mRNA. During polypeptide-chain elongation, the ribosome and associated components move in the 5' to 3' direction along the template mRNA. The polypeptide is synthesized from the N-terminus to the C-terminus. Finally, when synthesis of the protein is complete, the translation complex disassembles in a separate termination step. An important part of this disassembly is the release of the ribosome from the mRNA, which is signaled by a stop codon.

Catalysis of peptide bond formation requires the precise juxtaposition by the ribosome of the acceptor ends of the amino acid-charged tRNA's bound in the peptidyl site (i.e., P site) and aminoacyl site (i.e., A site) of its "active site". This activity represents the essential enzymatic activity of the ribosome and is referred to as the "peptidyl transferase activity," an integral component of the large subunit of all ribosomes characterized to date. Studies of bacterial ribosomes have identified the essential active site constituents of the peptidyl transferase activity as a few ribosomal protein subunits and the 23S rRNA. As the integrity of the latter is essential for enzymatic activity, it is assumed that it plays a direct role in the catalysis of peptide bond formation acting as a so-called ribozyme.

Many diseases involve foreign or aberrant host proteins, for example, viral infections involve the synthesis of viral proteins, e.g., capsid proteins. A variety of agents are presently used to combat viral infection. These agents include interferon, which is a naturally-occurring protein having some efficacy in combat of certain selected viral diseases. In addition, agents such as AZT are used in the combat of an immunodeficiency disease, referred to commonly as AIDS, caused by the virus HIV-1.

Given the large number of drugs available for treating infections caused by more complex organisms such as bacteria, it is remarkable how few drugs are available for treating the relatively simple organisms known as viruses. Indeed, most viral diseases remain essentially untreatable. The development of new antiviral chemotherapeutics is resource- and time-intensive. The difficulties encountered in drug treatment of most infections pale when compared to viral infections. For example, it is at least theoretically (and often in practice) possible to attack a bacterium without harming the host. Unlike bacteria however, viruses replicate inside cells and utilize cellular machinery of the host for replication. As a result, development of antiviral therapeutics often represents a compromise between preferable killing, or at least arresting replication of, the virus, and not harming the host, or at worst, doing only minimal damage which can be justified by the potential gain (Drug and Market Development, Vol 3. No. 9, pp. 174-180 (Feb. 15, 1993)).

It is now generally recognized that an important challenge for small molecule drug discovery is the identification of novel druggable targets (Hopkins A-L, Groom C-R (2002) The druggable genome. *Nat Rev Drug Discov.* 1:727-730). Conventional targets appear to have largely been exhausted, and it can be argued that various highly anticipated methods in recent years have disappointed, in that many of the targets they are identifying are of questionable druggability (Goff S-P (2008) Knockdown screens to knockout HIV-1. *Cell* 135:417-420). How then does one find the likely highly unconventional novel druggable targets of the future?

SUMMARY OF THE INVENTION

The present invention provides an approach orthogonal to conventional drug discovery. The method provides compositions and methods for investigating host-viral protein-protein interactions occurring during protein biogenesis and maturation, as a novel starting point for identification of therapeutic small molecules. These protein-protein interactions are critical for the later function of proteins and, counter-intuitively, subtle disruption of a subset of these early interactions is sufficient to functionally impact later events in assembly of proteins, in a substrate selective manner.

The compositions and methods of the invention allow the identification of small molecule therapeutics that function in a novel manner, targeting host proteins that appear to comprise highly unconventional drug targets. Remarkably, these host-targeted compounds have robust efficacy against proteins implicated in disease states (e.g., viral capsid proteins) at concentrations avoiding significant toxicity to cultured mammalian cells. Moreover, these compounds display improved in selectivity indices (toxicity/efficacy) with structure-activity relationship (SAR) optimization. The present invention provides a new approach to therapeutic agents that function by disrupting protein-protein interactions generally, and those implicated in viral diseases in particular.

In an exemplary embodiment, the invention provides a complex between a messenger RNA (m-RNA) sequence and a ribosome. In various embodiments, the m-RNA is a truncated m-RNA, truncated in the sense that it does not include a stop codon at its 3'-terminus. In an exemplary embodiment, the truncated m-RNA is complexed to the P-site of the ribosome. In various embodiments, the A-site of the ribosome is essentially free of complexed truncated m-RNA.

In an exemplary embodiment, the invention provides a method of assaying a candidate compound for its ability to disrupt the assembling proteins (e.g., non-viral proteins) in a multiprotein assembly or the function of a complete assembly. In selected embodiments, the multiprotein assembly is implicated in the origin or advancement of one or more disease, e.g., viral infections, bacterial infections, central nervous system disorders, metabolic disorders, oncologic disorders, or immunologic disorders. In an exemplary embodiment, the methods assemble a multiprotein assembly of bacterial or parasitic proteins which is a novel target for drug development.

In various embodiments, there is provided a method of testing whether a candidate compound modulates the assembly of or function of a multiprotein assembly. An exemplary method includes introducing the compound to a cell-free system of the invention expressing a component of the multiprotein assembly of interest, and determining whether the assembly or function is modulated.

The invention also provides a method of testing whether a compound modulates viral capsid assembly due to an effect on host proteins or on the viral capsid proteins themselves. The method includes introducing the compound to a cell-free system of the invention and determining whether the viral capsid (or other protein) assembly is modulated.

These and additional objects, advantages and embodiments of the invention are described in the detailed description that follows.

BRIEF DESCRIPTION OF THE DRAWINGS

FIG. 2A shows a tRNA molecule 800 carrying an amino acid 802 binds to a vacant A-site 820, while the growing polypeptide chain 810 is attached to amino acid 806 on tRNA 804 that is docked in the P-site 822. At this stage E site 824 is shown as empty. FIG. 2B shows a new peptide bond created between amino acid 806 and amino acid 802, and the polypeptide chain 810 is moved to the A-site 820. FIG. 2C shows the ribosome translocating 3 nucleotides with respect to the mRNA, the two tRNA units 800 and 804, and the polypeptide chain 810.

FIG. 3A-FIG. 3D. Cell-free expression and assembly of RABV N and P containing protein complexes. A. Reference analysis of authentic RABV nucleoprotein on sucrose step gradients (ssg) followed by Western blotting (WB). Authentic RABV, irradiated and demonstrated to be no longer infectious was received from the Centers for Disease Control and Prevention, treated with TRITON™ x-100 (detergent, TRITON is a trademark of Dow Chemical Company) to 1% and 40 μl diluted to 100 μl in physiological salts and applied to ssg for 55 minutes at 50,000 rpm in the TLS-55 rotor with ultraclear tubes and a 2 ml gradient volume. Gradients were formed by layering over 200 μl of 85% sucrose 300 μl of 50%, 40%, 30%, 20%, 10% and 5% sucrose all in 1× salts with 0.2% TRITON™ x-100 (detergent, TRITON is a trademark of Dow Chemical Company).

Figure 1A:
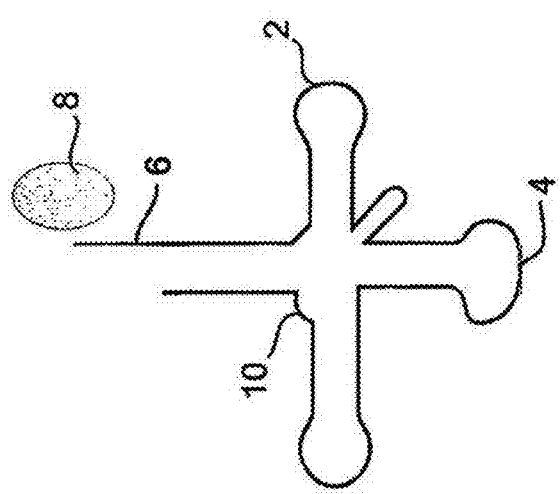
FIG. 1A describes the tRNA molecule 2 with the anticodon loop 4, the amino acid arm 6, the shoulder 10, and a loaded amino acid 8.

200 μl fractions were taken from the top and an aliquot prepared for SDS-PAGE and the gel transferred to 0.2μ PVDF membrane overnight at 40 volts, blocked in 1% bovine serum albumin (BSA) and phosphate buffered saline with 0.1% TWEEN™-20 (PBST) (detergent, TWEEN is a trademark of Croda International) for 1 hr and probed with affinity purified anti-RABV N antibody 0.5 mg/ml at a dilution of 1:1000 in 1% BSA with PBS-T for 1 hr followed by 3 washes for 10 minutes each. Secondary anti-rabbit antibody conjugated to alkaline phosphatase from Jackson Labs was used at 1:5000 dilution for 1 hr and the same washing steps. After a final Tris buffered saline wash blots were developed with BCIP-NBT solution. B. Cell-free protein synthesis was carried out in the presence of S35 Methionine, essentially as described previously (Bose S, Mathur M, Bates P, Joshi N, Banerjee A-K (2003) Requirement for cyclophilin A for the replication of vesicular stomatitis virus New Jersey serotype. *J Gen Virol* 84:1687-1699). 1 μl of translation product was applied to SDS-PAGE and the dried gel exposed to film for autoradiographic imagining of the presence of radiolabelled translation products. As seen, major bands were observed corresponding to the expected sizes of proteins encoded by the N, M and P genes of RABV individually and when all three mRNAs were combined at a ratio of 2:4:1 (N:M:P). C. RABV N was synthesized in the cfps system similar to previously (Nagy P-D, Pogany J (2011) The dependence of viral RNA replication on co-opted host factors. *Nat Rev Microbiol* 10:137-149). After synthesis at 26° C./1 hr, products were treated with puromycin to 1 mM and incubated at 34° C. for 1 or 2 hrs as indicated without or with supplementation of rbrpmis (4th panel from left) or apyrase (right most panel). After incubation, samples were transferred to ice and loaded onto sucrose step gradients, centrifuged in TL100 table top ultracentrifuge in the TLS-55 rotor at 50 k rpm for 55 minutes, 200 μl fractions collected and aliquots analyzed by SDS PAGE and the RABV N specific band quantified by densitometry using image J software. D. As previously but with expression of N, P, and M genes together. Note the slowing of N progression through the putative assembly pathway in the presence of newly synthesized M and P. Autoradiograms from which quantified bands were determined are shown below the plots for 3C and 3D.

FIGS. 4A-FIGS. 4D. A. Identification of putative assembly intermediates involving RABV N. Ssg fractions analogous to that described in the FIG. 3D extreme right hand panel were taken as the starting point for analysis. Individual fractions 1-6 were diluted with physiological salts (Hepes or Tris 50 mM pH 7.6, potassium acetate 100 mM, magnesium acetate 5 mM) in 0.2% TRITON™ x-100 (detergent, TRITON is a trademark of Dow Chemical Company) to decrease the sucrose concentration below 5% and 200 ul loaded onto standard ssg as described for FIG. 3. Centrifugation and analysis were as described for FIG. 3. The center panel shows the initial ssg profile from which individual fractions were rerun as described. Profile of each fraction upon rerun is indicated to the left or right. B-D. Individual fractions shown in A were incubated with either physiological salts (buffer), or translation master mix in the absence of radiolabel with (C) or without (D) WG extract and incubated at 34° C./2 h and then analyzed on ssg.

Figure 5:
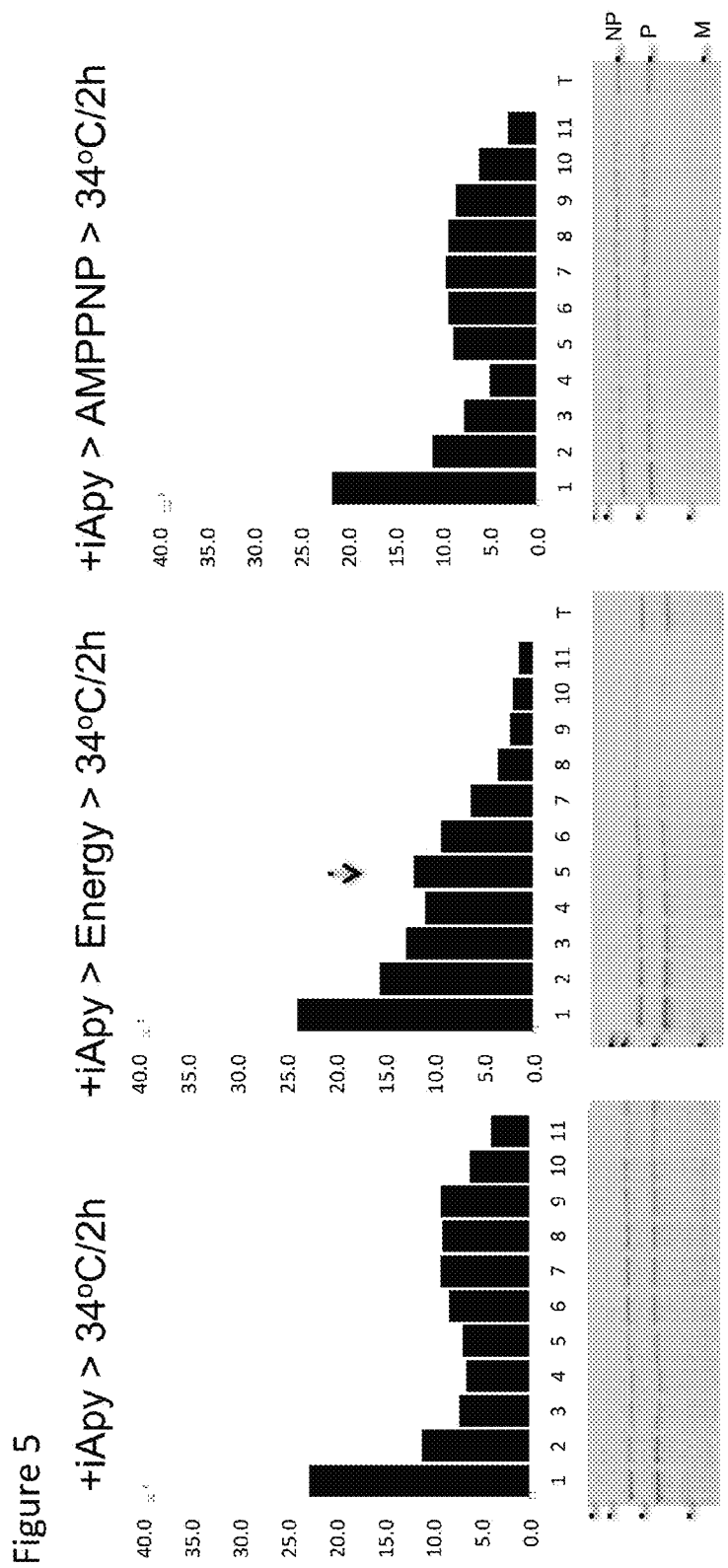

FIG. 5. Energy-dependence of RABV N assembly to material peaking in fractions 5-7. RABV N, M, and P were expressed at 22° C./1 h, generating material that on ssg is largely in fractions 1 and 2 (see FIG. 3D left panel). This material was incubated with sepharose-immobilized apyrase at 4° C./1 h to hydrolyze the ATP. Then the sepharose was removed and the sample incubated at 34° C./2 h either with no addition (left panel), with 1 mM ATP, GTP and an energy regenerating system (creatine kinase and creatine phosphate) added (middle panel) or with 1 mM non-hydrolyzable ATP analog AMPPNP added (right panel). At the end of the incubation samples were analyzed by standard ssg as previously described. Progression through the putative RABV capsid assembly pathway is energy-dependent and the energy-dependent pathway culminates in the complex peaking in fraction 5 (see arrow in middle panel). Autoradiograms from which quantified bands were determined are shown below the plots.

Figure 6:
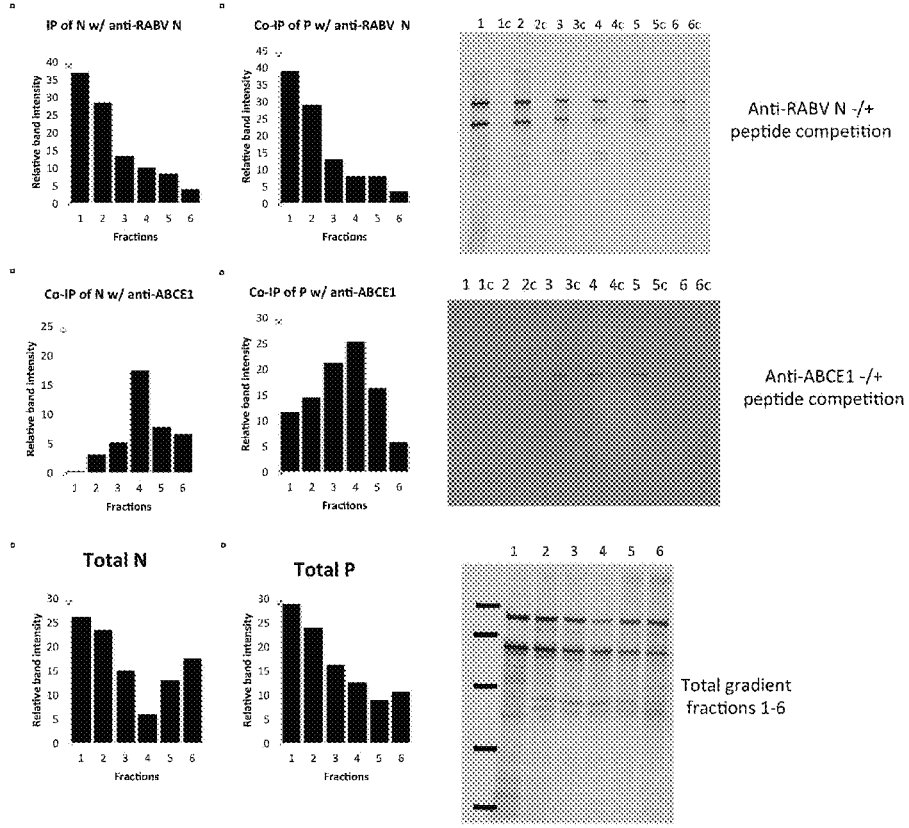

FIG. 6. A peptide epitope of RABV N exposed on the surface of RABV capsids ((1998) Antibodies: a Laboratory Manual, eds Harlow E, Lane D (Cold Spring Harbor Laboratory Publications), pp 139-243), SEQ ID NO: 1 CFFRDEKELQEYEAAELTKTDVALADD, with N terminal acetylation and C terminal amidation to mimic its internal position in the RABV N sequence, was chosen for coupling to carrier and immunization of rabbits, and polyclonal rabbit antibodies were generated essentially as described (Gerard F-C, et al. (2009) Modular organization of rabies virus phosphoprotein. *J Mol Biol* 388:978-996). Bleeds were screened by WB and immunoprecipitation of radiolabelled RABV N products. High titer sera was pooled and affinity purified as described (Gerard F-C, et al. (2009) Modular organization of rabies virus phosphoprotein. *J Mol Biol* 388:978-996). Immunoprecipitation of newly synthesized RABV N and RABV P in putative RABV assembly intermediates with affinity purified anti-RABV N and anti-ABCE1 with irrelevant affinity purified antibody and peptide competition as controls. Bands corresponding to N and P on autoradiographs (right) were quantified using image J software and displayed as relative band intensities in plots with N to the left and P to the right.

Figure 7A:
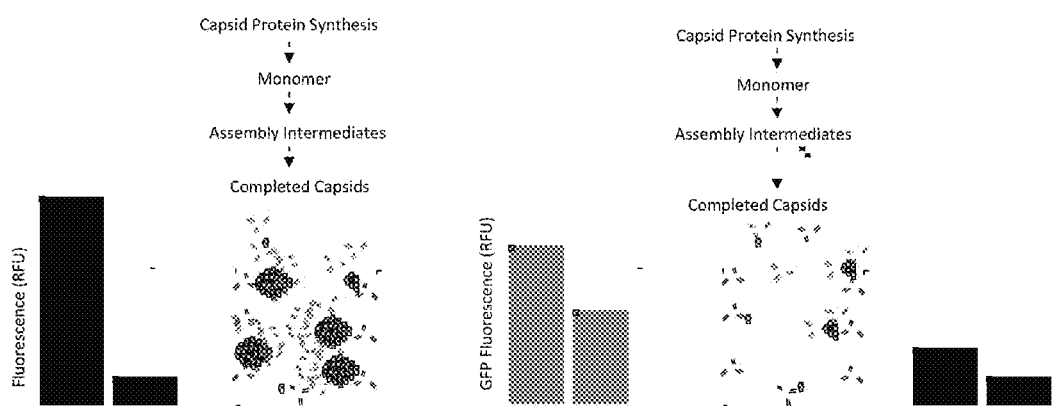
Figure 7B:
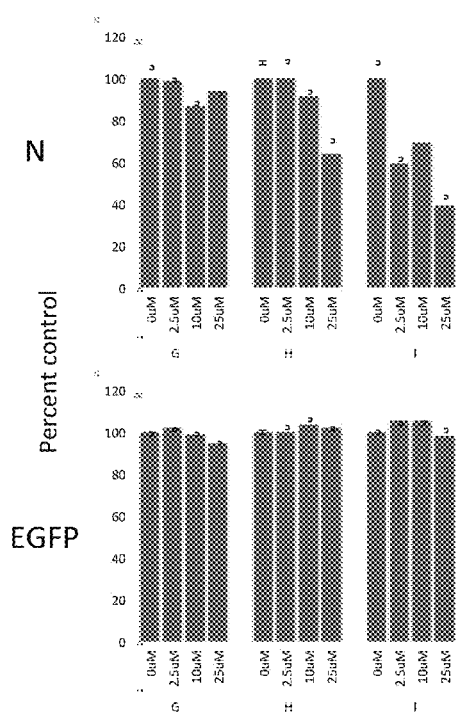
Figure 7C:
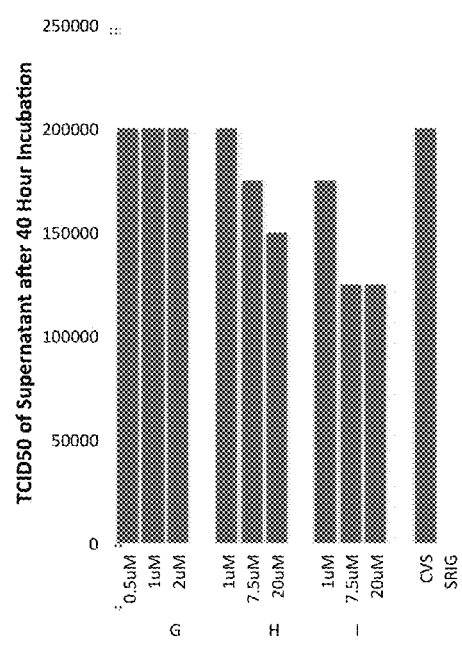

FIGS. 7A-FIGS. 7C. A. Diagram of cell-free drug screen. Capsid protein synthesis and assembly reactions were carried out as described in the methods. B. Representative early hits from the screen. Top panel are capsid assembly relative fluorescence units (RFUs); Bottom panel is eGFP RFUs. Left most compound (G) is negative for effect on capsid assembly while compounds in the middle (H) and on the right (I) represent hits subsequently validated against infectious RABV. C. TCID50 assessment of the representative three compounds whose cell-free screen data is shown in panel B. The two compounds active in the cfps screen were found to have activity in the low uM range against infectious RABV corresponding in relative potency to the readout from cfps and the activity was confirmed against street rabies as shown here.

Figure 8A:
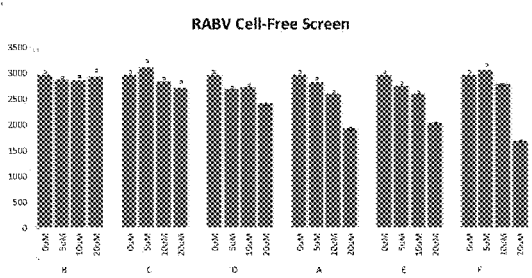
Figure 8B:
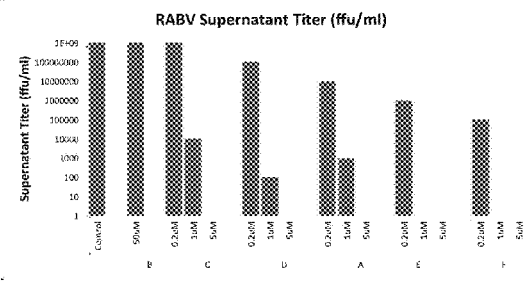
Figure 8C:
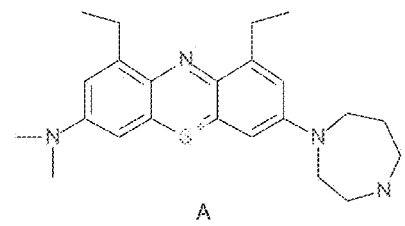

FIGS. 8A-FIGS. 8C. A. Analogs to H were synthesized and screened in the cell-free system demonstrating a robust SAR. B. Activity against infectious RABV in medium as determined by TCID50 of medium from the primary plate serially diluted and assayed for infectivity on a secondary plate. Below, RABV detection on the primary plate by direct fluorescence antibody assay (DFA). C. Structure of A, a small molecule with potent activity against RABV in cell culture in the low nanomolar range.

Figure 9:
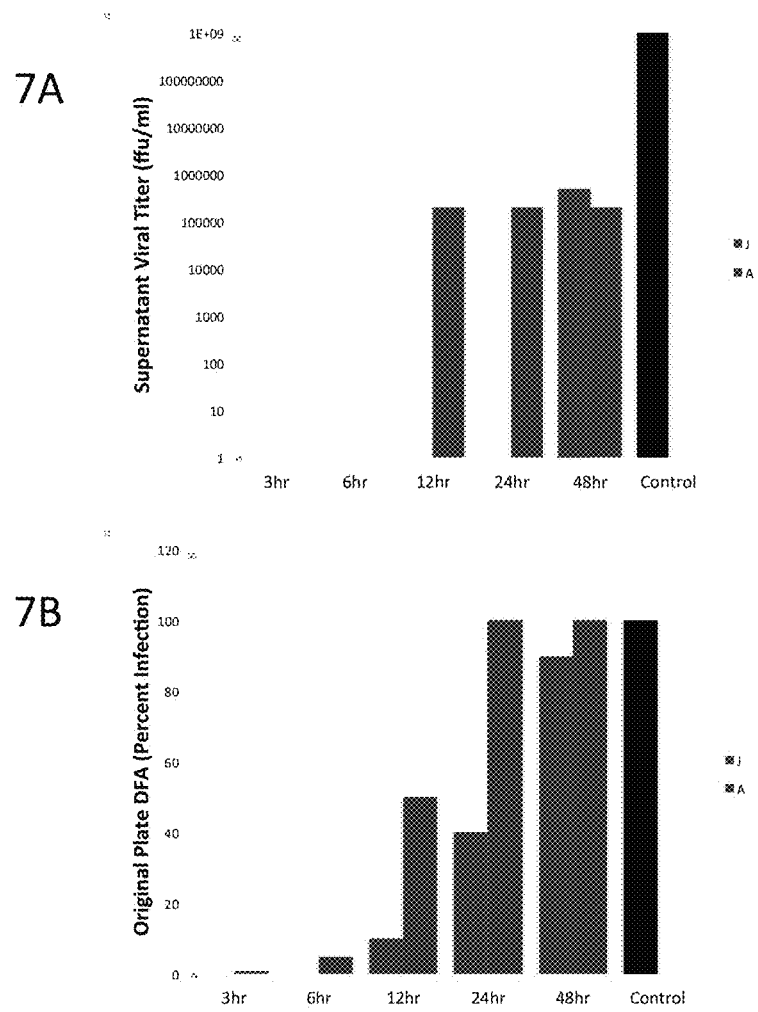

FIG. 9. In the standard infection described in Methods, compounds were added either before or immediately after addition of virus at an MOI of 1. In these experiments, compounds were added at various times after virus with subsequent incubation for 48 h, with medium then taken for serial dilution and TCID50 on a separate plate of cells in the absence of compound.

FIG. 10. Translation was carried out as described for FIG. 3C (RABV N alone) or FIG. 3D (RABV N with M and P), except that RABV N transcript in all cases was prepared in the absence of a termination codon (termed NR). As a result, newly synthesized M or P are released from ribosomes, but newly synthesized N remains substantially ribosome associated at the end of the translation reaction (26° C. or 22° C./1 h). Assessment of newly synthesized NR chains (without M or P) by ssg migration before (panel A) and after (panel B) puromycin treatment (1 uM final concentration, 22° C./15 min) and after subsequent incubation at 34° C./2 h following puromycin treatment (panel C). Note the tRNA-attached species still in the A site of the ribosome is present only in the polysome fraction and is abolished upon treatment with puromycin, while a band comigrating with RABV N is found both released (at the top of the ssg) and in the polysome fraction (middle of the ssg). Presumably these chains still in the polysome fraction, but no longer covalently associated with tRNA, represent those that have moved to the P site of the ribosome. Upon puromycin treatment, polysomes are abolished, all chains are released, and they migrate at the top of the gradient until subsequent incubation at 34° C. drives assembly as described previously in FIG. 3 and FIG. 4. Autoradiographs are shown below the panels of bar graphs that quantify the RABV N band as previously.

FIG. 11. Cfps was carried out in 384 well plates as described in methods except that RABV N transcript was replaced by RABVNR, allowing synthesis to be completed prior to staging of compound A addition. After addition of DMSO or compound, followed by 30 minute incubation at 26° C. puromycin was added at 26° C./30 minutes (compound>puromycin). Parallel samples had the compound and puromycin additions reversed (puromycin>compound) both followed by assembly incubation at 34° C./1 h. This protocol allows us to determine when the compound acts. Left hand plot shows that a dose-dependent titration is observed when compound is added after synthesis but before the NR chain is released from the ribosome by addition of puromycin. Middle panel shows that upon puromycin release, subsequent addition of drug fails to generate a comparable titration. Right hand panel demonstrates that in the absence of energy (treatment with apyrase) such that the assembly pathway is not consummated, no titration is observed upon compound addition. Compound-dependent titration of RFUs is dependent on assembly incubation at 34° C. and that addition of compound after 34° C. incubation has no effect (not shown).

Figure 12B:
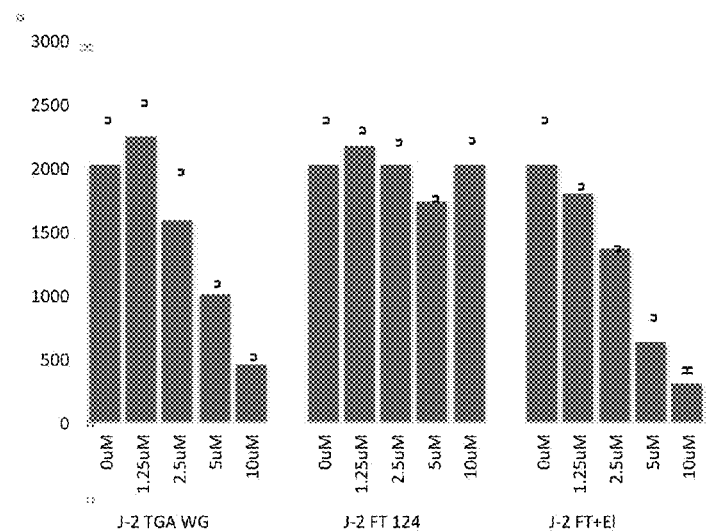
Figure 12C:
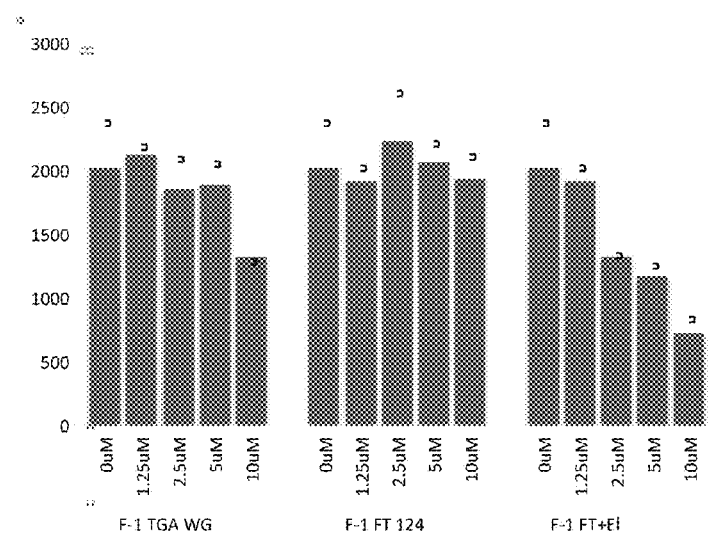

FIGS. 12A-FIGS. 12C. A. Authentic irradiated RABV was titrated to quantify WB detection by N antibody as shown previously in FIG. 3. An aliquot of starting material is analyzed in lane 5, with 1/10, 1/100 and 1/1000 of that amount by serial dilution analyzed in lanes 4, 3, 2 respectively, demonstrating that 0.1% of the loaded sample is detectable by WB. Lane 1 shows an aliquot of the flow-through that did not bind to the compound resin conjugate 1. Lanes 6-9 are the free compound eluate, a second free compound eluate, overnight compound eluate and 8M urea wash from the column 1. Lanes 10-13 are the same material from column 2. All samples were applied to SDS-PAGE and assessed by western blot. As can be seen, less than 0.1% of material loaded on the columns was bound and eluted by either free compound or 8M urea, a strong denaturant. Below is shown the WB from which quantitation was carried out above. B. WG extract was applied to column 1 and, after washing with 50 volumes of Hepes 50 mM pH 7.6, 100 mM potassium acetate, and 5 mM magnesium acetate, the column was eluted with free compound and eluates prepared from column 1. Radiolabelled RABV translation products as described in header were assessed for binding to the drug resin column. ST=starting material; FT=flow-through and EL=eluates of respective columns with material applied to SDS-PAGE and autoradiography. B and C. Cell-free drug screen with two active anti-RABV pharmacophores (one above, the other below). Leftmost plots are of starting WG extracts. Middle plots are of flow through (depleted extract). Rightmost plots are flow-throughs reconstituted with exhaustively dialyzed free compound eluate.

Figure 13:
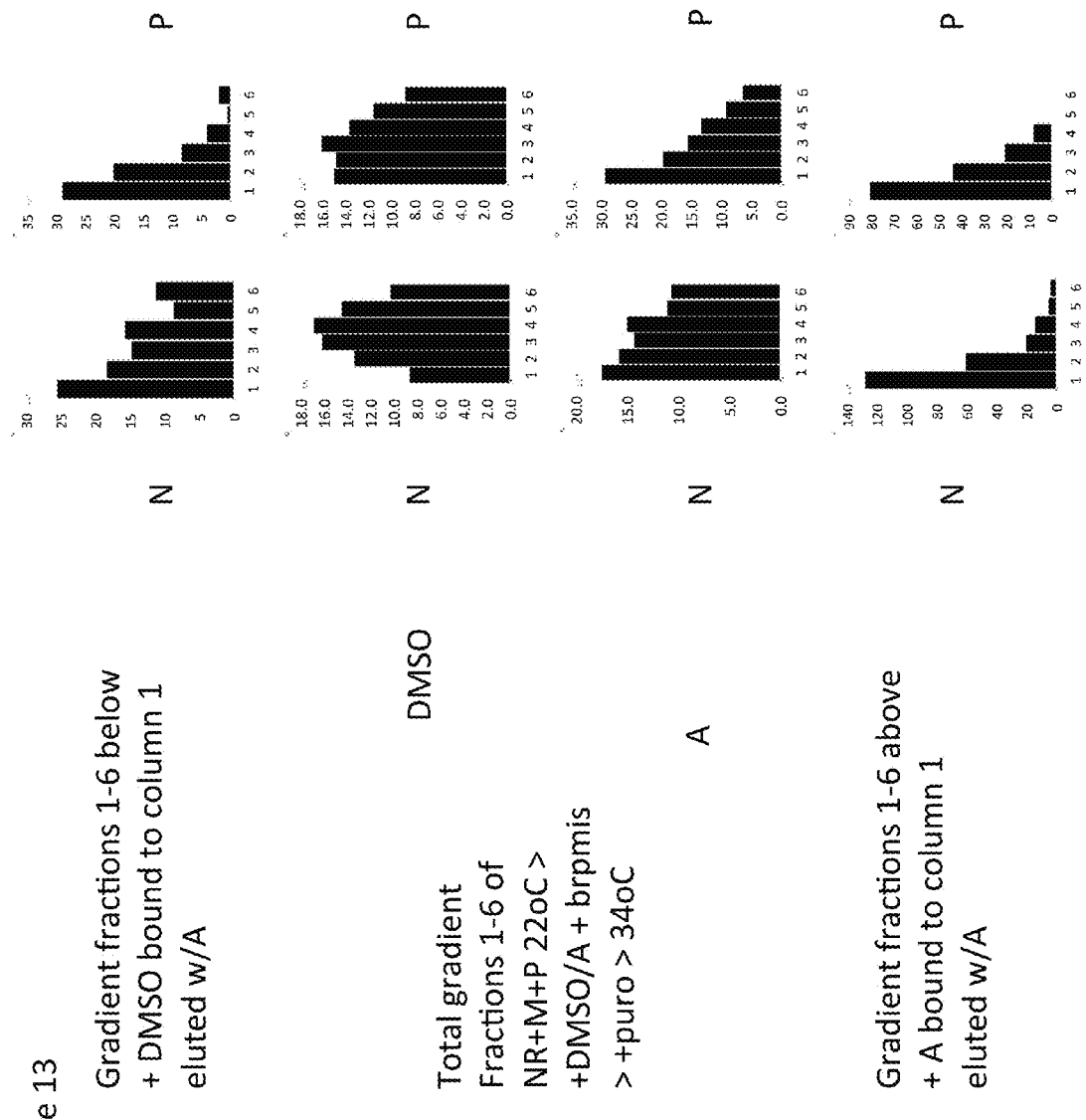

FIG. 13. Cfps in the presence of radiolabelled amino acids (see FIG. 3, FIG. 4, FIG. 10) was carried out at 22° C./1 h as previously. DMSO or A was then added to 20 μM and brpmis added to a final concentration of approximately 1 mg/ml. Incubation was then carried out at 4° C./30 min followed by treatment with puromycin at 22° C./30 min and then incubation at 34° C./2 h. Samples are applied to ssg as previously (see FIG. 3-6). Fraction 1-6 containing assembly intermediates as previously characterized (see FIG. 4) are applied to columns 1 or 2 washed with 50 volumes of buffer and eluted with 1 bed volume of 200 uM free compound A after incubation for 1 hr at 4° C. (eluate 1). The elution is repeated (eluate 2) and again overnight (eluate 3) and then the columns stripped with 8M urea. Radiolabelled products of gradient fractions from DMSO vs A treated samples bound to column 1 and eluted with free compound were analyzed by SDS-PAGE and AR. Middle panels are total gradient fractions 1-6 (DMSO above, A below). Top and bottom panels are the free compound eluates from each fraction applied to column 1. As can be seen, A impairs conversion of N from top to assembled fractions 5-7 in total N and P, but even more dramatically the presence of material bound to the column 1 is affected by compound treatment. Note that the concentration of compound on the column 1 is extremely high, >1 mM, while the solubility of the compound in buffer is substantially lower, approximately 400 uM. Thus the low concentration of compound present in the compound-treated sample is not a basis for lack of binding to the column, but rather, this is a result of a change in the composition of the assembly intermediates as a consequence of assembly.

FIGS. 14A-FIGS. 14D. Silver stained SDS-PAGE showing the banding pattern of total wheat germ extract (WG). A. A eluate from column 2 to which WG had been applied (2) and A eluate from column 1 to which WG had been applied (1). Note a set of approximately a dozen protein bands in a distinctive pattern that are observed in the 1 resin conjugate eluate and not the control 2 resin conjugate eluate. B. As for A but with brpmis as starting material. Note the similarity in pattern of bands from the two sources of material capable of driving newly synthesized RABV N from fractions ½to fractions 5-7 in an energy-dependent, A inhibited manner. C. WB for ABCE1 from total WG and 1 vs 2 eluates as described. D. As for C but with brpmis. Dots indicate protein bands present in the 1 eluate that are clearly distinct from the bands present in the 2 eluate.

Figure 14B:
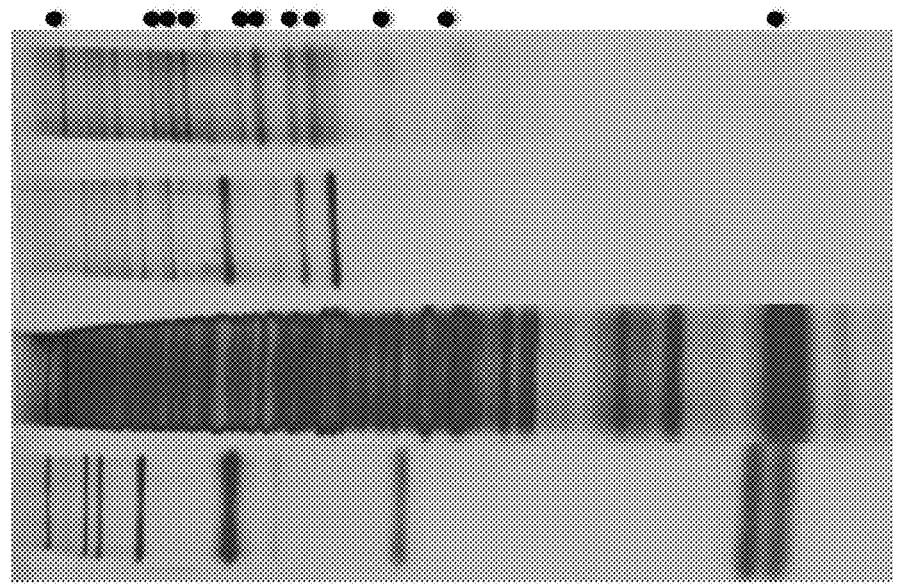
Figure 14A:
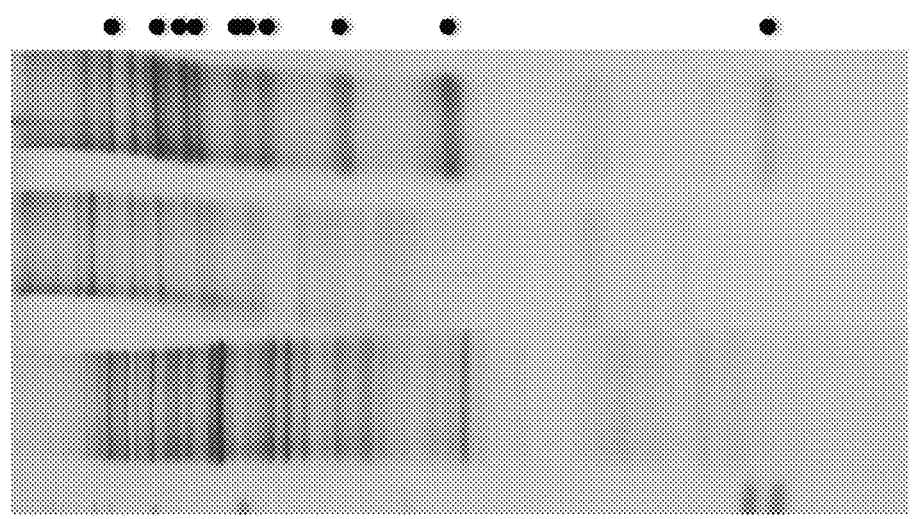
Figure 14C:
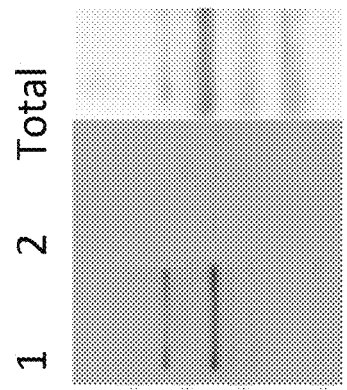
Figure 14D:
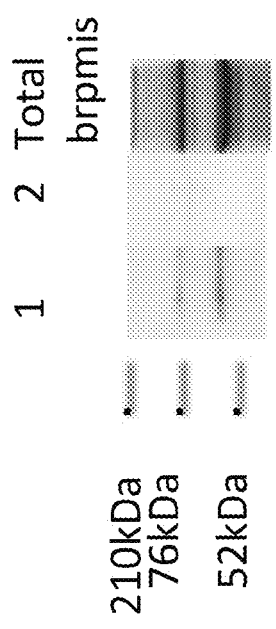
Figure 15A:
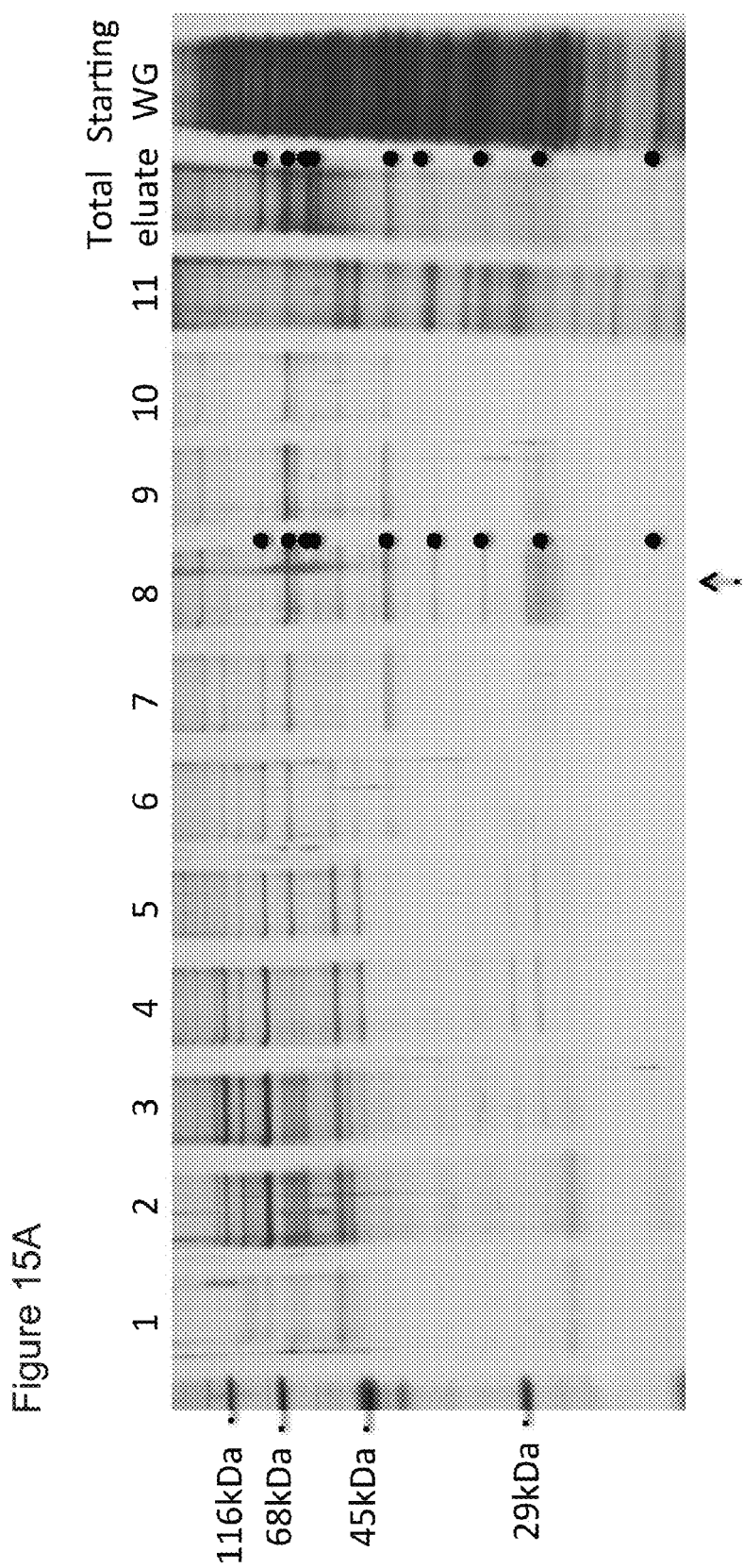
Figure 15B:
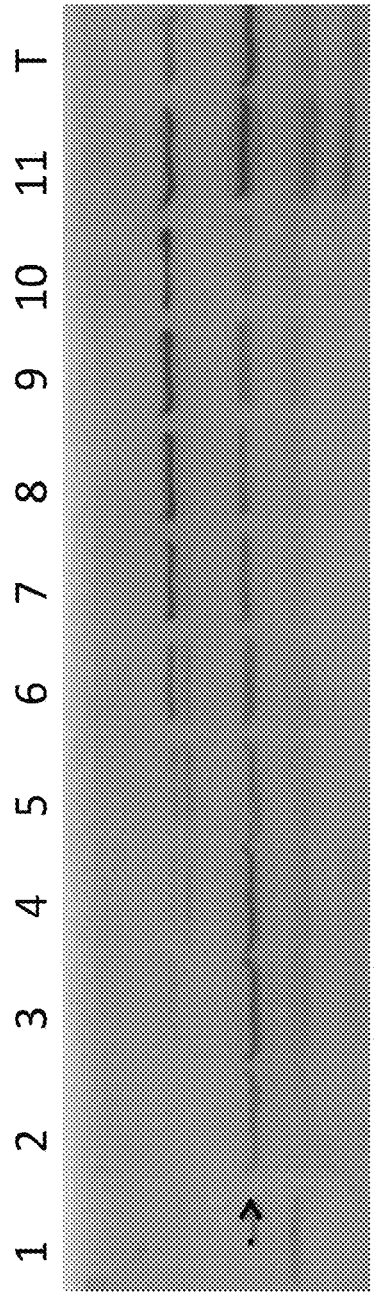
Figure 15C:
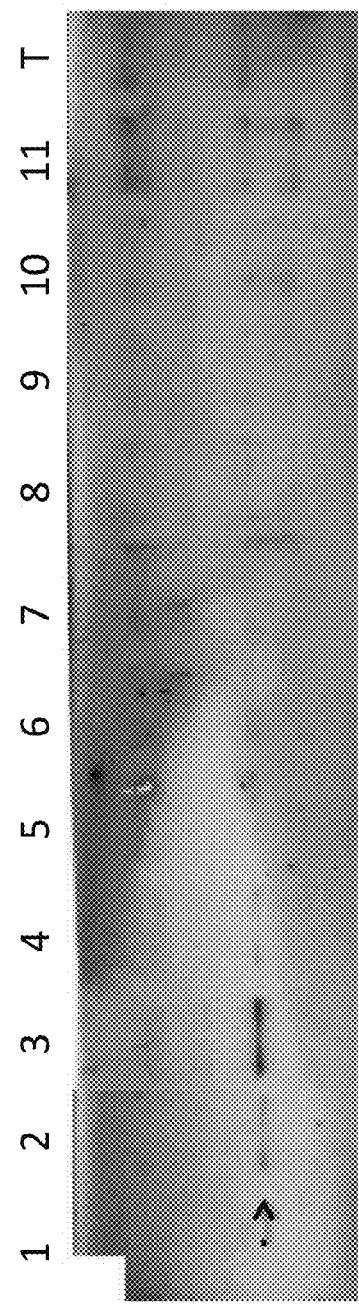

FIGS. 15A-FIGS. 15C. Samples from FIG. 14 were analyzed by glycerol gradients (5-35% in Tea 10 mM pH 8, NaCl 10 mM Mg Ac 1 mM and EDTA 0.2 mM with 0.35% TRITON™ x-100 (detergent, TRITON is a trademark of Dow Chemical Company)) after 4 h at 55K rpm TLS-55 rotor in 2 ml with 200 ul sample load and 200 ul fractions. A. Silver stain across the glycerol gradient. Note the presence of a set of bands reminiscent of the pattern observed in WG 1 eluate and brpmis 1 eluate (FIG. 14A and FIG. 14B), that run together as a complex in the middle of the glycerol gradient (indicated by dots). B and C. Glycerol gradient profiles of (B) total brpmis and (C) brpmis 1 eluate analyzed by WB with affinity purified anti-ABCE1 antibody as previously.

FIG. 16. Model for RABV-host multiprotein complex formation as reconstituted by cfps. 1, Dynamic assembly machines in the cytosol. 2, RABV P newly synthesized and released 3, Binding of RABV P which may be a very early step based on a number of observations to be demonstrated elsewhere (Lingappa et al. in preparation). 4, Nascent N growing or ribosomes. 5, Binding of nascent, nearly completed RABV N by P-containing assembly intermediates. 6, P and N-containing assembly intermediates. Note the changing orientation of the assembly machine with the growing N and P containing complexes. 7, serial action of assembly machine(s) builds the multiprotein complex. Presumably A's action is on a critical protein-protein interaction occurring during 5 and before 6 (indicated by the duplicate 5 with red X.

FIG. 17. Sequence of cDNA encoding Rabies nucleoprotein (RABV N) with termination codon (TAA) removed.

FIG. 18. Sequence of mRNA encoding RABV N without the termination codon.

FIG. 19. Sequence of mRNA encoding RABV N with the termination codon present. FIG. 19*a*. Sequence of downstream (3') oligonucleotide used to amplify by PCR the RABV N coding region without the stop codon. FIG. 19*b*. Sequence of upstream (5') oligonucleotide used to amplify by PCR the DNA encoding RABV N without the stop codon in a manner expressible using bacteriophage SP6 RNA polymerase.

DETAILED DESCRIPTION OF THE INVENTION

Abbreviations

ATP binding cassette family E1 (ABCE1); Cell-free protein synthesis (cfps); Dimethylsulfoxide (DMSO); Direct fluorescent antibody assay (DFA); ER (endoplasmic reticulum); Horseradish peroxidase (HRP); Human immunodeficiency virus (HIV); Hepatitis B virus (HBV); Hepatitis C virus (HCV); Immobilized apyrase (iapy); Influenza virus (FLUV); Polyacrylamide gel electrophoresis in sodium dodecyl sulfate (SDS-PAGE); RABV (rabies virus); Brain post mitochondrial supernatant (brpmis); Signal Recognition Particle (SRP); Structure activity relationship (SAR); Sucrose step gradient (ssg); and Western blot (WB).

Definitions

Unless otherwise noted, the technical terms used herein are according to conventional usage as understood by persons skilled in the art. Definitions of common terms in molecular biology may be found in standard texts (e.g. Benjamin Lewin, Genes V, published by Oxford University Press, 1994 (ISBN 0-19854287-9); Kendrew et al. (eds.), The Encyclopedia of Molecular Biology, published by Blackwell Science Ltd, 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8)).

A "multiprotein assembly", as used herein refers to a functional assembly of proteins, which participates in the assembly of a "multiprotein structure" implicated in a disease (e.g., a viral capsid") or in the folding of a protein which is misfolded (e.g., amyloid protein) or in the mislocation of a protein. The "multiprotein assembly" is a functional component of a disease state.

A "multiprotein structure" is a structure that is present in a disease state, for example a viral capsid or a protein aggregate but is not otherwise present in a host or is present at a level that does not cause clinical disease.

Translation system: The term "translation system" refers to the components necessary to incorporate a naturally occurring amino acid into a growing polypeptide chain (protein). Components of a translation system can include, e.g., ribosomes, tRNAs, synthetases, mRNA and the like. The components of the present invention can be added to a translation system, in vivo or in vitro. A translation system can be a cell, either prokaryotic, e.g., an *E. coli* cell, or eukaryotic, e.g., a yeast, mammalian, plant, or insect cell.

The term "messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA. "Antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, i.e., at the 5' non-coding sequence, 3' non-coding sequence, introns, or the coding sequence. In addition, as used herein, antisense RNA may contain regions of ribozyme sequences that increase the efficacy of antisense RNA to block gene expression.

The term "stop (or "termination") codon" refers to a unit of three adjacent nucleotides in a polynucleotide coding sequence that specifies translational termination of protein synthesis (i.e., mRNA translation) by the ribosomal complex.

The phrase "cell-free translation system," as used herein, refers to any type of system capable of synthesizing proteins in vitro in the absence of viable cells. An exemplary system is a cell-free protein synthesis system derived from wheat germ extract.

The term "expressing" and "expression," as used herein, refer to the production of a protein, peptide, or nucleotide sequence, and include transcription into an RNA product, post-transcriptional modification and/or translation into a protein product or polypeptide from a DNA encoding that product, as well as possible post-translational modifications.

The terms "polypeptide" or "peptide" or "protein" are used interchangeably herein, to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Macromolecular structures such as polypeptide structures can be described in terms of various levels of organization. For a general discussion of this organization (see, e.g., Alberts et al., *Molecular Biology of the Cell* ($3^{rd}$ ed., 1994) and Cantor and Schimmel, *Biophysical Chemistry Part I: The Conformation of Biological Macromolecules* (1980)). "Primary structure" refers to the amino acid sequence of a particular peptide. "Secondary structure" refers to locally ordered, three dimensional structures within a polypeptide. These structures are commonly known as domains, e.g., enzymatic domains, extracellular domains, transmembrane domains, pore domains, and cytoplasmic tail domains. Domains are portions of a polypeptide that form a compact unit of the polypeptide and are typically 15 to 350 amino acids long. Exemplary domains include domains with enzymatic or other functional activity. Typical domains are made up of sections of lesser organization such as stretches of 3-sheet and a-helices. "Tertiary structure" refers to the complete three dimensional structure of a polypeptide monomer. "Quaternary structure" refers to the three dimensional structure formed by the noncovalent association of independent tertiary units.

A "protein implicated in disease," or "target protein," as used herein, are interchangeable and refer to a whole protein molecule, including but not limited to, viral capsid proteins, or a portion thereof, i.e., cytoplasmic domain or other domain of a protein. Also included are aberrant host proteins, e.g., misfolded (e.g., "conformational disease") or mislocated proteins. Proteins implicated in disease include those implicated in neurological disorders, cancer and pathological infections.

The term "virus" or "viral," as used herein, refers to minute infectious agents, which, with certain exceptions, are not observable by light microscopy, lack independent metabolism, and are able to replicate only within a living host cell. Some exceptions include, but are not limited to, the cell-free translation system described herein. These individual particles (i.e., for example, virions) typically comprise nucleic acid and a protein shell or coat; some virions also have a lipid containing membrane. The term virus encompasses all types of viruses, including animal, plant, phage, and other viruses.

The term "viral capsid" or "capsid," as used herein, refers to the protein coat that surrounds the viral nucleic acid. Viral capsids have interior surfaces and exterior surfaces. The interior surface of a viral capsid is the surface that is normally exposed to the viral nucleic acid. The exterior surface of a viral capsid is the surface that is generally exposed to the environment. The phrase "viral capsid assembly" refers to the process of arranging viral capsid proteins in a manner sufficient to generate a viral capsid.

The term "capsid interacting protein," as used herein, refers to protein that interacts with a viral capsid either during or after its assembly. The capsid interacting protein may be endogenous to a virus, may be exogenously added, or present in the cell-free extract. Capsid interacting proteins can include, but are not limited to, capsid chaperones and proteins that have catalytic actions favoring capsid formation.

The term "components," as used herein, refers to constituents of the cell-free translation system necessary to incorporate a naturally occurring or non-natural amino acid into a growing polypeptide chain. For example, components can include, but are not limited to, buffers, amino acids, nucleic acid transcripts, ATP, GTP, creatine phosphate, labeled amino acids, myristoyl CoA lithium salts, RNase inhibitors, creatine kinases, and tRNAs. Components are described in greater detail herein.

The phrase "detectable moiety" or "conjugate" refers to any atom, molecule or a portion thereof, the presence, absence or level of which is directly or indirectly monitorable. A variety of detectable moieties are well known to those skilled in the art, and can be any material detectable by spectroscopic, photochemical, biochemical, immunochemical, electrical, optical or chemical means. Such detectable labels can include, but are not limited to, magnetic beads, fluorescent dyes, radiolabels, enzymes, and colorimetric labels such as colloidal gold or colored glass or plastic beads. In various embodiments a detectable moiety is conjugated to a protein implicated in a disease process.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code. Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes. Amino acid substitutions, deletions or additions to individual or a small percentage of amino acids in the encoded sequence is a conservatively modified variant, where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)). Amino acids can also include one or more radioactive isotopes, e.g., 35S methionine.

The term "nucleic acid" refers to deoxyribonucleotides or ribonucleotides and polymers thereof in either single- or double-stranded form, and complements thereof. Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions can be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide. A particular nucleotide sequence also implicitly encompasses "splice variants," which as the name suggests, are products of alternative splicing of a gene. After transcription, an initial nucleic acid transcript can be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

The phrase "in vitro transcription reaction," as used herein, refers to a transcription reaction that takes place in a cell-free environment using largely purified components, for example, purified DNA template and purified DNA-dependent RNA polymerase.

The term "modulates" or "modulated," as used herein, means to interact with a target protein either directly or indirectly so as to alter the activity of the target protein, including, for example, to inhibit the activity of the target protein, or to limit or reduce the activity of the target protein. Accordingly, the phrase "modulates a cellular function" means to alter the function of a way, which can include, but is not limited to, inhibition of protein synthesis or inhibition of protein assembly into molecular structures such as viral capsids. Exemplary candidate compounds of the invention modulate the formation or activity of a multiprotein assembly.

The term "candidate compound" or "compound" or "drug candidate" or "modulator" or grammatical equivalents, as used herein, describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid, fatty acid, polynucleotide, oligonucleotide, etc., to be tested for the capacity to directly or indirectly modulate assembly or function of a multiprotein assembly. The candidate compound can be in the form of a library of candidate compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound" or "candidate") with some desirable property or activity, e.g., inhibiting activity, creating variants of the lead compound, and evaluating the property and activity of those variant compounds. Often, high throughput screening (HTS) methods are employed for such an analysis. Compounds can be inhibitors, activators, or modulators of, for example, of the assembly or function of a multiprotein assembly. Inhibitors are compounds that, e.g., bind to, partially or totally block assembly or action by activity, decrease, prevent, delay activation, inactivate, desensitize, or down regulate activity or expression of, for example, nucleic acids or polypeptides derived from the cell-free system described herein, e.g., antagonists. Activators are compounds that increase, open, activate, facilitate, enhance activation, sensitize, agonize, or up regulate, for example, nucleic acids, polypeptides or multiprotein assemblies derived from the cell-free system described herein, e.g., agonists. Inhibitors, activators, or modulators also include genetically modified versions of the proteins derived from the cell-free system, e.g., versions with altered activity, as well as naturally occurring and synthetic ligands, substrates, antagonists, agonists, antibodies, peptides, cyclic peptides, nucleic acids, antisense molecules, ribozymes, or small chemical molecules, for example.

The phrase "small organic molecule" refers to a candidate compound which is an organic molecule, either naturally occurring or synthetic, that has a molecular weight of from about 50 to about 2500 daltons, preferably less than about 2000 daltons, preferably between about 100 and about 1000 daltons, more preferably between about 200 and about 500 daltons.

The term "biopharmaceutical" or "biopharmaceutical compound," as used herein, refers to any candidate compound such as a protein, peptide, polypeptide, antibody, or the like, which can be expressed endogenously in a biological system under genetic control and which confers biological activity toward pharmaceutical or therapeutic use. The biopharmaceutical or biopharmaceutical compound can be constitutively or inducibly expressed. The biological system can be an in vivo biological system and/or an in vitro biological system.

The Methods

In a first embodiment, the invention provides a whole pathway screen to determine whether a candidate compound is effective at treating a disease that involves the assembly of multiprotein structures such as viral capsids, or misfolded proteins, e.g., amyloid fibrils. In various embodiments, the screen is performed using a translation system, e.g., a cell-free translation system. In an exemplary embodiment, the screen is based upon confirming the ability of a candidate compound to interrupt the formation of a multiprotein assembly or the interaction between a multiprotein assembly and a second protein translated in the translation system. The interruption of the interaction between the multiprotein assembly and the second protein is an indication that the candidate compound is an effective agent (or starting point for development of an effective agent) for treating the disease state of interest.

Thus, in one embodiment, the invention provides a method for assaying a candidate compound for its ability to interfere with the function of a multiprotein assembly implicated in a disease. The multiprotein assembly can play one or more role in the initiation, advancement or treatment of the disease state. For example, the multiprotein assembly can participate in folding of a second protein, or the formation of multiprotein structures incorporating the second protein or both. The second protein is preferably a protein that is implicated in the disease of interest. An exemplary method includes the use of a cell-free translation system including a ribosome, a truncated m-RNA which is missing a stop codon at its 3'-terminus and the components of the translation system necessary for it to perform m-RNA translation. The truncated m-RNA encodes a host protein that is known or is thought to play a role in a multiprotein assembly ("protein substrate") that interacts with one or more second protein implicated in the disease of interest. Because of the lack of a stop codon, the newly synthesized protein, the truncated m-RNA, or both are not released from the ribosome upon completing the synthesis of the host protein. In various embodiments, the protein is complexed to the ribosome at a site that is accessible to an A site. In an exemplary embodiment, the protein substrate is not complexed to a t-RNA. In various embodiments, one or more of the truncated m-RNA and the second protein are released from the ribosome upon treatment of the ribosome complex with puromycin.

The second protein is also expressed in the translation system and the translation system is contacted with the candidate compound prior to, during and/or after synthesis of the host protein, the second protein or both. In various embodiments, the ability of the candidate compound to disrupt the interaction of a multiprotein assembly and a second protein is determined and the presence of this ability is interpreted as an indication that the candidate compound is a useful therapeutic or lead compound for treating or preventing the disease of interest. The methods of determining whether the second protein has been incorporated into a multiprotein structure (e.g., a viral capsid) or is misfolded (e.g., an amyloid fibril) are well-known in the art. Methods of determining whether a second protein is incorporated into a viral capsid are set forth in the Examples appended hereto.

In operation, the candidate compound interferes with the assembly or function of the mulitprotein assembly by interacting with any one or more proteins in the multiprotein assembly or at any location on the second protein. For example, in some embodiments, the candidate compound binds to site on a single protein, one or more site at an interface between two proteins interacting with each other, or at one or more site at an interface between three, or more than three, proteins that are interacting with each other to form the multiprotein assembly.

In various embodiments, the candidate compound interferes with the assembly or function of the multiprotein assembly by binding to one or more active site (e.g., enzymatic activity) of a single protein, one or more active site of each of two proteins or one or more active site of each of three, or each of more than three, proteins that are interacting with each other to form the multiprotein assembly.

In an exemplary embodiment, the candidate compound interferes with the assembly or function of the multiprotein assembly by binding to one or more allosteric site of one protein, one or more allosteric site of each of two proteins or one or more allosteric site of each of three, or each of more than three, proteins that are interacting with each other to form the multiprotein assembly.

Exemplary diseases for which candidate therapeutic compounds can be investigated include, without limitation, viral infections, bacterial infections, cancer, and diseases in which proteins are misfolded, e.g., Alzheimer's disease.

When the disease of interest is a viral infection, the infection can be by any one or more member of the group Flaviviridae, Togaviridae, Bunyaviridae, Arenaviridae, Filoviridae, Poxviridae, Orthomyxoviridae, Rhabdoviridae, Herpesviridae, Coronaviridae, Paramyxoviridae, Hepadnaviridae, Bornaviridae, Picornaviridae, Retroviridae, Reoviridae, Papillomaviridae, Adenoviridae, Astroviridae, and Polyomaviridae.

In another exemplary embodiment, there is provided an assay for determining whether a candidate compound interferes with a target that is a host target or a target encoded by a pathogenic organism. The method is based on the removal of host proteins that bind to the candidate compound from the translation medium by contacting an initial preparation of the medium, which is uncharged by coding genetic material, with an affinity chromatography device that includes the candidate compound immobilized thereon. The material that is not captured by the affinity chromatography device is collected in a flow through fraction. The device is then eluted with an eluent that includes the candidate compound to displace the proteins bound to the immobilized candidate compound from the affinity chromatography device. The material that is eluted off is collected and is exhaustively dialyzed to remove both free and bound candidate compound to form an eluent fraction. Translation of a host protein and a second protein is performed in a medium including the flow through fraction in the presence of the candidate compound. If there is no evidence of the assembly of a multiprotein structure incorporating the second protein or of a misfolded protein, this is an indication that protein substrate for the multiprotein assembly is a host protein and that it was removed from the medium by affinity chromatography on the candidate compound. In various embodiments, the flow through fraction and the eluent fraction are combined and translation of a host protein and a second protein is performed in the resulting medium. If there is evidence of the assembly of a multiprotein structure incorporating the second protein or of a misfolded protein, this is an indication that the substrate protein for formation of the multiprotein assembly is a host protein that interacts specifically with the candidate compound.

Thus, in various embodiments, the invention provides a method of verifying that a target for a candidate compound which interferes with the assembly or function of a multiprotein assembly implicated in a disease is a host target. An exemplary multiprotein assembly participates in folding of a second protein, formation of a multiprotein structure comprising the second protein or a combination thereof. An exemplary method includes: (a) contacting an initial medium for a cell-free translation system including one or more host protein with an affinity chromatography device having said candidate compound immobilized thereon. The candidate compound is immobilized on the chromatography device either directly or through a linker. In various embodiments, the contacting is performed under conditions appropriate to bind at least one member of the multiprotein assembly to the candidate compound. In step (b), the chromatography device is washed with a first eluent, removing species not bound to the immobilized candidate compound. The eluent from the device is collected and is termed a flow through fraction. The device is then washed with a second eluent, which preferably includes the candidate compound and which displaces the bound proteins from the device. This fraction is termed an eluent fraction.

In various embodiments the candidate compound is combined with the flow through fraction and this resulting first mixture is used for cell-free translation of an m-RNA sequence. The m-RNA sequence encodes a protein substrate of the multiprotein assembly. In various embodiments, the m-RNA sequence is a truncated m-RNA sequence lacking a stop codon at its 3'-terminus. In a preferred embodiment, upon completion of translation of the truncated m-RNA sequence, the protein substrate remains complexed to the ribosome. An exemplary site for protein complexation is a site that is accessible to an A site. It is generally preferred that the protein substrate is not complexed to a t-RNA. The cell-free translation system is also used to synthesize the second protein, generally essentially simultaneously with synthesis of the first protein. The cell-free system is assayed to determine whether the second protein was misfolded, the multiprotein structure comprising the second protein was formed or both. If there is no evidence of the assembly of a multiprotein structure incorporating the second protein or of a misfolded protein, this is an indication that protein substrate for the multiprotein assembly is a host protein and that it was removed from the medium by affinity chromatography on the candidate compound.

In some embodiments, it is desired to confirm or augment the results from the first portion of the assay. In exemplary embodiments, the candidate compound is combined with the flow through fraction and the eluent fraction. The second mixture is used in the cell-free translation of the truncated m-RNA sequence lacking a stop codon at its 3'-terminus, and the synthesis of the second protein. The cell-free system is assayed to determine whether the second protein was misfolded, the multiprotein structure comprising the second protein was formed or both. If there is no evidence of the assembly of a multiprotein structure incorporating the second protein or of a misfolded second protein, this confirms that said initial medium does not include a host target for the candidate compound. Alternatively, it confirms that the host target for the candidate compound is removed by contacting the medium with the immobilized candidate compound, and confirmation of folding of the second protein or formation of the multiprotein structure including said second protein confirms that said host target for said candidate compound is removed by contacting with said immobilized candidate compound and, therefore, interacts with the candidate compound.

The Compositions and Kits

In various embodiments, the invention provides an isolated ribosomal complex comprising a ribosome having a first site accessible to an A site. The first site is complexed to a protein synthesized from an m-RNA lacking a stop codon and the protein is not complexed to a t-RNA. In an exemplary embodiment, the protein is a full length protein. In various embodiments, the protein is a portion of a full length protein. In an exemplary embodiment, the ribosomal complex is isolated from the medium in which it was produced and is essentially free from all components of the original medium with the exception of, in one embodiment, the truncated m-RNA. In an exemplary embodiment, the complex is isolated and the ribosomal complex includes the truncated m-RNA from which the protein was synthesized as a component of the complex. In various embodiments, the medium in which the complex is produced is a cell-free translation system. In an exemplary embodiment, the cell-free translation system is a wheat germ translation system.

In various embodiments, the ribosomal complex is isolated by binding to an affinity chromatography device. When the complex is bound to the affinity chromatography device, the complex is isolated according to the invention.

In an exemplary embodiment, the invention provides a mixture of the isolated ribosomal complex immobilized on an affinity chromatography device. In an exemplary embodiment, the truncated m-RNA is a component of the ribosomal complex. In various embodiments, the complex is immobilized to the affinity chromatography device through binding with a candidate compound immobilized on the device.

In various embodiments, the invention provides a mixture of the isolated ribosomal complex and a candidate compound. In an exemplary embodiment, this mixture is a component of an assay. In various embodiments, the isolated ribosomal complex is in a mixture in an assay format including at least one candidate compound and at least one additional component appropriate for assaying the effect of the candidate compound on the isolated ribosomal complex.

In another embodiment, a kit for cell-free assay for determining whether a candidate compound is effective against a target protein or multiprotein assembly is provided.

In another embodiment, a kit for assaying the effect of a candidate compound on the assembly of viral capsid is provided. The kit comprises a cell-free mixture comprising not more than about 5% wheat germ extract, components necessary for expression of proteins required for viral capsid assembly and instructions sufficient for use of the kit in a cell-free expression experiment.

In another embodiment, a kit for a cell-free assay to determine whether a compound modulates assembly or function of a multiprotein assembly is provided. An exemplary kit comprises one or more of a cell-free mixture comprising one or more components of a cell-free assay system, components necessary for expression of the protein, and instructions sufficient for use of the kit in a cell-free expression experiment. In an exemplary embodiment the cell-free assay system is a wheat germ assay system. In an exemplary embodiment, the wheat germ assay system includes not more than about 5% wheat germ.

In another embodiment, a kit for determining whether a compound modulates viral capsid assembly is provided. An exemplary kit comprises one or more of a cell-free mixture comprising one or more components of a cell-free assay system, components necessary for expression of the protein, and instructions sufficient for use of the kit in a cell-free expression experiment. In an exemplary embodiment the cell-free assay system is a wheat germ assay system. In an exemplary embodiment, the wheat germ assay system includes not more than about 5% wheat germ.

In another embodiment, a kit for determining whether a compound modulates multiprotein assembly is provided. An exemplary kit comprises one or more of a cell-free mixture comprising one or more components of a cell-free assay system, components necessary for expression of the protein, and instructions sufficient for use of the kit in a cell-free expression experiment. In an exemplary embodiment the cell-free assay system is a wheat germ assay system. In an exemplary embodiment, the wheat germ assay system includes not more than about 5% wheat germ.

The Ribosome and the Mechanism of Translation

The structure of the ribosome and the mechanism of translation, as have been revealed by recent work, are reviewed herein (Alberts, B., Johnson, A., Lewis, J., Raff. M., Roberts, K., and Walter, P., Molecular Biology of the Cell, 4th ed, 2002, Garland Science, N.Y.; Ramakrishnan, V., Ribosome Structure and the Mechanism of Translation, 2002, *Cell* 108 557-572; Schlunzen, F. et al., Structural basis for the interaction of antibiotics with the petidyl transferase center in eubacteria, 2001, Nature 413 814-821; Sytnik, A. et al., Peptidyl Transferase Center Activity Observed in Single Ribosomes, 1999, *J. Mol. Biol.* 285, 49-54; Nyborg, J., and Liljas, A., Protein biosynthesis: structural studies of the elongation cycle, 1998, *FEBS letters* 430, 95-99).

The ribosome itself is composed of two subunits, termed 30S and 50S (there are differences between bacterial and eukaryotic ribosomes—henceforth in this discussion the ribosome is presumed to come from *E. coli*, although this assumption is made for the purposes of description only and without any intention of being limiting in any way). The large unit is composed of a pair of large RNA molecules (5S and 23S), the small subunit of a single RNA molecule (30S). Each unit has several dozen small proteins attached to it (Alberts, B., Johnson, A., Lewis, J., Raff. M., Roberts, K., and Walter, P., Molecular Biology of the Cell, 4.sup.th ed, 2002, Garland Science, N.Y.). The ribosome reads the code on mRNA molecules and synthesizes the encoded protein through the mediation of tRNA molecules. The process is performed in three stages: initiation, elongation and termination.

The ribosome uses an adaptor molecule—transfer RNA, or tRNA. These molecules are a special type of RNA. At one end, they have the anticodon part that binds to the RNA codon. At the other end, they carry the amino acid corresponding to that codon. FIG. 1A shows a tRNA molecule 2, with the anticodon loop 4, the amino acid arm 6, and a loaded amino acid 8. The tRNA molecules have a cycle of being charging with amino acid and discharging. Charging, or attachment of amino acids to the tRNA molecules, is performed by the aminoacyl-synthetase enzyme family. Discharging is performed by the ribosome, serving as a ribozyme (RNA enzyme).

When tRNA is tagged (as for example with a fluorescent label), the tRNA should continue to function normally during the processes of becoming charged with an amino acid, attaching to the elongation factors, and traveling through the ribosome. Several tagging schemes have made use of the shoulder 10 of the molecule in order to create fluorescent labeling schemes that are efficient on the one hand and result in a fully functional tRNA molecule on the other hand. Several studies have shown that *E. coli* tRNAs (tRNA molecules) can be efficiently labeled at position 8, which has in many cases a 4-thiouridine base, and at position 47, which has in several cases an amine-reactive X-base (see table below; it should be noted that these position numbers are given according to a standard numbering system for tRNA molecules). tRNA functionality requires that the molecule interact properly with the aminoacyl synthetases on the one hand, and with the ribosomal machinery (including the elongation factors) on the other. tRNA recognition by aminoacyl synthetases is known to be particularly dependent on the anticodon part and the amino acid arm locus.

Figure 1B:
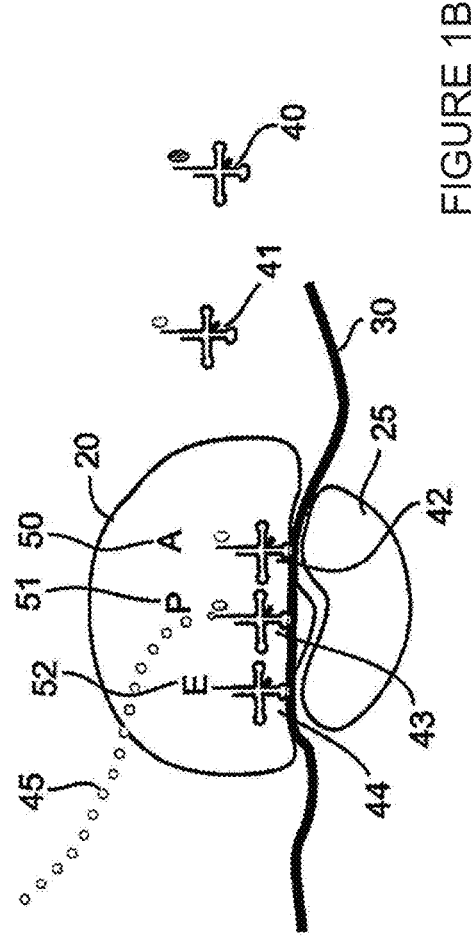
FIG. 1B describes the basic structure of a ribosome and the elongation cycle. The bacterial ribosome structure shows the larger (50S) subunit 20, smaller (30S) subunit 25, aminoacyl (A) site 50, peptidyl (P) site 51, and exit (E) site 52. 40 and 41 are undocked tRNAs. 30 shows an mRNA being decoded and 45 shows the nascent polypeptide chain being synthesized. Three docked tRNAs are shown. The first 42 is in the A (Aminoacyl) site; the second 43 in the P (Peptidyl) site, and the third 44 is in the E (exit) site.

There are three important stages in translation: initiation, elongation and termination. For monitoring protein synthesis, where protein identification is a preferred motivation, the important stage is elongation. FIG. 1B shows a schematic description of bacterial ribosome structure with the larger (50S) subunit 20, smaller (30S) subunit 25, aminoacyl (A) site 50 where tRNAs dock initially, peptidyl (P) site 51 where the growing polypeptide chain is docked, and exit (E) site 52 from where the deacylated tRNA is removed once the cycle is complete. Also shown are tRNAs that are undocked yet 40 and 41 to show that the cycle may continue further, mRNA being decoded 30 and the nascent polypeptide chain being synthesized 45. The ribosome itself is made up of large folded rRNA chains with ribosomal proteins. The larger subunit 20 contains two folded rRNAs, known as 23S and 5S. The smaller subunit 25 contains one folded rRNA, 30S (not shown). On the folded rRNA chains more than 50 ribosomal proteins are docked (not shown). They are customarily denoted by L1, L2 etc for the approximately 36 ribosomal proteins attached to the large subunit, and by S1, S2 etc for the approximately 21 ribosomal proteins attached to the small subunit (numbers given are correct for *E. coli* ribosomes).

Three docked tRNAs are seen in FIG. 1B. The first 42 is in the A (Aminoacyl) site; the second 43 in the P (Peptidyl) site, and the amino acid it carries is at this point connected to the nascent peptide; the third 44 is in the E (exit) site, it has been discharged from the amino acid and will be ejected shortly from the ribosome. The heavy line 30 indicates the mRNA being translated, and the dotted line 45 represents the polypeptide being synthesized, tied into the Peptidyl position.

The main stages of elongation are as follows. Stage 1: Codon recognition. A tRNA molecule carrying an amino acid binds to a vacant A-site, while the nascent polypeptide is attached to the P-site. Stage 2: Peptide bond creation. A new peptide bond is created and the polypeptide chain is moved to the A-site. Stage 3: Translocation. The ribosome translocates a distance of 3 nucleotides with respect to the mRNA, the two tRNA units and the polypeptide chain. Stage 4: the cycle repeats itself until a stop codon is reached.

Figure 2A:
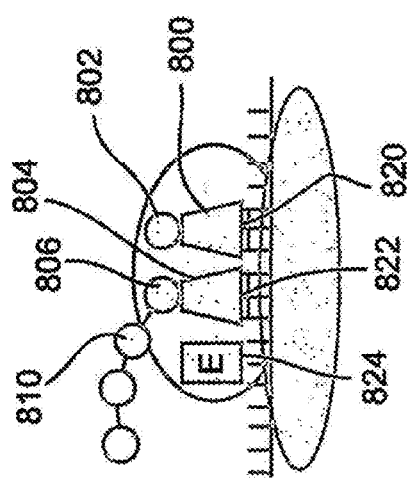
FIGS. 2A-FIGS. 2C describe the stages of the elongation cycle.
Figure 2C:
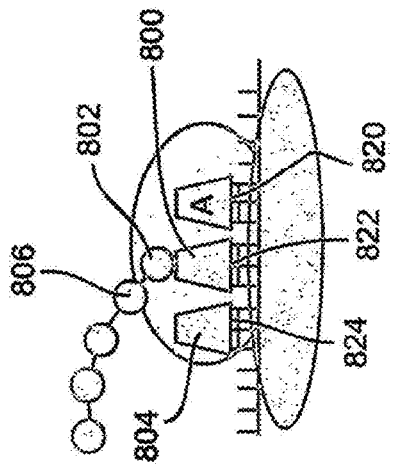
Figure 2B:
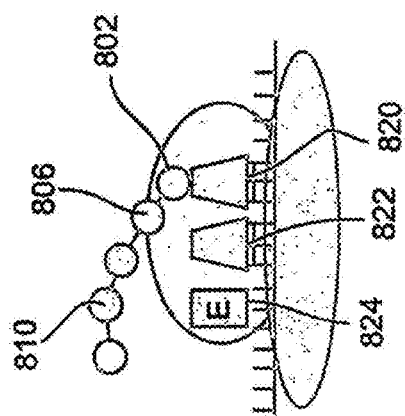

This cycle is shown as schematic diagrams in FIGS. 2A-2C. Stage 1—Codon recognition—is shown in FIG. 2A. A tRNA molecule 800 carrying an amino acid 802 binds to a vacant A-site 820, while the growing polypeptide chain 810 is attached to amino acid 806 on tRNA 804 that is docked in the P-site 822. At this stage E site 824 is shown as empty. Stage 2, peptide bond formation, is shown in FIG. 2B. A new peptide bond is created between amino acid 806 and amino acid 802, and the polypeptide chain 810 is moved to the A-site 820. Stage 3, translocation, is shown in FIG. 2C. The ribosome translocates 3 nucleotides with respect to the mRNA, the two tRNA units 800 and 804, and the polypeptide chain 810. Stage 4: the cycle repeats itself until a stop codon is reached.

Candidate Compounds—Antiviral Agents

The majority of existing anti-viral drugs are nucleoside analogs or other agents that exert their effects through an enzyme involved in producing new copies of the viral genetic material, such as a nucleoside kinase or a polymerase or reverse transcriptase or replicase. These analogs are typically metabolized into nucleotide analogs that inhibit production of viral nucleic acid, for example by inhibiting a polymerase or by causing premature chain termination of growing viral nucleic acids. The efficacy of such drugs depends on two key factors. The first is that the target virus utilized at least one virus-specific enzyme, encoded by the virus and used only by the virus, in the pathways which result in the copying of its genetic material. The second is that this enzyme is more sensitive to the drug or more efficient in utilizing it than any corresponding enzyme in the host. However, because viral and cellular nucleic acid metabolism are so similar, it is difficult to find anti-viral agents that are not used to some extent by host cell enzymes. This limits the dose of anti-viral drug that can be tolerated, which in turn may limit the utility of the drug.

Even in the case where a drug is tolerated at an effective dose, its effectiveness can be reduced markedly by the ability of a virus to mutate relatively rapidly, evolving new versions of the viral enzyme which do not utilize the drug as efficiently or which are less inhibited by the drug. Furthermore, antiviral drugs that function at the level of multiprotein assemblies of host proteins, rather than viral proteins, are anticipated to show an increased resistance to drug resistance.

The present invention provides novel methods for discovering such drugs and for treating illnesses with the drugs discovered. The methods of this invention are based in the observation that assembly of viral multiprotein complexes require one or more host-derived protein substrate. This phenomenon is illustrated herein by reference to synthesis of the rabies viral capsid, however, this is an illustration of a broader general principle and the use of rabies capsid assembly as an example of this principle is not limiting.

Such drugs have significant advantages over current antiviral agents. As noted above, the targets for the majority of the latter are enzymes involved in the synthesis of viral nucleic acids, and because host cells also contain enzymes active in the synthesis of nucleic acids it is difficult to hit the viral enzymes without also hitting the host ones. Similar problems are likely to occur for any drug target which is an active catalyst in the synthesis of a material required by both the virus and the host cell. In the methods of the present invention, these problems are avoided because the drug targets are not active catalysts in a synthetic pathway: they are devices used by a virus to secure preferential access to a synthetic pathway (protein synthesis), rather than catalysts in such a pathway. As weapons used by the virus in its attack on the host, these devices do not have any parallels within the host. Drugs which interfere with these devices therefore have minimal side effects on the host.

Such drugs are more effective than current drugs, for two reasons. First, their minimal side effects allow them to be used at higher doses. Second, it is possible for these drugs to be intrinsically more injurious to their targets than is tolerable for drugs whose targets have host homologues, because if the latter drugs are intrinsically too injurious they may harm the host homologues to some extent.

Assays for Modulators

Assays for screening modulators of assembly or activity of a multiprotein assembly, (e.g., antiviral compounds) that are based on biochemical approaches typically involve testing compounds for activities that limit or inhibit proteins that are essential for disease progression. For example key components of viral replication complex are ideal targets for antiviral screening. Further, three-dimensional structures of viral proteins, if available, can afford the possibility for rational design of drugs that will inhibit their activity. Although biochemical approaches are capable of identifying potential viral inhibitors, they are limited in their overall efficiency since only a single enzyme or protein can be tested for any potential assay. Thus, individual assays would be required to screen for inhibitors of each given viral target protein. The present invention provides a significant advance over this state of the art.

In some embodiments, modulation of proteins, e.g., viral proteins, can be assessed by determining the effect of a compound on expression, folding, and assembly of the protein in a cell-free system (e.g., with about 5% wheat germ extract). In various embodiments, modulation of viral capsid assembly can be assessed by determining the effect of a compound on capsid assembly using a cell-free system. In some embodiments, modulation of capsid interacting proteins, including but not limited to capsid assembly chaperone proteins, can be assessed by determining the effect of a compound on expression of the protein in the cell-free system of the invention (e.g., using 5% wheat germ extract). Modulation can further include, but is not limited to, modulation of infection, replication, receptor binding, cell entry, particle formation, and the like.

An advantage of using a cell-free system in the present invention is that the process of capsid formation is slowed down, thus allowing for the targeting of capsid assembly processes for modulators of capsid assembly. An advantage of using cell-free systems in the invention, such as those having about 5% wheat germ extract, is an increased sensitivity for detecting compounds that otherwise would not be detected at higher wheat germ concentrations.

Measurement of modulation of a viral protein and/or viral capsid assembly can be performed using a variety of assays, in vitro, in vivo, and ex vivo. The assays described herein can use a full length viral protein, a variant, a mutant or a fragment thereof. A suitable physical, chemical (e.g., detectable moiety) or phenotypic change that affects activity, e.g., enzymatic activity, cell surface marker expression, viral replication and proliferation can be used to assess the influence of a test compound on the proteins expressed. The assay can also make use of one or more drug designed to block or alter protein activity, capsid assembly, or the associations of chaperones with viral proteins. The assay can also identify modulators of viral capsid assembly intermediates. Moreover, genomic nucleic acid can also be encapsidated into capsids, which can be used to design drugs that interfere with encapsidation and with the design of assay systems that examine the mechanism of action of drugs that inhibit encapsidation.

A high throughput binding assay can be performed in which the translation system is contacted with a candidate compound and incubated for a suitable amount of time. A wide variety of modulators can be used, including, but not limited to, small organic molecule, or a biopharmaceutical or biological entity, such as a protein, e.g., an antibody or peptide, a sugar, a nucleic acid, e.g., an antisense oligonucleotide or a ribozyme or siRNA, or a lipid.

In high throughput assays, either soluble or solid state, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 350 (e.g., 384) modulators. If 1536 well plates are used, then a single plate can easily assay from about 100-about 1500 different compounds. It is possible to assay many plates per day; assay screens for up to about 6,000, 20,000, 50,000, or more than 100,000 different compounds are possible using integrated systems.

High throughput screening methods involve providing a combinatorial small organic molecule or peptide library containing a large number of potential therapeutic compounds (potential modulator or ligand compounds) can be used. Such "combinatorial chemical libraries" or "ligand libraries" are then screened in one or more assays to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *I Amer. Chem. Soc.* 116:2661 (1994)), oligocarbamates (Cho et al., *Science* 261:1303 (1993)), and/or peptidyl phosphonates (Campbell et al., *J Org. Chem.* 59:658 (1994)), nucleic acid libraries (see Ausubel, Berger and Sambrook, supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science*, 274:1520-1522 (1996) and U.S. Pat. No. 5,593,853), small organic molecule libraries (see, e.g., benzodiazepines, Baum *C&EN*, January 18, page 33 (1993); isoprenoids, U.S. Pat. No. 5,569,588; thiazolidinones and metathiazanones, U.S. Pat. No. 5,549, 974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Cell-Free Translation Systems

In an exemplary embodiment, a cell-free system for expressing a protein of interest is utilized as a component of the assay. The system comprises components necessary for expression of the protein of interest. In an exemplary embodiment, the protein of interest is a viral protein or a misfolded protein implicated in a disease. In various embodiments, the viral protein is a viral capsid protein. In a selected embodiment, the protein of interest is a capsid interacting protein. In a selected embodiment, the protein of interest is a host protein which undergoes assembly in a manner analogous to capsid proteins, i.e. most likely due to catalysis of formation of specific multi-protein complexes by other proteins in the cytoplasm.

In an exemplary embodiment, the protein is a non-viral protein that is a compound of a multiprotein assembly. In selected embodiments, the multiprotein assembly is implicated in diseases comprising central nervous system disorders, metabolic disorders, oncologic disorders, parasitic diseases or immunologic disorders. In an exemplary embodiment, the protein of interest is a bacterial or parasitic protein.

The viral protein can be from any virus or family of viruses. In an exemplary embodiment, the viral protein is from a virus which is a member of a viral family selected from the group consisting of Flaviviridae, Togaviridae, Bunyaviridae, Arenaviridae, Filoviridae, Poxviridae, Orthomyxoviridae, Rhabdoviridae, Herpesviridae, Coronaviridae, Paramyxoviridae, Hepadnaviridae, Bornaviridae, Picornaviridae, Retroviridae, Reoviridae, Papillomaviridae, Adenoviridae, Astroviridae, Polyomaviridae.

Cell-free translation systems provide cytosolic factors critical for translation, and support the in vitro translation of a wide variety of mRNAs into protein. The translation mechanism is sufficiently conserved so that a cell-free system can translate both prokaryotic and eukaryotic mRNAs with high efficiency. The optimal concentration of wheat germ extract can be determined for each RNA sequence to be translated.

Cell free translation systems are well known. Recently a synthetic system, built entirely from purified recombinant factors, and that has a high protein synthesis yield, was described (Shimizu et al., Cell-free translation reconstituted with purified components. *Nat Biotechnol.* 2001 August; 19(8):751-5). Kits and detailed instructions can be obtained from vendors such as Promega (Madison, Wis.). These systems are used for several applications, such as ORF validation and functional analysis of gene products. The systems contain ribosome-rich media with the required tRNAs and amino acids, and little or no mRNA. When mRNA is introduced, the ribosomes begin translation and proteins are produced. Often the proteins are produced radiolabeled. This enables the researcher to verify that the required proteins were in fact produced. The optional, exemplary system disclosed here is easier to assemble in vitro than in vivo, since labeling techniques are more readily available and easier to implement.

In an exemplary embodiment, a wheat germ extract cell-free system is utilized. Wheat germ extract is commonly used for cell-free translation reactions, and was initially described by various investigators (e.g., Roberts, B. E. and Paterson, B. M. (1973, *PNAS* 70, p. 2330)). Wheat germ extract is desirable because is supports translation of prokaryotic, eukaryotic, and viral RNAs. Wheat germ extract has been further shown to be useful in cell-free systems designed to assemble viral capsids (Lingappa et al. *J Cell Bio* 125: 99-111 (1994); Lingappa et al. *J Cell Bio* 136:567-581 (1997); Singh et al. *Virology* 279:257-270 (2001); Zimmerman et al. *Nature* 415:88-92 (2002); Lingappa and Thielen, *Methods Mol Biol.* 485:185-95 (2009)). Viral capsids are the protein shell of a virus that protects the viral genome, and its assembly is a process, catalyzed by host factors, that can be targeted to develop anti-viral drugs.

Proper wheat germ extract concentration is required for efficient protein expression. Optimal wheat germ extract concentration for robust protein expression has generally been shown to be around 40 to 50% of the total translation mix (Erikson and Blobel, *Methods Enzymology* 96:38-50 (1983)). Reports have specified that wheat germ extract is optimally used at 20% of the final reaction volume for proper capsid assembly (Lingappa and Thielen, *Methods Mol Biol.* 485:185-95 (2009)). In an exemplary embodiment, the cell free system used in the assay of the present invention includes not more than about 5% wheat germ extract. An exemplary system is set forth in commonly owned copending U.S. Provisional Patent Application No. 61/514,825 filed Aug. 3, 2011.

A cell-free expression system of use in the invention includes one or more components necessary or useful to ensure that the expression system expresses the desired protein in the desired amount and/or form. In addition to the translation apparatus, an exemplary embodiment, the further components of the system include one or more of a buffer, an amino acid, and a nucleic acid transcript. In various embodiments the composition further comprises one or more of a detectable moiety, ATP, GTP, creatine phosphate, a labeled amino acid, myristoyl CoA lithium salt, an RNase inhibitor, creatine kinase, and a tRNA. In an exemplary embodiment, the labeled amino acid comprises $[^{35}S]$ methionine. In an exemplary embodiment, the nucleic acid transcript is derived from an in vitro transcription reaction. In an exemplary embodiment, the nucleic acid transcript encodes a viral protein, e.g., a viral capsid protein. In an exemplary embodiment, the nucleic acid transcript encodes a viral capsid interacting protein. In an embodiment, the buffer comprises a member selected from potassium acetate, spermine, and dithiothreitol or other reducing agents and a combination thereof.

Cell-free translation systems can utilize a wide variety of components in addition to the translation apparatus (e.g., wheat germ extract). Described herein are exemplary basic components useful for efficient translation of proteins (e.g., viral proteins) using a cell-free translation system (e.g., wheat germ extract). However, one skilled in the art recognizes that additional components might be useful for translation and/or capsid assembly depending on the desired properties of the proteins and/or capsids produced the desired production conditions and other variables. The choice of the proper components for a cell-free system of the invention is well within the capabilities of those of skill in the art. For example, when the proteins of interest are implicated in viral infections, the use of wheat germ extract for capsid assembly is recognized known in the art for this application, and is described in more detail, for example, in Lingappa and Thielen, *Methods Mol Biol.* 485:185-95 (2009), and U.S. Pat. No. 7,638,269.

In an exemplary embodiment, the composition of the invention further includes a buffer. Cell-free translation systems generally require an appropriate compensating buffer. Potassium and magnesium concentrations of the wheat germ translation system can have dramatic effects on the efficiency of translation, and the compensating buffer is used to adjust the ion concentration of the total translation reaction to an optimum that can be determined for each mRNA being translated. Buffers can include further components for efficient protein expression, which include, but are not limited to, potassium acetate, amines (e.g., spermine), and sulfur compounds (e.g., dithiothreitol).

The composition of the invention also optionally includes a nucleic acid encoding a protein or a portion thereof. In an exemplary embodiment, the translation mixture contains transcript nucleic acid or a fragment thereof that encodes one or more protein implicated in a disease state, e.g., a viral protein. In this embodiment, the cell-free translation system involves two linked reactions: in vitro transcription and cell-free translation. RNA can be obtained by any method known in the art including, but not limited to, isolating mRNA or by making in vitro mRNA transcripts from DNA cloned into a vector containing an mRNA polymerase promoter. RNA molecules can also be generated in the same reaction vessel used for the translation reaction. In an exemplary embodiment, the mRNA is generated in situ by addition of, for example, SP6 polymerase to the reaction mixture along with the viral protein coding region or cDNA.

In an exemplary embodiment, a sample containing a virus of interest or a bodily fluid of an individual infected with a virus of interest, or infected cells from an individual, is used a source of viral nucleic acid encoding the protein for the virus. This can then be engineered behind an appropriate promoter (e.g. for SP6 polymerase), amplified by PCR and purified for transcription-linked translation. The fluid may be any bodily fluid including, without limitation, blood, serum, plasma, lymphatic fluid, urine, sputum, cerebrospinal fluid, and the like.

The endogenous mRNA present in the wheat germ extract can compete with the exogenous RNA for ribosomes and factors required for translation. It is therefore optionally advantageous to reduce the concentration of endogenous RNA by treating the prepared extract with nuclease. Such nucleases are well known in the art, and can include, but are not limited to, micrococcal nuclease from *Staphylococcus aureus*.

Methods known in the art are used to maintain energy levels sufficient to maintain protein synthesis. In an exemplary embodiment, additional nucleotide energy sources are added during the reaction. In various embodiments, energy is maintained by addition of an energy source such as creatine phosphate/creatine phosphokinase. In an exemplary embodiment, ATP and GTP concentrations present in a standard translation mixture known in the art are sufficient to support both protein synthesis and capsid formation.

In an exemplary embodiment, the virus has a myristolated intermediary. For such viruses, one can add sufficient myristoyl coenzyme A (MCoA) with or without acceptable salts to the system to enable capsid assembly. The concentration required may vary according to the particular experimental conditions, and can therefore be determined empirically.

In various embodiments, the cell-free translation systems of the invention comprise further components including, but not limited to, RNase inhibitors, ribonuclease inhibitors, protease inhibitors, microsomal membranes, and tRNAs, either alone or in combination.

With the present invention, cell-free translation systems can optionally produce one protein or many proteins, and their identification and production rates could be measured, controlled, and optimized in real time.

Detection

Proteins expressed in the cell-free system optionally include a detectable moiety. This may be a primary label or a secondary label. In an exemplary embodiment, the detectable moiety is a primary label. A primary label is one that can be directly detected, such as a fluorophore. In general, labels fall into three classes: a) isotopic labels, which may be radioactive or heavy isotopes; b) magnetic, electrical, thermal labels; and c) colored or luminescent dyes. Labels can also include enzymes (horseradish peroxidase, etc.) and magnetic particles. Preferred labels include chromophores or phosphors but are preferably fluorescent dyes. Suitable dyes for use in the invention include, but are not limited to, fluorescent lanthanide complexes, including those of Europium and Terbium, fluorescein, rhodamine, tetramethylrhodamine, eosin, erythrosin, coumarin, methyl-coumarins, pyrene, Malacite green, stilbene, Lucifer Yellow, Cascade Blue™, Texas Red, alexa dyes, phycoerythin, bodipy, and others described in the 6th Edition of the Molecular Probes Handbook by Richard P. Haugland, hereby expressly incorporated by reference.

In a preferred embodiment, a secondary detectable label is used. Accordingly, detectable moieties may be primary labels (i.e. directly detectable) or secondary labels (indirectly detectable). A secondary label is one that is indirectly detected; for example, a secondary label can bind or react with a primary label for detection, or may allow the separation of the compound comprising the secondary label from unlabeled materials, etc. Secondary labels find particular use in systems requiring separation of labeled and unlabeled proteins. Secondary labels include, but are not limited to, one of a binding partner pair; chemically modifiable moieties; nuclease inhibitors, etc.

In a preferred embodiment, the secondary label is a binding partner pair. For example, the label may be a hapten or antigen, which will bind its binding partner. In a preferred embodiment, the binding partner can be attached to a solid support to allow separation of extended and non-proteins. For example, suitable binding partner pairs include, but are not limited to: antigens (such as proteins (including peptides)) and antibodies (including fragments thereof (FAbs, etc.)); proteins and small molecules, including biotin/streptavidin; enzymes and substrates or inhibitors; other protein-protein interacting pairs; receptor-ligands; and carbohydrates and their binding partners.

In a preferred embodiment, the binding partner pair comprises biotin or imino-biotin and streptavidin. Imino-biotin is particularly preferred as imino-biotin disassociates from streptavidin in pH 4.0 buffer while biotin requires harsh denaturants (e.g. 6 M guanidinium HCl, pH 1.5 or 90% formamide at 95° C.).

In a preferred embodiment, the binding partner pair comprises a primary detectable moiety and an antibody that will specifically bind to the primary detectable moiety. By "specifically bind" herein is meant that the partners bind with specificity sufficient to differentiate between the pair and other components or contaminants of the system. The binding should be sufficient to remain bound under the conditions of the assay, including wash steps to remove non-specific binding moieties.

For immobilization of proteins, it is preferred that the other half of the binding pair is attached to a solid support. In this embodiment, the solid support may be any as described herein for substrates and microspheres, and the form is preferably microspheres as well; for example, a preferred embodiment utilizes magnetic beads that can be easily introduced to the sample and easily removed, although any affinity chromatography formats may be used as well. Standard methods are used to attach the binding partner to the solid support, and can include direct or indirect attachment methods. For example, biotin labeled antibodies to fluorophores can be attached to streptavidin coated magnetic beads.

Thus, in this embodiment, the expressed proteins comprise a binding partner that is contacted with its binding partner under conditions wherein the proteins are separated from the unproteins. These proteins can then be added to the array comprising capture probes as described herein.

In a preferred embodiment, the secondary label is a chemically modifiable moiety. In this embodiment, labels comprising reactive functional groups are incorporated into the nucleic acid. The functional group can then be subsequently labeled with a primary label. Suitable functional groups include, but are not limited to, amino groups, carboxy groups, maleimide groups, oxo groups and thiol groups, with amino groups and thiol groups being particularly preferred.

In various embodiments, the detectable moiety is a component of a fusion protein expressed by the cell-free translation system. In one embodiment, a fusion nucleic acid is introduced to the system. The fusion nucleic acid comprises nucleic acid encoding a protein of interest and a nucleic acid encoding a detectable moiety. Thus, by linking a protein of interest to a detectable molecule, for example green fluorescent protein, the presence or absence of the detectable molecule can serve to identify the protein of interest.

The nucleic acid encoding the protein of interest is operably linked to nucleic acid encoding a detectable molecule. The fusion proteins are constructed by methods known in the art. For example, the nucleic acids encoding the protein of interest is ligated to a nucleic acid encoding a detectable moiety. An exemplary detectable moiety is a fluorescent moiety. Preferred fluorescent molecules include but are not limited to green fluorescent protein (GFP), blue fluorescent protein (BFP), yellow fluorescent protein (YFP), red fluorescent protein (RFP), and enzymes including luciferase and .beta.-galactosidase. In a preferred embodiment, green fluorescent protein (GFP) or any of its derivatives including, but not limited to, EGFP (Haas et al., Curr. Biol. 6:315-324 (1996)), d2EGFP (Clontech), EBFP (Clontech), GFPuv (Crameri et al., Nature Biotechnol. 14:315-319 (1996)), BFP (blue fluorescent protein), YFP (yellow fluorescent protein) and RFP (red fluorescent protein) is used as a detectable moiety. GFP expression and loss of GFP expression can be monitored noninvasively in vivo in individual cells.

When single molecule detection is required in in vitro translation systems, the molecules are preferably immobilized. There are several approaches to immobilization of biomolecules. Biomolecules can be attached specifically or non-specifically, and in either case, either ribosomes or mRNA templates can be immobilized.

For non-specific immobilization, the protein can be attached to a charged surface such as an aminopropylsilane-coated surface via electrostatic interaction, as described in 8. Ha, T. et al., (1996) *Proc. Natl. Acad. Sci. USA* 93, 6264-6268. Another nonspecific immobilization method successfully used for single-molecule fluorescence study is trapping molecules inside polyacrylamide pores (Dickson, R. M., et al., (1996) *Science* 274, 966-969) or agarose gel (Lu, H. P., et al., (1998) *Science* 282, 1877-1882., Dickson, R. M., et al., (1997) *Nature* 388, 355-358.). While gel immobilization has the merit of not requiring any special modification of the biomolecule, it has some disadvantages. First, the concentration of other small molecules such as enzyme substrates and ions is difficult to change in a short time. Sudden changes in the buffer conditions are necessary for a certain type of single-molecule studies. Second, because of limited molecular diffusion, it is not easy to study interactions between macromolecules in gel.

Specific immobilization requires a well-defined modification of the biological molecule. For instance, a biotin or a digoxigenin can be attached to an mRNA, rRNA or ribosomal protein, to immobilize them to streptavidin- or anti-digoxigenin-coated surfaces respectively. Alternatively, histidine tags that are typically introduced to help the purification of recombination proteins can be used to immobilize a ribosomal protein on a Ni-NTA-coated surface. A detailed procedure for preparing a mini-flow cell to immobilize biotinylated nucleic acids is described in Ha, T., *Methods* 25, 78-86 (2001).

A surface can be densely coated by polyethylene glycol (PEG). PEG is known to reject protein adsorption to a surface if it forms a dense coating. Bifunctional PEG can be used immobilize nucleic acids specifically to a surface while rejecting protein adsorption. mRNA can be optionally immobilized on a polyethylene glycol (PEG) coated surface with biotin-streptavidin linker, and the ribosomes allowed to process the immobilized mRNA. The mRNA preferably features 3'-end biotin labeling. Since protein synthesis may not end normally because of the linked 3' end, it is advisable to ensure that the template mRNA continues for at least 20 codons beyond the stop codon. In another approach, a ribosomal protein can be labeled with biotin and immobilized on a fused glass slide. The other ribosomal components can then be reconstituted around the immobilized protein. Ribosomal complexes can also be bound to a mica surface, which is transparent and flat on a molecular size scale. Ribosomes, either labeled or unlabeled, undergo binding to mica in a few seconds, allowing the detection of single fluorescence images in aqueous buffer. A large excess of ribosomes and a short incubation period are employed for single molecule detection. The mica-bound ribosomes retain their activities, as shown in Sytnik et al., *J. Mol. Biol.* (1999), 285, 49-54, where detailed protocols are provided. Preparation of the mica cells and adsorption of ribosomes to these cells is also described in Vanzi et al., Protein synthesis by single ribosomes, *RNA* (2003), 9:1174-1179.

M-RNA without Stop Codon

In one embodiment, the invention translates in a cell-free translation system a m-RNA encoding a protein or a portion of a protein (e.g., a host protein or a second protein, e.g., a protein implicated in a disease). In various embodiments, the m-RNA has been engineered such that it is missing a stop codon ("truncated m-RNA") relative to its full length sequence (FIG. 19). The absence of the stop codon allows the m-RNA to be fully translated into the corresponding protein, however, at the completion of translation, a member selected from the truncated m-RNA, the translated protein and both are retained on the ribosome that translates the protein. The introduction of deletions in nucleic acid sequences is a widely used method in molecular biology to study polypeptides encoded by the nucleic acid sequences and art-recognized methods of preparing such a truncated m-RNA are of use in practicing the present invention.

In an exemplary embodiment, the truncated m-RNA (FIG. 18) is transcribed from a DNA sequence in which the sequence coding the m-RNA stop coding is deleted (FIG. 17, FIG. 19a and FIG. 19b). Multiple procedures have been developed to generate deletions in nucleic acids, including procedures disclosed by Dunn et al. (U.S. Pat. Nos. 5,928,908; 5,968,768; and 6,248,569); Shen et al. (U.S. Pat. No. 5,356,773); Yohda et al. (*DNA Research*, 2: 175-181, 1995); Zhu and Marshall (*BioTechniques*, 18: 222-224, 1995); and Henikoff et al. (*Gene*, 28: 351-359, 1984 and U.S. Pat. No. 4,843,003). Other procedures for generating deletions have utilized variations of PCR (e.g., Pues et al., *Nucleic Acids Res.* 25: 1303-1304, 1997). All of the above are incorporated herein by reference in their entireties.

Viral Protein Expression and Capsid Assembly

The present invention also provides a method of expressing a host protein and a second protein, which may be a protein of interest (e.g., a protein implicated in a disease). The host protein and/or the second protein can be labeled with a detectable moiety when expressed using a composition of the invention. The second protein can be a protein from an infective agent, e.g., virus, bacterium a misfolded protein, etc. In an exemplary embodiment, the cell-free system is used to mimic capsid biogenesis and assembly and the second protein is one or more capsid protein. The focus on this embodiment is for purposes of illustration only and is not limiting.

In the cell-free system, viral capsid transcripts are translated in the presence of wheat germ extract that contains soluble factors necessary for capsid protein translation and subsequent capsid assembly (Lingappa et al. *J. Cell Biol* 136:567-581 (1997)). Both cytosolic and membrane proteins present in the wheat germ extract may be involved in capsid assembly and/or viral replication. Integral membrane proteins can include transmembrane proteins. In those embodiments utilizing viruses requiring membrane proteins for capsid assembly, appropriate membranes can be added to the cell-free translation mixture. It is further possible to supplement the cell-free translation mixture with other exogenous proteins, such as chaperone proteins that can for example, facilitate the assembly of capsid intermediates. Assembly of capsids in the cell-free system minimally requires expression of only the particular viral protein(s) that are involved in capsid assembly. Once expressed, polypeptides proceed to assemble into capsids that are catalyzed by host factors.

After incubation for a time sufficient to produce capsids, products of the cell-free reaction can be analyzed to determine sedimentation value, buoyant density, and electron microscopy appearance. Together these form a sensitive set of measurements for integrity of capsid formation.

Synthesized viral proteins can be detected in any manner known in the art. In an exemplary embodiment, the second protein or the host protein is labeled with a detectable moiety. In an exemplary embodiment, radiolabeled capsid polypeptides using labeled amino acids are used. In one embodiment using this approach, $^{35}$S methionine is added to the translation mixture. Following in vitro expression, velocity sedimentation gradients can generate fractions that are aliquoted into loading buffers and run on a standard SDS-PAGE gel. The gel can be exposed to film that generates autoradiographs showing the amount of $^{35}$S labeled viral protein in different fractions of the velocity sedimentation gradients. Alternatively, as is known in the art, a phosphoimager can be used to visualize radiolabeled viral proteins.

In various embodiments, antibodies, e.g., commercially available antibodies, are used to detect successful protein expression or capsid assembly. Alternatively, antibodies can be specifically raised against proteins of interest, as is well known in the art. Other detectable moieties, such as those set forth herein are of use as well.

Viral protein expression and capsid assembly in the cell-free system of the invention is useful for viruses from any family including, without limitation, Flaviviridae, Togaviridae, Bunyaviridae, Arenaviridae, Filoviridae, Poxviridae, Orthomyxoviridae, Rhabdoviridae, Herpesviridae, Coronaviridae, Paramyxoviridae, Hepadnaviridae, Bornaviridae, Picornaviridae, Retroviridae, Reoviridae, Papillomaviridae, Adenoviridae, Astroviridae, Polyomaviridae.

Non-viral Proteins

The present invention also provides a method of expressing non-viral proteins using a composition of the invention. In an exemplary embodiment, the cell-free system is used to mimic a pathway of assembling a multi-protein assembly for which the viral capsid serves as an analogous model. Because host proteins involved in viral capsid assembly also exist in the host for other purposes, the non-viral proteins that are the substrates for those endogenous assembly pathways are equally effectively usable for drug screening by the present invention. Thus, the present invention is applicable, not only to viral disease, but also to proteins implicated in other disorders including, but not limited to, metabolic, nervous system, oncologic, and immunologic diseases. In one embodiment, the invention is used to screen drugs effective in treating diseases in which amyloid fibrils are implicated (e.g., Alzheimer's and Creutzfeldt-Jakob disease). The present invention can be further used to mimic a bacterial or parasitic protein that forms a multiprotein complex that when disrupted, ameliorates bacterial or parasitic disease. What is required for applicability of the present invention is that the newly synthesized proteins in question share the ability to use other proteins in the extract to assist or facilitate their assembly into distinct multiprotein complexes.

Compositions, Kits and Integrated Systems

The invention provides compositions, kits and integrated systems for practicing the assays described herein. For example, an assay composition having a cell-free translation system including not more than about 5% wheat germ extract, and nucleic acid apparatus for expressing one or more host protein (e.g., a truncated m-RNA) a second protein and instructions for using these components in a drug screening assay are provided. Additional assay components as described above are also provided. For instance and affinity chromatography device, e.g., a solid support or substrate to which a candidate compound can be bound can also be included. Such solid supports include membranes (e.g., nitrocellulose or nylon), a microtiter dish (e.g., PVC, polypropylene, or polystyrene), a test tube (glass or plastic), a dipstick (e.g., glass, PVC, polypropylene, polystyrene, latex, and the like), a microcentrifuge tube, or a glass, silica, plastic, metallic or polymer bead or other substrate such as paper is provided. In various embodiments, the assay will use microtiter, e.g., 96, 384 or 1536 well microtiter plates. In various embodiments the affinity chromatography device is a resin column having a candidate compound immobilized thereon or a reactive group to which a candidate compound can be immobilized.

The invention also provides kits for practicing the candidate screening assays described above. The kits can include any of the materials noted above, and optionally further include additional components such as instructions to practice a high-throughput method of screening for a candidate compound, one or more containers or compartments (e.g., to hold candidate compounds, affinity chromatography resins, cell-free translation systems), a control activity modulator, a robotic armature for mixing kit components, and the like.

The invention also provides integrated systems for high throughput screening of potential candidate compounds. Such systems typically include a robotic armature which transfers fluid from a source to a destination, a controller which controls the robotic armature, a label detector, a data storage unit which records label detection, and an assay component such as a microtiter dish comprising a well having a capture moiety for a protein affixed to the well.

A number of well-known robotic systems have also been developed for solution phase chemistries. These systems include automated workstations like the automated synthesis apparatus developed by Takeda Chemical Industries, LTD (Osaka, Japan) and many robotic systems utilizing robotic arms (Zymate II, Zymark Corporation, Hopkinton, Mass; Orca, Hewlett-Packard, Palo Alto, Calif.) which mimic the manual synthetic operations performed by a chemist. Any of the above devices are suitable for use with the present invention. The nature and implementation of modifications to these devices (if any) so that they can operate as discussed herein will be apparent to persons skilled in the relevant art.

The following examples serve to further illustrate the present invention in a non-limiting manner.

EXAMPLES

Example 1

Compound resin conjugates are synthesized as follows:

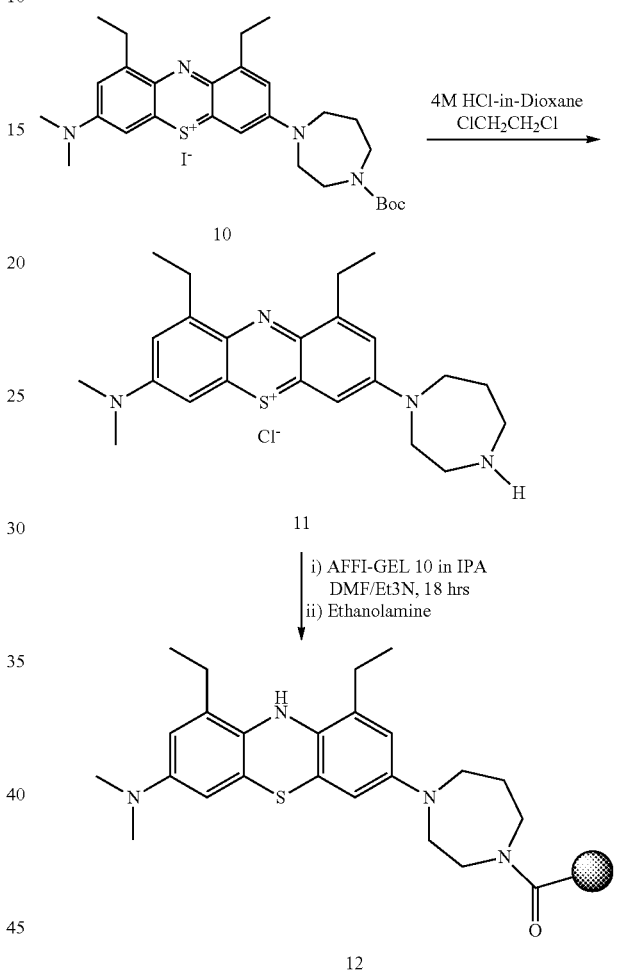

11 (64 mgs, 0.15 mmol) was obtained by the boc-deprotection of 10 employing 4M hydrochloric acid in dioxane and 1,2-dichloroethane. Upon completion, the reaction mixture was concentrated to dryness. To the residue obtained was added, DMF (1.5 mL), Et$_3$N (103 μL 0.75 mmol), AFFI-GEL® 10 (affinity media, AFFI-GEL is a trademark of Bio-Rad Laboratories, Inc.) (CHEM CAP: 0.015 mmol/mL, 20 mL, 0.30 mmol) and agitated for 18 hrs. Ethanolamine (10 mL) was added to the bluish mixture, agitated for an additional 10 hrs. The reaction mixture was filtered with the aid of a disposable filter funnel with polyethylene fitted disc, the resin was washed sequentially with DMSO (5×) solution of urea, isopropanol and stored in PBS, producing affinity chromatography device 12.

Materials and Methods

Cell-free translation was carried out essentially as described previously (Lingappa J-R, et al. (1994) A eukaryotic cytosolic chaperonin is associated with a high molecular weight intermediate in the assembly of hepatitis B virus capsid, a multimeric particle. *J Cell Biol* 125:99-111; Lingappa J-R, Hill R-L, Wong M-L, Hegde R-S (1997) A multistep, ATP-dependent pathway for assembly of human immunodeficiency virus capsids in a cell-free system. *J Cell Biol* 136:567-581), but at lower percentage cell extracts.

Moderate throughput small molecule screening was carried out in 384 well format by translation of RABV N mRNA supplemented with mRNA for RABV P and M, and eGFP in 20 µl reactions per well in the presence of small molecules from the Prosetta compound collection, for 1 hr at 26° C. for synthesis, followed by assembly at 34° C./1 h. Products were captured on a second 384 well plate precoated with affinity purified antibody followed by washing with phosphate buffered saline containing 1% TRITON™ x-100 (detergent, TRITON is a trademark of Dow Chemical Company), and then decorated with biotinylated affinity purified antibody, neutravidin HRP, further washing and incubation with a fluorogenic substrate, QUANTABLU™, (fluorescence kit, QUANTABLU is a trademark of Life Technologies), that generates a fluorescent readout proportional to the degree of biotinylated antibody binding which in turn is a function of degree of assembly upon measurement of fluorescence at 330/425 nm (excitation/emission) after 1 hr.

Sucrose step gradients were performed essentially as described previously (Lingappa J-R, et al. (1994) A eukaryotic cytosolic chaperonin is associated with a high molecular weight intermediate in the assembly of hepatitis B virus capsid, a multimeric particle. *J Cell Biol* 125:99-111; Lingappa J-R, Hill R-L, Wong M-L, Hegde R-S (1997) A multistep, ATP-dependent pathway for assembly of human immunodeficiency virus capsids in a cell-free system. *J Cell Biol* 136:567-581).

Glycerol gradients were poured using a linear gradient former from 5 to 35% glycerol in Tea 10 mM pH 7.6, 10 mM NaCl, 1 mM MgAc and 0.2 mM EDTA. Gradients were chilled, samples up to 200 ul loaded and centrifuged in the TLS-55 rotor at 50K rpm/55 minutes with slow acceleration and deceleration. Gradients were then fractionated into 200 ul aliquots 1-11 and aliquots analyzed by SDS-PAGE.

Western Blotting

SDS-PAGE was carried out as previously described (Lingappa J-R, et al. (1994) A eukaryotic cytosolic chaperonin is associated with a high molecular weight intermediate in the assembly of hepatitis B virus capsid, a multimeric particle. *J Cell Biol* 125:99-111; Lingappa J-R, Hill R-L, Wong M-L, Hegde R-S (1997) A multistep, ATP-dependent pathway for assembly of human immunodeficiency virus capsids in a cell-free system. *J Cell Biol* 136:567-581). Gels were transferred in Towbin buffer overnight, blocked in 1% BSA, and incubated at room temperature in primary antibody at 1:1000 dilution of approximately 100 µg/ml affinity purified IgG for 1 hr, washed 3× in PBS with 0.1% TWEEN™-20 (detergent, TWEEN is a trademark of Croda International) and incubated with secondary anti-rabbit antibody coupled to alkaline phosphatase at 1:5000 dilution for 1 hr, followed by washing to various degrees of stringency by elevation of salt, followed by Tris-buffered saline wash and incubation in developer solution prepared as follows. BCIP [5-Bromo-4-chloro-3-indolyl phosphate] 225 mg was dissolved in 18 ml dimethyl formamide [DMF] with 12 ml water to give 7.5 mg/ml in 60% DMF. NBT [Nitro blue tetrazolium] 450 mg dissolved in 21 ml dimethyl formamide with 9 ml water was prepared (15 mg/ml 70% DMF). (100 µl of each solution (stored at −20° C.) was adjusted to 50 ml with 0.1M Tris pH 9.5/0.1 mM MgCl2 to prepare working stock of developer that was applied to washed blots.

Cells and Virus

Street Rabies virus (RABV; TxFX A11-1198) was derived from the salivary glands of a rabid gray fox (*Urocyon cinereoargenteus*), associated with enzootics in carnivores throughout the southwest United States. Mouse neuroblastoma (MNA) cells were propagated in Eagle minimal essential medium (MEM) supplemented with 10% fetal bovine serum.

RABV Growth in MNA Cells.

In multiple wells of a 96-well plate, MNA cells were infected with RABV at a multiplicity of infection (m.o.i) of 0.1 per cell (except cell control), and incubated at 37° C. for 48 hrs in the presence of MEM supplemented with 10% fetal calf serum. After incubation, 100 µl of supernatant was removed from each well, and replaced with an anti-viral compound at described concentrations, and incubated for an additional 48 hrs.

RABV Infectivity Titration

After incubation, 100 µl of supernatant was removed and titrated on MNA. Micro titer plates were washed twice in PBS (phosphate buffered saline, pH 7.2-7.4) and fixed with 80% acetone at −20° C. RABV antigens were detected by direct fluorescent antibody staining using fluorescein isothiocyanate (FITC)-labeled monoclonal antibody conjugate (Fujirebio Diagnostics, Inc., Malvern, Pa.), titers for infectious virus released into the supernatant were calculated by the Reed and Muench method. The BSR cells (a clone of BHK) were grown in Dulbecco's minimal essential medium (DMEM) supplemented with 10% fetal bovine serum (Atlanta Biologicals, Lawrenceville, Ga.) at 37° C., in a 5% $CO_2$ incubator. The rabies virus ERA strain was obtained from ATCC and maintained at CDC, Atlanta. For virus titration and antiviral compound treatment, the confluent BSR cells in T75 flasks were split and seeded to the 24-well-plate (Fisher Scientific, Becton-Dickinson, Suwanee, Ga.). Twenty four hours post-incubation, the confluent BSR cells in plate were infected with 1 m.o.i. of rabies virus ERA either pre- or post-antiviral compound treatment at the indicated time course. Virus titer in the treated cell supernatants was calculated in focus forming unit (ffu) per ml. In brief, 20 µl of cell supernatants, mixed with freshly prepared 180 µl of BSR cell suspension, was seeded into a LAB-TEK® Chamber Slide (laboratory equipment, LAB-TEK is a trademark of Nalge Nunc International Corp.) (Fisher Scientific, Nunc, Rochester, N.Y.). A serial 10-fold dilution of the virus-cell supernatants was made similarly with BSR cell suspensions in the same slide. The cells were incubated at 37° C., in a 5% CO2 incubator for 24 hrs before titration using the DFA assay. A standard DFA protocol (cdc.gov/rabies/pdf/rabiesdfaspv2.pdf) was followed for virus titration or the effect of antiviral compound treatment against the original cells grown in the 24-well-plate.

Materials were general purchased from Sigma Chemical Co, St Louis, Mo. or Thermo Fisher. Affinity purified antibody to RABV N and ABCE1 can be purchased from pbpl.com.

Results

As a first step to application of this novel approach, we analyzed authentic RABV, that had been irradiated to render the virus non-infectious, on sucrose step gradients (ssg) that have previously been the used to dissect the capsid assembly pathways of other viral families in cell-free systems (Lingappa J-R, et al. (1994) A eukaryotic cytosolic chaperonin is associated with a high molecular weight intermediate in the assembly of hepatitis B virus capsid, a multimeric particle. *J Cell Biol* 125:99-111; Lingappa J-R, Hill R-L, Wong M-L, Hegde R-S (1997) A multistep, ATP-dependent pathway for assembly of human immunodeficiency virus capsids in a cell-free system. *J Cell Biol* 136:567-581; Klein K-C, Dellos S-R, Lingappa J-R (2005) Identification of residues in the hepatitis C virus core protein that are critical for capsid assembly in a cell-free system. *J Virol.* 79:6814-6826; Klein K-C, Polyak S-J, Lingappa J-R (2004) Unique features of hepatitis C virus capsid formation revealed by de novo cell-free assembly. *J Virol.* 78:9257-9269). As shown in FIG. 3A, when authentic RABV, irradiated to render it non-infectious, is solubilized in non-denaturing detergent (e.g. TRITON™ x-100 (detergent, TRITON is a trademark of Dow Chemical Company)), and analyzed in a manner analogous to that described previously (Lingappa J-R, et al. (1994) A eukaryotic cytosolic chaperonin is associated with a high molecular weight intermediate in the assembly of hepatitis B virus capsid, a multimeric particle. *J Cell Biol* 125:99-111), with the RABV nucleoprotein (N) gene product visualized by Western Blot (WB), approximately 80% of the material found is in a broad region peaking in fraction 4. This was used as a reference for subsequent cell-free studies and for validation of the screen to be established.

Our approach to expression through cfps is to first engineer the coding region of interest, in this case the RABV N gene initially, and later the matrix (M) and phosphoprotein (P) genes, behind the SP6 bacteriophage promoter and the *Xenopus* globin 5' untranslated region, as described previously (Krieg P-A, Melton D-A (1984) Functional messenger RNAs are produced by SP6 in vitro transcription of cloned cDNAs. *Nucleic Acids Res* 12:7057-7070). PCR is then used to generate messenger RNA (mRNA) encoding each full-length protein of interest. FIG. 3B displays the autoradiogram of 35S radiolabelled translation products of the N, M and P genes of RABV, individually and when co-expressed, in the 35S Translabel-supplemented WG cfps system, as analyzed by polyacrylamide gel electrophoresis in sodium dodecyl sulfate (SDS-PAGE).

When mRNA encoding N was translated at 26° C./1 hr and applied to ssg as described, the newly synthesized (as evidenced by radiolabelling) protein is released from the ribosome and found at the top of the ssg with peak in fraction 1 (FIG. 3C left panel), with poor progression upon continued incubation at that temperature (data not shown). However, with further incubation at 34° C., the peak was observed to advance into the gradient as a function of incubation time, culminating in a new peak in fractions 5-7 (FIG. 3C panels 2nd and 3rd from left). When brain post mitochondrial supernatant (brpmis) was added immediately after synthesis (e.g. after 26° C./1 h), and incubation continued at 34° C. followed by subsequent ssg analysis, formation of the peak in fractions 5-7 was enhanced (FIG. 3C 4th panel from left). When apyrase (an enzyme that hydrolyzes ATP) was added instead of brpmis, a very different complex with a broad peak in fractions 7-9 was observed, upon incubation at 34° C. Analysis immediately after incubation with apyrase at 4° C./1 h revealed no change from FIG. 3C left panel (data not shown). That is, the shift in size to the middle of the ssg was observed only after the subsequent 34° C. incubation step. The results shown in FIG. 3C suggest the existence of a series of putative assembly intermediates culminating in fractions 5-7. The change in migration upon incubation at 34° C. after apyrase-treatment suggests either that one of the intermediates is dependent on metabolic energy, or that in the absence of metabolic energy "off-pathway" interactions occur, giving rise to different complexes of higher molecular mass. The results of adding brpmis suggests machinery needed to form the complexes observed in fractions 5-7 is present in brain, a tissue expected to have machinery that would facilitate RABV production, given that RABV is a neurotropic virus (Rabies (2009) in Vaccines for Biodefense and Emerging and Neglected Diseases, eds Barrett A, Stanberry L (Academic Press), pp 605-627).

RABV P and M Alter Flux Through the Putative RABV N Assembly Pathway

The rabies literature suggests that the M and P proteins are likely to play roles in assembly of progeny virus (Fu Z-F, Zheng Y, Wunner W-H, Koprowski H, Dietzschold B (1994) Both the N- and the C-terminal domains of the nominal phosphoprotein of rabies virus are involved in binding to the nucleoprotein. *Virology* 200:590-597; Yang J, et al. (1998) The specificity of rabies virus RNA encapsidation by nucleoprotein. *Virology* 242:107-117; Waibler Z, Detje C-N, Bell J-C, Kalinke U (2007) Matrix protein mediated shutdown of host cell metabolism limits vesicular stomatitis virus-induced interferon-alpha responses to plasmacytoid dendritic cells. *Immunobiology* 212:887-894; Gerard F-C, et al. (2009) Modular organization of rabies virus phosphoprotein. *J Mol Biol* 388:978-996). In view of this possibility, we co-translated mRNA encoding N with those encoding P and M as in FIG. 3B, and analyzed the products over time in ssg as described. We established that synthesis is fully achieved at 22° C. for 90 minutes, in distinguishable from that achieved at 26° C. for 1 hr, but that at the lower temperature the blockade on high molecular weight complex formation is complete, allowing for more precise staging of putative RABV capsid assembly intermediate progression (data not shown). Likewise, we established that, like HCV (Klein K-C, Dellos S-R, Lingappa J-R (2005) Identification of residues in the hepatitis C virus core protein that are critical for capsid assembly in a cell-free system. *J Virol.* 79:6814-6826) but unlike HBV (Lingappa J-R, et al. (1994) A eukaryotic cytosolic chaperonin is associated with a high molecular weight intermediate in the assembly of hepatitis B virus capsid, a multimeric particle. *J Cell Biol* 125:99-111) or HIV (Lingappa J-R, Hill R-L, Wong M-L, Hegde R-S (1997) A multistep, ATP-dependent pathway for assembly of human immunodeficiency virus capsids in a cell-free system. *J Cell Biol* 136:567-581), putative RABV capsid formation was independent of nascent chain concentration. That is, 5× and 25× dilution of RABV transcripts with mock transcription reaction, with corresponding diminution of the intensity of the radiolabelled protein bands upon translation, resulted in no diminution in the percentage of N assembled into high molecular weight complexes in fractions 5-7, compared to that observed with undiluted transcript (data not shown). Addition of TRITON™ x-100 (detergent, TRITON is a trademark of Dow Chemical Company) to a final concentration of 1% also did not impair assembly (data not shown), unlike what has been observed for HIV capsid formation (Lingappa J-R, Hill R-L, Wong M-L, Hegde R-S (1997) A multistep, ATP-dependent pathway for assembly of human immunodeficiency virus capsids in a cell-free system. *J Cell Biol* 136:567-581). For subsequent analysis, mRNAs encoding these three RABV genes were translated at 22° C., with assembly-related manipulations occurring at 34° C.

A Pathway by which RABV N Enters High Molecular Weight Complexes

Compared to parallel experiments with N translation alone, the results for N co-translated with M and P were notable for a striking slowing of N progression to fractions 5-7 (see FIG. 3D). Thus, after 34° C./1 hr, approximately 17.5% of N instead of 38% was found in those fractions. After 34° C./2 hrs, 20% of N instead of 27% was in fraction 5-7. However upon addition of brpmis, the percentage of assembly after just one hour at 34° C. was 35%, suggesting that the stimulation of assembly observed with brpmis was maintained, and indeed enhanced, in the presence of all three newly synthesized RABV gene products compared to N alone. The effect of the M and P gene products on N assembly appears to occur post-translationally, as the products can be synthesized separately at 22° C. and then combined without a change in the pathway observed, upon incubation at 34° C. (data not shown). Thus, regardless of whether they were co-translated with N or added immediately after synthesis, the effect of newly synthesized RABV M and P gene products suggested a more ordered and therefore complete progression to the distinctive complex migrating in fraction 5-7, perhaps by preventing off-pathway interaction.

Multiple Putative RABV Assembly Intermediates

Figure 3D:
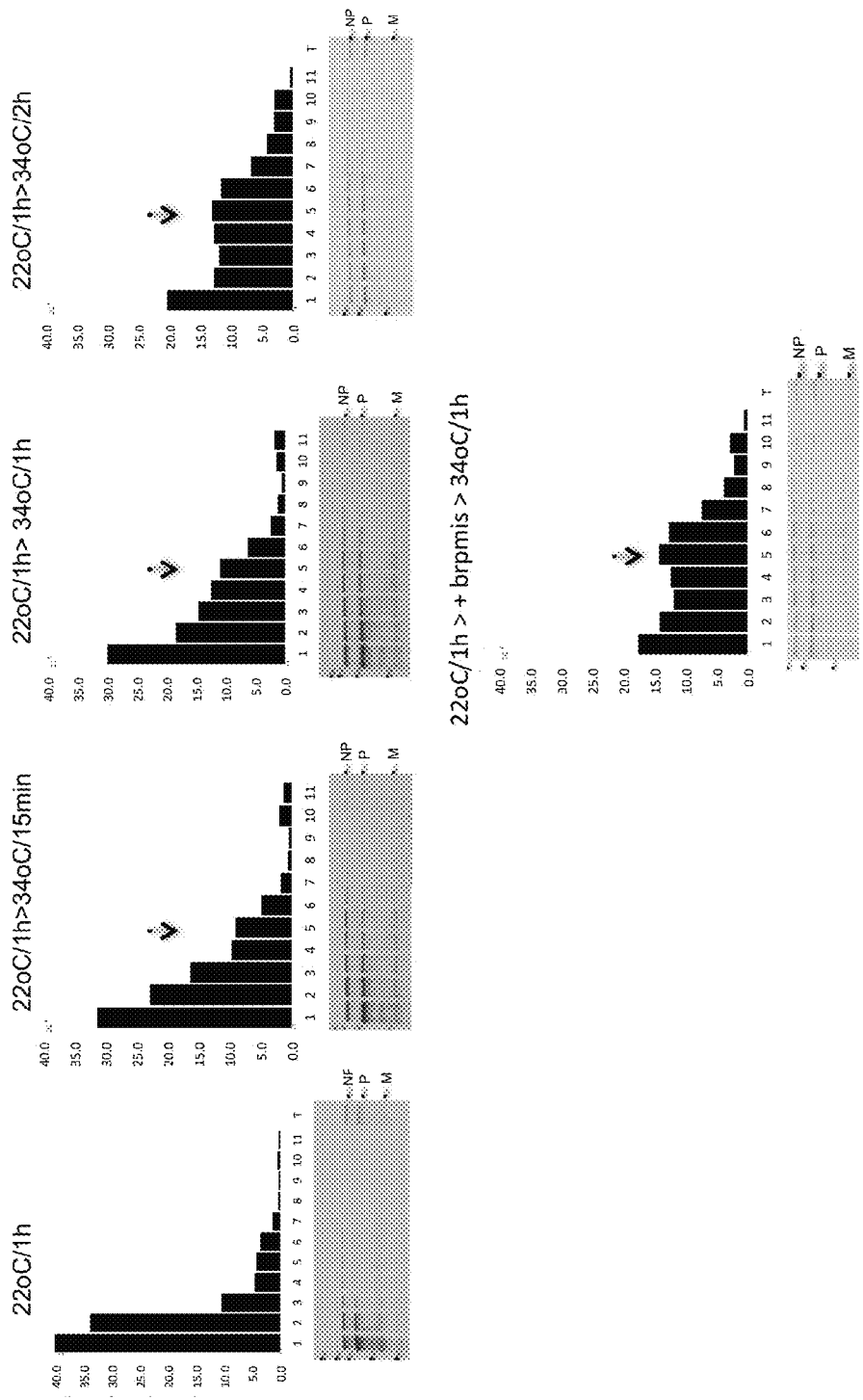

To better catalogue the high molecular weight complexes observed for RABV N, gradient fractions were analyzed under conditions that generated a distribution of N between fractions 1-6 (e.g. as shown in FIG. 3D, right hand panel). First determined was whether, when individual gradient fractions are diluted and reanalyzed by ssg, they behave as in the original ssg analysis. FIG. 4A demonstrates fraction-specific distinctive ssg rerun behavior. Fractions 1 and 2 run predominantly in the same fraction on rerun. Modest spillover into the next fraction is likely to be due to the fact that the diluted sample load was equivalent to the fractions taken (200 ul). Rerun fraction 3 appears to be distributed roughly equally between fractions 1-4. Rerun of fraction 4 gave a striking peak in fraction 4, with little material progressing further, suggesting a structure with distinctive properties from those in other fractions. Fractions 5 and 6 appeared to distribute predominantly within fractions 5-7. That individual fractions could be diluted and rerun reproducibly with these striking phenotypes, suggests they represent at least two and possibly as many as four distinct complexes (fractions ½, fraction 3, fraction 4, and fraction 5-7). To further explore the possibility that these complexes were intermediates on the path to fractions 5-7, the isolated gradient fractions were incubated with either buffer alone (FIG. 4B), with WG extract and ATP, GTP and an energy regenerating system (termed energy, FIG. 4C) or with energy in the absence of WG extract (FIG. 4D). All fractions advance to fractions 5-7 after incubation at 34° C./2 h, but only when both energy and WG were provided. In the absence of WG, fractions 1-3 behave indistinguishably from incubation with buffer alone and are largely unchanged. However this includes the curious behavior of fraction 3 move in almost equal measure to fractions 3 and 4. The highly distinctive peak in fraction 4 moves notably with energy and without WG to an equally distinctive fraction 5, phenotypically different from the fraction 5-7 endpoint peak observed at steady state. These findings suggest that each complex has distinctive properties with respect to dependence on soluble versus bound factors, energy dependence, and reversibility. Most likely these complexes include bona fide assembly intermediates on a pathway culminating in the broad peak seen in fractions 5-7, although these may be co-mingled with off-pathway complexes. A means of distinguishing on and off pathway complexes is needed, and will be addressed shortly.

Energy-dependence of the Putative RABV Assembly Pathway

In this context, we addressed in more detail for the specific case of RABV, the critical issue of energy-dependence, a key discriminator between spontaneous, thermodynamically driven self-assembly and (host) catalyzed models of capsid formation, as has previously been done for HIV (Lingappa J-R, Hill R-L, Wong M-L, Hegde R-S (1997) A multistep, ATP-dependent pathway for assembly of human immunodeficiency virus capsids in a cell-free system. *J Cell Biol* 136:567-581). Apyrase was immobilized on sepharose beads and the immobilized apyrase (iapy) demonstrated to be active and to fully deplete the ATP in 25 bed volumes of translation reaction, and that no apyrase leached from the beads since it could be quantitatively removable by centrifugation with restoration of translation upon addition of fresh ATP (data not shown). Translation products of mRNAs encoding each of RABV proteins N, M, and P, were synthesized separately or together and immediately post-translationally, iapy was added and incubated at 4° C. for 1 hr, and then the iapy removed by centrifugation, with careful transfer of the supernatant. An aliquot of the supernatant was analyzed without further manipulation as for FIG. 3D left panel, and confirmed that essentially all RABV N was still found in fractions 1 and 2, even after hydrolysis of all ATP by iapy and its subsequent removal (data not shown). Thus, the simple act of ATP depletion did not alter the position of RABV N-containing structures on ssg. Additional aliquots were then analyzed after incubation at 34° C./2 hrs either with no additions, after addition of energy, or addition of a nonhydrolysable ATP analog (AMPPNP). After iapy treatment, which depletes ATP, but does not result in a detectable change in assembly state, incubation at 34° C. with no additions resulted in a striking smear of N in high molecular structures in fractions 7-9 (FIG. 5, left panel). This pattern was reminiscent of that observed with apyrase treatment in FIG. 3C. Addition of the non-hydrolyzable analog AMPPNP also resulted in the high molecular weight smear infractions 7-9 (FIG. 5, right panel). In contrast, incubation with energy resulted in appearance of the distinctive peak in fractions 5-7 (FIG. 5, middle panel). Thus, the patterns after incubation of energy-depleted products either in the absence of added energy or supplemented with the non-hydrolysable ATP analog were similar and distinctively different from that observed upon supplementation with energy, which resulted in complexes that appear to be on the previously identified assembly pathway. Taken together, these experiments strongly suggest the occurrence of an energy-dependent step in formation of the distinctive high molecular weight RABV N-containing complex observed in fraction 5-7 on ssg in FIG. 3D.

Co-immunoprecipitation of RABV N and P in Assembly Intermediates

To assess the composition and significance of these putative assembly intermediates, and to provide another set of properties by which they could be distinguished, individual fractions from ssgs containing RABV N, as shown in FIG. 3D after assembly at 34° C./2 h or with brpmis after 34° C./1 h, were probed with affinity purified antibodies (Gerard F-C, et al. (2009) Modular organization of rabies virus phosphoprotein. *J Mol Biol* 388:978-996) raised to a discrete epitope (aa 359-384, see legend to FIG. 6) that is exposed on the surface of mature RABV N ((1998) Antibodies: a Laboratory Manual, eds Harlow E, Lane D (Cold Spring Harbor Laboratory Publications), pp 139-243). This experiment allowed us to assess not only epitope accessibility from one putative assembly intermediate to another, but also whether there was co-precipitation of RABV P or M with N. As can be seen in FIG. 6B top panel, striking co-association of N with P is observed, particularly for fractions 1-4, compared to total N (bottom panel). However no association between N and M could be demonstrated, despite the fact that a fraction of M was seen to comigrate with N and P in the position of the most advanced assembly complex, namely fractions 5-7 (data not shown). One striking observation is that the association of P with N was greatest in fraction 1 and paralleled association of N with anti-N which in turn did not correlate with the amount of total N present in the fraction. The simplest interpretation of this result is that either the N-P association occurs very early and N in advanced complexes is poorly accessible to anti-N (e.g. due to the presence of host proteins), or the association of N with P is indirect via binding of both proteins by host protein complexes rather than to each other. Regardless, the co-immunoprecipitation of P with N by anti-N clearly reveals distinct differences in accessibility of N from one assembly intermediate to another. In all cases identical aliquots of each fraction were precipitated with affinity purified irrelevant antibody as a control, and only trace residual N or P bands were observed to be present (data not shown).

In FIG. 6C, the same fractions were probed with affinity-purified antibody to a C-terminal epitope of ABCE1, a host protein previously implicated in HIV capsid assembly (Lingappa J-R, Hill R-L, Wong M-L, Hegde R-S (1997) A multistep, ATP-dependent pathway for assembly of human immunodeficiency virus capsids in a cell-free system. *J Cell Biol* 136:567-581; Zimmerman C, et al. (2002) Identification of a host protein essential for assembly of immature HIV-1 capsids. *Nature* 415:88-92). Progressively more P and to a lesser extent, N are co-immunoprecipitated by anti-ABCE1 from fractions 1-4. In the particular experiment shown, assembly proceeded relatively further to the fraction 5-7 endpoint and as a result, relatively little N is present in fraction 4. Yet, by co-immunoprecipitation with anti-ABCE1, fraction 4 shows the greatest immunoprecipitated band intensity for both N and P. A striking co-association of RABV P with ABCE1 was observed in all fractions, while RABV N was co-immunoprecipitated particularly well in fraction 4, but not significantly in fraction 1. For each panel of FIGS. 6B and C, the autoradiogram from which the quantitated bands were derived is shown to the right. For each fraction, 100 fold molar excess of the ABCE1 or RABV N peptides with which the rabbits were immunized is shown to completely abolish immunoprecipitation or co-immunoprecipitation of N and P, demonstrating the specificity of the association observed. In all cases no significant binding was observed to irrelevant affinity purified antibody (data not shown). These data suggest that N and P co-associate, directly or indirectly, after synthesis, that ABCE1 is associated with RABV P in all assembly intermediates and with RABV N in selected intermediates, particularly that represented by fractions 4. Interestingly, no co-association of ABCE1 with either RABV N or P was observed in the high molecular weight (fractions 7-9) material observed after depletion of energy using iapy as shown in FIG. 5 (data not shown), consistent with the hypothesis that those complexes are "off pathway" associations occurring in the energy-depleted state. Furthermore, no ABCE1 is observed by WB of authentic RABV capsids as generated by ssg analysis (data not shown). These data suggest that, as for HIV capsid assembly, ABCE1 is also associated with putative RABV N-containing assembly intermediates, but not with the assembled capsid.

Development of a Whole Pathway Drug Screen

We wished to establish a screen to identify small molecules capable of blocking or altering progression through this newly identified pathway, through their effect on the catalytic protein-protein interactions implied by the data in FIG. 3-6. If such compounds could be found, and if they were effective against infectious RABV, that would greatly strengthen the suggestive evidence for this pathway. It would also establish the relevance of the pathway as identified in cfps to authentic RABV-host interactions. Thirdly, it would provide a powerful new set of tools for identifying the host proteins involved, and dissecting their mechanism and time of action. The host proteins were suspected to be highly unconventional targets, therefore we chose not to establish a target specific screen (e.g. focused on a specific host protein), or even to try and identify the target at the outset. Instead, we took advantage of the fact that the cfps system readily achieved high molecular weight structures likely to include multimerization of RABV N, as demonstrated. Thus we devised instead a whole pathway screen that monitored the ability to assemble the "on pathway" high molecular weight structures (FIG. 7A). Hits in such a screen might encompass many targets at many steps within the pathway, but any and all of them would be of interest. We suspected that catalytic targets would likely provide the greatest dynamic range and therefore would give the most robust readout.

The screen was validated by demonstrating that authentic RABV shown in FIG. 3A can be detected across the sucrose gradient after treatment with TRITON™ x-100 (detergent, TRITON is a trademark of Dow Chemical Company) to 1% to solubilize the envelope, and high salt, to expose the epitope on N (data not shown). Likewise, putative assembly intermediates generated in the cfps programmed with RABV N with or without RABV M and P mRNAs could be detected across ssg (data not shown). For the actual small molecule screen, translation was initiated in a separate 384 well plate in 20 µl volumes of a modified WG extract (Lingappa J-R, et al. (1994) A eukaryotic cytosolic chaperonin is associated with a high molecular weight intermediate in the assembly of hepatitis B virus capsid, a multimeric particle. *J Cell Biol* 125:99-111), only in this case programmed with RABV N, M, and P mRNAs. After synthesis and post-translational maturation at 34° C. as demonstrated in FIG. 3, translation products were transferred to a second antibody coated plate, captured, washed, and the captured products (synthesized in the presence of various compounds) decorated with a biotinylated version of the same affinity purified anti-N peptide-specific antibody that had been used for capture. After subsequent washing, a fluorescence signal was generated by addition of neutravidin horseradish peroxidase (NHRP) that bound to the biotinylated antibody and after washing converted a fluorogenic substrate (QUANTABLU™, (fluorescence kit, QUANTABLU is a trademark of Life Technologies)) with measurement of relative fluorescence units (RFUs). The fluorescence readout was shown to be dependent on translation of RABV N and linear as a function of translation titration (data not shown).

We sought hits by screening a portion of a library of drug-like small molecules largely conforming to Lipinski's rule of five (Albertini A-A, et al. (2006) Crystal structure of the rabies virus nucleoprotein-RNA complex. *Science* 313: 360-3). Hits were defined as compounds demonstrating a dose-dependent diminution of fluorescence in the whole pathway screen where the diminution of fluorescence could not be accounted for by diminution of protein synthesis (as measured by co-translation of green fluorescent protein [eGFP] or by WB for RABV N). A number of compounds were observed to have modest dose-dependent inhibition of fluorescence in the RABV screen. A potent compound emerging from a comparable screen for influenza nucleoprotein assembly had no effect in the RABV screen (data not shown). Two hits and one negative compound from the RABV screen are shown in FIG. 7B. A set of compounds including these three was assessed for activity against infectious RABV in Vero cells. Modest activity of the two active compounds was observed, and confirmed against a strain of "street rabies" isolated from a grey fox (FIG. 7C).

Robust SAR Displayed by an Anti-RABV Pharmacophore

A set of analogs of one of the two active compounds were synthesized and assessed in both the cfps screen (FIG. 8A), and against infectious RABV in Vero cells (FIG. 8B), as assessed by TCID50 of the medium (top panel), and by direct fluorescent antibody (DFA) assay of the cells in the primary infection plate (bottom panel). One of the compounds, A, that showed striking dose-dependent titration of RABV, was chosen for further study. Note that the two compounds on the left of FIG. 8A were inactive in both the cfps screen and against infectious RABV even at 50 µM, and the activity in the screen roughly corresponded to the degree of activity observed against infectious RABV. Thus we have achieved an effective cfps-based screen: active compounds from that screen have been validated as active against infectious RABV in cell culture. Moreover, at least one of the initial two active compounds displays a robust SAR, suggesting it to be an excellent starting point for anti-RABV drug discovery. Analog A (FIG. 8D) had an EC99 against infectious RABV in Vero cell culture of approximately 200 nM and was chosen for further study. When assessed for toxicity in Vero cells using the quantified resasurin reduction assay (ALAMARBLUE® (cell viability reagent, ALAMARBLUE is a trademark of Life Technologies), see ref 39), this compound was found to have a CC50 of approximately 2.5-10 µM. Thus the selectivity index (SI) or CC50/EC50 of this compound was found to be >50. While other analogs such as E and F were more potent than A against infectious RABV in cells, they were also more toxic and therefore had a lower SI.

Time of Addition of A to Cells Infected with RABV

It was hypothesized that the most robust hits from this screen are likely to be targeting those host factors that act catalytically, as the consequence of inhibition of such a target would be expected to have the greatest effect on RABV N assembly in cells. The potent compounds identified made it possible to test this hypothesis. First compared was the effect of time of compound addition on the titer of infectious RABV generated in infected cells. In the experiments shown in FIG. 8B, compound had been added within one hour after addition of virus (e.g. essentially immediately after infection). If addition of drug was delayed, one might expect to see a drop in efficacy of the drug as the window of time of drug action is during capsid protein synthesis and assembly. Indeed, as shown in FIG. 9 for both A and an analog of a different pharmacophore lead series emerging from H, each with a distinctive dose-response curve, infectivity in the medium 72 hrs after infection went from undetectable at drug addition times up to 6 hrs after infection to a plateau of approximately 105 focus forming unit (ffu)/ml from 12 or 24 hrs post infection onwards. A similar phenomenon was observed for the original infection plate (assessed by DFA, FIG. 9B). These findings suggest two things: first, the drug does not act directly on the virus. If it did, then infectivity should have been equally eliminated regardless of time of addition over the first 48 hrs of the 72 hrs time-course, as the drug would have the opportunity to act on the virus in the medium for an extended period of time prior to harvest of that medium for TCID50; second, the striking difference between drug action at early versus later times after infection, for both compounds, suggests that an intracellular step in the viral lifecycle was critical for drug action. This would be consistent with action on host targets such as those of the proposed host-catalyzed capsid assembly pathway.

Dissection of the Time of Action of A During Cfps

To better understand the time of action and target of these drugs, studies were performed in the cfps system. By generating mRNA for RABV N from which a stop codon is lacking (Perara E, Rothman R-E, Lingappa V-R (1986) Uncoupling translocation from translation: implications for transport of proteins across membranes. Science 232:348-352), termed truncated N and abbreviated NR, it is possible to retain a significant fraction of chains in polyribosomes, such that they migrate in the middle of the ssg (FIG. 10 left panel). Upon treatment with the aminoacyl tRNA analog puromycin, NR chains would be released from polyribosomes, and upon subsequent ssg analysis, should be found at the top of the gradient (Sumantran V-N (2011) Cellular chemosensitivity assays: an overview. Methods Mol Biol 731:219-236). However, based on the analysis in FIGS. 3C and D, these released chains should not proceed to assemble in the cfps system unless incubation is carried out at 34° C. This expectation was confirmed (FIG. 10B), and upon subsequent incubation at 34° C., the RABV N chains proceed through the putative assembly pathway, including fractions 2-6 (FIG. 10C), as described earlier. This protocol allows us to stage the addition of compound to determine when the target has consummated its role in the capsid assembly process. Once the target's action is complete, addition of the compound would be expected to have no further effect on RABV N multimerization as monitored by the fluorescence readout of the cfps screen described in FIG. 7. In FIG. 11, the effect of translating RABV NR together with RABV M and P, followed by treatment with A at 26° C./30 followed by puromycin at 26° C./30 minutes versus reversed treatment with puromycin first and then 30 minutes later treating with compound, was assessed. On the left is the effect of A added before puromycin treatment, demonstrating dose-dependent titration in fluorescence as demonstrated previously co-translationally. In the middle panel is the result of treating with puromycin first and 30 minutes later adding A. As can be seen, the compound effect is completely absent when added after puromycin release. Additional controls demonstrate that the dose-dependent titration of RABV N RFUs by A was dependent on the subsequent events of assembly. Thus, either treatment with apy (FIG. 11C) or omission of the 34° C. incubation step (data not shown), were sufficient to abolish the titration of RFUs observed by A under standard assembly conditions (9B).

This data strongly suggests that the target protein action blocked by the compound occurs very early in the pathway, possibly before release of newly synthesized RABV N from the ribosome. And yet, the compound effect requires the later events of assembly (incubation at 34° C.), to be manifest. Indeed, a time course of A addition at 1, 5, and 15 minutes after puromycin release, strongly suggests that the target is engaged and has completed its action prior to release of the nascent chain, because even 1 minute after treatment with puromycin, the drug effect is largely lost (data not shown).

Affinity Chromatography with Immobilized K for Target Identification

As an approach to better understanding this unconventional target, A was coupled to a resin, and the resulting resin conjugate used for affinity chromatography (Blobel G, Sabatini D (1971) Dissociation of mammalian polyribosomes into subunits by puromycin. Proc Natl Acad Sci USA 68:390-394). The resin conjugate corresponding to A was termed resin 1 and blocked resin alone (lacking a compound and therefore serving as a negative control for binding specificity) was termed resin 2. In FIG. 12A, authentic irradiated RABV as shown in FIG. 3A was treated with TRITON™ x-100 (detergent, TRITON is a trademark of Dow Chemical Company) to solubilize the envelope and release the capsid, and then applied to columns of resins 1 and 2. Flow-through was collected, the columns washed with 50 bed volumes of 1% TRITON™ x-100 (detergent, TRITON is a trademark of Dow Chemical Company)-containing buffer, and the washed resin conjugates were incubated with free compound A at 200 µM in buffer for 1 hr serially twice and then overnight, to elute bound proteins, with the eluate collected and analyzed by WB. An aliquot of the starting material was serially diluted and analyzed in parallel. As shown in FIG. 12A, 0.1% of the loaded sample could be readily detected by WB. RABV N in the resin 1 free compound eluate was below this level and was slightly less than RABV N in the control resin 2 free compound eluate. Thus, there was no specific binding of authentic RABV capsids to the resin adduct of the compound A highly potent against infectious RABV. These data reinforce the earlier conclusion (see FIG. 9) that the drug target appears not to be present in authentic RABV.

Reconstitution of Compound Sensitivity with Column 1 Free Compound Eluate

The most direct test of a host target would be to demonstrate binding of specific protein(s) from the cfps extract prior to its programming with RABV N encoding mRNA—and to show the bound proteins are essential for the activity of A. All the more because A, the active anti-RABV compound, was identified through the cfps screen and used as the affinity ligand for identification of the putative compound target. Towards this end, the starting WG extract (prior to programming with RABV mRNA or use in the cfps screen), was applied to columns of resin 1 or 2, with similar wash and elution steps as described above. The free compound eluate was subjected to exhaustive dialysis to remove both free and bound compound. A flow through extract was prepared (termed depleted extract because it is missing resin conjugate bound proteins), along with an exhaustively dialyzed free compound (A) eluate. The cfps programmed with RABV N was carried out separately in: i) the starting WG extract, ii) the resin column 1 flow through extract (depleted WG) and iii) the dialyzed eluate added to the depleted WG. These three translation reactions were carried out in the absence of compound (with DMSO vehicle control) and in the presence of a titration of two active anti-RABV pharmacophores, including A. As shown previously (see FIGS. 7 and 8), strong titration of RFUs was observed when RABV N, M, and P are translated in starting WG in the presence of A. If the target had bound to the 1 resin and therefore was missing from the flow through, no compound sensitivity should be observed upon translation of RABV N in the flow through. Fulfilling this prediction, flow through extract from the column 1 shows a striking loss of compound effect (FIGS. 12B and C, middle panel). Also as predicted, translation in the reconstituted extract comprising target-depleted flow through complemented with dialyzed eluate (containing the target), resulted in full reconstitution of dose-dependent compound titration of RFUs (FIGS. 12B and C, right panel). This functional reconstitution of drug sensitivity argues strongly that the eluate, comprised exclusively of proteins from the WG extract and prepared before the extract was programmed with RABV mRNAs, contains the target of A. Furthermore, it appears that both compounds, despite representing distinct chemotypes, act on the same target, since the extract depleted of the A target shows no dose-dependent titration with J and the 1 resin conjugate eluate restores sensitivity to J.

Effect of A on Assembly Intermediates and their Binding to Column 1

Another approach to corroboration of the mechanism of action of A is to assess the effect of the compound on assembly of newly synthesized RABV N and P by cfps as judged by ssg. As shown in FIG. 13, when newly synthesized RABV NR, M, P are treated with DMSO or A then released from the ribosome with puromycin, supplemented with brpmis and incubated at 34° C./1 h, assembly is observed in the DMSO-treated sample and significantly blocked in the A treated sample (center panels). Interestingly, the effect of the compound on assembly is strikingly enhanced when the products are assessed by affinity chromatography on column 1 resin (FIG. 13, top and bottom panels). This finding has two implications. First, from the DMSO control part of the experiment, it reveals that the target of A either leaves the assembly intermediates or more likely, the A binding site changes its accessibility from one intermediate to another. Moreover suggests that A is likely not directed to the substrate-binding site, but rather to an allosteric site of the target because binding to the column 1 does not displace the radiolabelled RABV N and P substrates. Meanwhile the results from the A-treated portion of the experiment reveal that many of the complexes formed in the presence of A are off-pathway or otherwise aberrant, as evidenced by the dramatic diminution of binding to column 1 (compare top and bottom left hand N panels). This diminution of binding cannot be accounted for by competition of free A for the resin conjugate for three reasons. First, the concentration of compound on the resin is extremely high as evidenced by the difficulty in elution with free compound (requiring multiple eluate volume additions to remove all bound compound). Second, because the behavior of assembly intermediate in fraction 1 is dramatically different from that of assembly intermediate in fraction 4, for example.

Analysis of the Column 1 Compound-Specific Eluate

Analysis of the 1 eluate revealed a striking pattern of approximately a dozen major protein bands by silver stain that were not found in the column 2 eluate (FIG. 14A). Since brpmis was able to stimulate progression to ssg fractions 5-7 (see FIG. 3D), we predicted that brpmis would produce a similar pattern of proteins upon elution of column 1, but not of column 2, to which brpmis had been applied, with free A. This was confirmed by silver stain of the brpmis free drug eluate (FIG. 14B). For both WG and brpmis, the free compound eluate from column 1 revealed 68 kDa ABCE1 by WB (FIGS. 14C and 14D) Thus, despite the heterologous nature of the starting extracts (WG versus brain), similar proteins with similar characteristics are observed binding to immobilized A, an active anti-RABV compound, and specifically eluted with free compound. Moreover, the set of proteins bound to 1 resin from both WG and brpmis includes ABCE1 (FIGS. 14C and D), a protein shown in FIG. 6 to be co-associated with RABV N and P containing complexes and previously identified in the capsid assembly pathway of a different viral family (Retroviridae) (Zimmerman C, et al. (2002) Identification of a host protein essential for assembly of immature HIV-1 capsids. *Nature* 415:88-92).

Column 1 Eluate is a Multi-protein Complex

We were initially surprised to see such a large number of distinct proteins specifically bound to the active compound conjugate (resin 1) and eluted with free A from the column 1 but not from the control column (resin 2). To better understand the meaning of this result, the WG and brpmis starting material and A eluate from column 1 were analyzed by glycerol gradient ultracentrifugation, and the gradient profiles probed by silver stain to assess the entire set of proteins observed in FIGS. 14A and B, and by WB for the presence of ABCE1. The distinctive set of proteins is found to largely migrate together on glycerol gradients (for WG shown in FIG. 15A) and include ABCE1 (for brpmis shown in FIG. 15C, WG not shown). It is interesting to observe that the complex of proteins appears to be disassembling during the 4 hrs ultracentrifugation run: the ABCE1 blot of the 1 eluate (FIG. 15C) reveals the protein present but distributed throughout the gradient in a fashion distinct from what was observed in the starting material. While some of this difference surely represents heterogeneity of ABCE1, it is likely also to be a reflection of the fact that this novel drug target is exquisitely labile when purified. Thus, while all major proteins comprising the eluate are represented at the leading edge (see silver stain of fractions 8-10 in FIG. 15A), different subsets of those proteins appear to be released into the gradient over the course of the run.

These results suggest that the eluted proteins from the compound resin conjugate 1 likely comprise a multiprotein complex that is both functional for RABV N assembly, is the basis for compound sensitivity of assembly (FIG. 12), and includes ABCE1. FIG. 16 provides a rough schematic of the relevance of these conclusions.

Discussion

The goal of the present study was to explore the possibility that cfps could identify novel, unconventional but druggable host protein targets that catalyze the progression of RABV N through assembly intermediates, based on the successful reconstitution of capsid assembly pathways with these characteristics for other viral families (Lingappa J-R, et al. (1994) A eukaryotic cytosolic chaperonin is associated with a high molecular weight intermediate in the assembly of hepatitis B virus capsid, a multimeric particle. *J Cell Biol* 125:99-111; Lingappa J-R, Hill R-L, Wong M-L, Hegde R-S (1997) A multistep, ATP-dependent pathway for assembly of human immunodeficiency virus capsids in a cell-free system. *J Cell Biol* 136:567-581; Klein K-C, Dellos S-R, Lingappa J-R (2005) Identification of residues in the hepatitis C virus core protein that are critical for capsid assembly in a cell-free system. *J Virol.* 79:6814-6826; Klein K-C, Polyak S-J, Lingappa J-R (2004) Unique features of hepatitis C virus capsid formation revealed by de novo cell-free assembly. *J Virol.* 78:9257-9269). Corroboration of authenticity of RABV capsid formation (e.g. through electron microscopy, as done previously [Lingappa J-R, et al. (1994) A eukaryotic cytosolic chaperonin is associated with a high molecular weight intermediate in the assembly of hepatitis B virus capsid, a multimeric particle. *J Cell Biol* 125:99-111; Lingappa J-R, Hill R-L, Wong M-L, Hegde R-S (1997) A multistep, ATP-dependent pathway for assembly of human immunodeficiency virus capsids in a cell-free system. *J Cell Biol* 136:567-581; Klein K-C, Dellos S-R, Lingappa J-R (2005) Identification of residues in the hepatitis C virus core protein that are critical for capsid assembly in a cell-free system. *J Virol.* 79:6814-6826]), was not pursued in the present studies. Instead, we chose validation against infectious RABV of the compounds emerging from a RABV-specific screen of this pathway. That success provides emphatic support for the proposition that the protein-protein interactions disrupted by A are relevant for RABV, presumably because of the power of i) the new paradigm of host-catalyzed capsid formation, ii) heterologous cfps as an analytical tool, and iii) these highly unconventional and labile multiprotein complexes as druggable antiviral targets.

Two observations are particularly worthy of mention. First, the active anti-RABV compound chosen for focus, A, works extremely early in the capsid assembly process, specifically while the chain is still on the ribosome. A working hypothesis outlined at the outset was that interfering with early events in protein biogenesis might have a substantial yet substrate-selective impact on later events. This notion, while conventionally counterintuitive, is strongly supported by these studies: the consequence of this very early alteration in protein-protein interactions manifests much later in the viral lifecycle as substantial reduction in infectivity of RABV.

A second fundamental observation from this study is that the protein set bound to the compound resin conjugate and specifically eluted by free compound, comprises a labile and functional multiprotein complex (based on the reconstitution demonstrated in FIGS. 12B and C). Had we approached drug discovery more conventionally, attempting to purify the target first and then using the isolated protein(s) to screen for small molecule inhibitors, it is likely this complex would have fully disintegrated and this class of compounds would not have been identified. Using a functional whole pathway screen as a means of identifying an active compound first, and subsequently applying that compound as a tool for biochemical dissection as an affinity ligand, was likely critical to arriving at these conclusions.

It is provocative that ABCE1, a protein implicated in HIV capsid assembly, should also be identified as a component of the host protein complex implicated in RABV capsid assembly. We note that ABCE1 itself is extremely heterogeneous, and only a small portion of the total ABCE1 was observed to be depleted from the extract despite the use of excess drug resin. This suggests that only a small subset of the ABCE1 present is in a conformation or assembly configuration relevant for RABV capsid formation. Presumably the other forms do other things for the host and, by corollary, may be taken advantage of by other families of viruses. This suggests the intriguing possibility that the putative assembly machines are both numerous and highly heterogeneous or highly adaptable to the multiprotein complexes they are called upon to assemble, or both.

It is also notable that the compounds shown here have activity against other viral families. However, the SAR profile for different viruses on which any given compound is active is quite different. Thus, while A is also active against FLUV, a member of family Orthomyxoviridae, analog F, which is even more potent against infectious RABV (see FIG. 7), has little activity against FLUV (Petsch et al, manuscript in preparation). Elsewhere we will demonstrate that, with SAR optimization, it is possible to advance compounds that have activity on multiple families in such a fashion that distinct subpharmacophores can be identified that have >10× greater potency against one viral family compared to others. Presumably a complex interplay of host and virus determines the relative efficacy of different lead series analogs for any given virus family. To the extent that the family of compounds defined by SAR can be used in the manner described as affinity ligands it may be possible to use the compounds and their targets to achieve a roadmap of novel host-virus interactions, as a further refinement of this approach for drug discovery.

The evidence for transient and energy-dependent action of host proteins suggests a role for an enzymatic host-derived assembly machine. If its action were blocked or altered, one can envision two classes of phenotypes: the viral particle might either be sufficiently malformed or blocked in its formation so as to not be released at all, or might be released but with a sufficiently aberrant capsid structure as to be rendered non-infectious. Elsewhere we will demonstrate both of these phenotypes for compounds with similar targets in the case of members of another viral family, the Toga-viridae (Kelley-Clarke et al submitted).

Finally, data from co-immunoprecipitation (FIG. 6) and column chromatography of radiolabelled assembly intermediates (FIG. 13) reveal significant changes in accessibility of RABV N, P and of their association with ABCE1, from one intermediate to the next. These observations suggest that the multiprotein complex changes the nature of its engagement with RABV N and P during progression from early to late assembly intermediates, as would be expected of an assembly machine commandeered by the virus for its capsid formation. Given the conservation of capsid structure across members of a viral family (Luo M, Green T-J, Zhang X, Tsao J, Qiu S (2007) Conserved characteristics of the rhabdovirus nucleoprotein *Virus Res* 129:246-251), compounds such as A may represent a powerful new approach to anti-viral therapeutics.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

```

What is claimed is:

1. A method for assaying a candidate compound for its ability to interfere with the function of a multiprotein assembly implicated in rabies, wherein said multiprotein assembly participates in folding of a protein which is rabies matrix protein and/or rabies phosphoprotein, formation of multiprotein structures comprising said protein which is rabies matrix protein and/or rabies phosphoprotein, or a combination thereof said method comprising:
   (a) providing a cell-free translation system comprising a ribosome, translating an m-RNA sequence encoding a rabies nucleoprotein substrate of said multiprotein assembly, wherein said m-RNA sequence is a truncated m-RNA sequence lacking a stop codon at its 3'-terminus such that, upon completion of translation of said m-RNA sequence, said rabies nucleoprotein substrate is complexed to said ribosome at a first site accessible to an A site, and said rabies nucleoprotein substrate is not complexed to a t-RNA;
   (b) providing conditions wherein said protein which is rabies matrix protein and/or rabies phosphoprotein is expressed in said cell-free translation system;
   (c) contacting said cell-free system with said candidate compound; and
   (d) determining whether said multiprotein assembly is bound to said rabies nucleoprotein substrate,
      wherein failure of said rabies nucleoprotein substrate to bind to said multiprotein assembly confirms said ability to interfere with the function of said multiprotein assembly of said candidate compound.

2. The method according to claim 1, wherein the candidate compound interferes with a single protein binding site, an interface between two proteins or an interface between three proteins of said multiprotein assembly.

3. The method according to claim 1, wherein the candidate compound interferes by binding to a protein active site of a single protein, protein active sites of two proteins or protein active sites of three proteins of said multiprotein assembly.

4. The method according to claim 1, wherein the candidate compound interferes by binding to an allosteric site of a single protein, an allosteric site of each of two proteins or an allosteric site of each of three proteins of said multiprotein assembly.

5. The method according to claim 1, wherein said cell-free translation system is a wheat germ system.

6. The method according to claim 5, wherein wheat germ extract is present in said system in an amount of not more than about 5%.

7. The method according to claim 1, wherein said protein which is rabies matrix protein and/or rabies phosphoprotein comprises a detectable label.

8. The method according to claim 7, wherein said detectable label is $^{35}$S-methionine.

9. The method according to claim 1, wherein said determining comprises confirming whether a rabies viral capsid was assembled.

10. The method according to claim 1, wherein following step (b), said m-RNA remains complexed to said ribosome.

11. The method according to claim 1, further comprising, contacting said cell-free translation system with puromycin, releasing said rabies nucleoprotein substrate.

12. A method of verifying that a target for a candidate compound which interferes with the function of a multiprotein assembly implicated in rabies is a host target, wherein said multiprotein assembly participates in folding of a protein which is rabies matrix protein and/or rabies phosphoprotein, formation of multiprotein structures comprising said protein which is rabies matrix protein and/or rabies phosphoprotein, or a combination thereof said method comprising:
   (a) contacting an initial medium for a cell-free translation system comprising one or more host protein with an affinity chromatography device comprising said candidate compound immobilized thereon, directly or through a linker, under conditions appropriate to bind at least one member of said multiprotein assembly to said candidate compound;
   (b) washing the device with a first eluent, removing species not bound to said candidate compound in a flow through fraction;
   (c) washing the device with a second eluent, removing the at least one member of said multiprotein assembly bound to said device in an eluent fraction;
   (d) combining said candidate compound with said flow through fraction and using the resulting first mixture for cell-free translation of an m-RNA sequence encoding a rabies nucleoprotein substrate of said multiprotein assembly, wherein said m-RNA sequence is a truncated m-RNA sequence lacking a stop codon at its 3'-terminus such that, upon completion of translation of said m-RNA sequence, said rabies nucleoprotein substrate is complexed to said ribosome at a first site accessible to an A site, and said rabies nucleoprotein substrate is not complexed to a t-RNA;
   (e) expressing said protein which is rabies matrix protein and/or rabies phosphoprotein in said cell-free translation system;
   (f) determining whether said protein which is rabies matrix protein and/or rabies phosphoprotein was folded, said multiprotein structure comprising said protein which is rabies matrix protein and/or rabies phosphoprotein was formed or both; and
   optionally,
      (i) combining said candidate compound, said flow through fraction and said eluent fraction and using the resulting second mixture for cell-free translation of said m-RNA sequence encoding said rabies nucleoprotein substrate of said multiprotein assembly, wherein said m-RNA sequence is said truncated m-RNA sequence lacking a stop codon at its 3'-terminus such that, upon completion of translation of said m-RNA sequence, said rabies nucleoprotein substrate is complexed to said ribosome at a first site accessible to an A site, and said rabies nucleoprotein substrate is not complexed to a t-RNA;

(ii) expressing said protein which is rabies matrix protein and/or rabies phosphoprotein in said second mixture;

(ii) determining whether said protein which is rabies matrix protein and/or rabies phosphoprotein was folded, said multiprotein structure comprising said protein which is rabies matrix protein and/or rabies phosphoprotein was formed or both, wherein lack of said folding of said protein which is rabies matrix protein and/or rabies phosphoprotein or formation of said multiprotein structure comprising said protein which is rabies matrix protein and/or rabies phosphoprotein confirms that said initial medium does not include a host target for said candidate compound or the host target for the candidate compound is removed by said contacting with said immobilized candidate compound, and confirmation of said folding of said protein which is rabies matrix protein and/or rabies phosphoprotein or formation of said multiprotein structure comprising said protein which is rabies matrix protein and/or rabies phosphoprotein confirms that said host target for said candidate compound is removed by said contacting with said immobilized candidate compound.

13. The method according to claim 12, wherein said multiprotein structure is a rabies viral capsid.

* * * * *

                            SEQUENCE LISTING

<160> NUMBER OF SEQ ID NOS: 6

<210> SEQ ID NO 1
    <211> LENGTH: 27
    <212> TYPE: PRT
    <213> ORGANISM: Artificial Sequence
    <220> FEATURE:
    <223> OTHER INFORMATION: peptide epitope of RABV N
    <220> FEATURE:
    <221> NAME/KEY: MOD_RES
    <222> LOCATION: (1)..(1)
    <223> OTHER INFORMATION: ACETYLATION
    <220> FEATURE:
    <221> NAME/KEY: MOD_RES
    <222> LOCATION: (27)..(27)
    <223> OTHER INFORMATION: AMIDATION

<400> SEQUENCE: 1

Cys Phe Phe Arg Asp Glu Lys Glu Leu Gln Glu Tyr Glu Ala Ala Glu
    1               5                   10                  15

Leu Thr Lys Thr Asp Val Ala Leu Ala Asp Asp
                20                  25

<210> SEQ ID NO 2
    <211> LENGTH: 1350
    <212> TYPE: DNA
    <213> ORGANISM: Artificial Sequence
    <220> FEATURE:
    <223> OTHER INFORMATION: Rabies nucleoprotein with termination codon
          removed

<400> SEQUENCE: 2
atggatgccg acaagattgt attcaaagtc aataatcagg tggtctcttt gaagcctgag      60
attatcgtgg atcaatatga gtacaagtac cctgccatca agatttgaa aaagccctgt     120 ataaccctag gaaaggctcc cgatttaaat aaagcataca agtcagtttt gtcaggcatg     180
agcgccgcca aacttaatcc tgacgatgta tgttcctatt tggcagcggc aatgcagttt     240
tttgagggga catgtccgga agactggacc agctatggaa ttgtgattgc acgaaaagga     300
gataagatca ccccaggttc tctggtggag ataaaacgta ctgatgtaga agggaattgg     360
gctctgacag gaggcatgga actgacaaga gaccccactg tccctgagca tgcgtcctta     420
gtcggtcttc tcttgagtct gtataggttg agcaaaatat ccgggcaaaa cactggtaac     480
tataagacaa acattgcaga caggatagag cagattttttg agacagcccc ttttgttaaa     540
atcgtggaac accatactct aatgacaact cacaaaatgt gtgctaattg gagtactata     600
```

```
ccaaacttca gattttttggc cggaacctat gacatgtttt tctcccggat tgagcatcta    660
tattcagcaa tcagagtggg cacagttgtc actgcttatg aagactgttc aggactggta    720
tcatttactg ggttcataaa acaaatcaat ctcaccgcta gagaggcaat actatatttc    780
ttccacaaga actttgagga agagataaga agaatgtttg agccagggca ggagacagct    840
gttcctcact cttatttcat ccacttccgt tcactaggct tgagtgggaa atctccttat    900
tcatcaaatg ctgttggtca cgtgttcaat ctcattcact ttgtaggatg ctatatgggt    960
caagtcagat ccctaaatgc aacggttatt gctgcatgtg ctcctcatga aatgtctgtt   1020 ctaggggggct atctgggaga ggaattcttc gggaaaggga catttgaaag aagattcttc   1080
agagatgaga aagaacttca agaatacgag gcggctgaac tgacaaagac tgacgtagca   1140
ctggcagatg atggaactgt caactctgac gacgaggact acttttcagg tgaaaccaga   1200
agtccggagg ctgtttatac tcgaatcatg atgaatggag gtcgactaaa gagatctcac   1260
atacggagat atgtctcagt cagttccaat catcaagccc gtccaaactc attcgccgag   1320
tttctaaaca agacatattc gagtgactca                                     1350
```

<210> SEQ ID NO 3
<211> LENGTH: 1350
<212> TYPE: RNA
<213> ORGANISM: Artificial Sequence
<220> FEATURE:
<223> OTHER INFORMATION: mRNA encoding of Rabies nucleprotein without termination codon

<400> SEQUENCE: 3

```
auggaugccg acaagauugu auucaaaguc aauaaucagg uggucucuuu gaagccugag     60
auuaucgugg aucaauauga guacaaguac ccugccauca aagauuugaa aaagcccugu    120
auaacccuag aaaggcucc cgauuuaaau aaagcauaca agucaguuuu gucaggcaug    180
agcgccgcca aacuuaaucc ugacgaugua uguuccuauu uggcagcggc aaugcaguuu    240
uuugagggga caugaccgga agacuggacc agcuauggaa uugugauugc acgaaaagga    300
gauaagauca ccccagguuc ucuggguggag auaaaacgua cugauguaga agggaauugg    360
gcucugacag gaggcaugga acugacaaga accccacug ucccugagca ugcguccuua    420
gucggucuuc ucuugagucu guauagguug agcaaaauau ccgggcaaaa cacugguaac    480
uauaagacaa acauugcaga caggauagag cagauuuuug agacagcccc uuuuguuaaa    540
aucguggaac accauacucu aaugacaacu cacaaaaugu gugcuaauug gaguacuaua    600
ccaaacuuca gauuuuuggc cggaaccuau gacauguuuu ucucccggau ugagcaucua    660
uauucagcaa ucagaguggg cacaguuguc acugcuuaug aagacuguuc aggacuggua    720
ucauuuacug gguucauaaa acaaaucaau cucaccgcua gagaggcaau acuauauuuc    780
uuccacaaga acuuugagga agagauaaga agaauguuug agccagggca ggagacagcu    840
guuccucacu cuuauuucau ccacuuccgu ucacuaggcu ugaguggaa aucuccuuau    900 ucaucaaaug cuguuggucau cguguucaau cucauucacu uuguaggaug cuauaugggu    960
caagucagau cccuaaaugc aacgguuauu gcugcaugug cuccucauga aaugucuguu   1020 cuaggggggcu aucugggaga ggaauucuuc gggaaaggga cauuugaaag aagauucuuc   1080
agagaugaga aagaacuuca agaauacgag gcggcugaac ugacaaagac ugacguagca   1140
cuggcagaug auggaacugu caacucugac gacgaggacu acuuuucagg ugaaaccaga   1200
aguccggagg cuguuuauac ucgaaucaug augaauggag gucgacuaaa gagaucucac   1260
```

```
auacggagau augucucagu caguuccaau caucaagccc guccaaacuc auucgccgag    1320
uuucuaaaca agacauauuc gagugacuca                                    1350
```

<210> SEQ ID NO 4
<211> LENGTH: 1353
<212> TYPE: RNA
<213> ORGANISM: Artificial Sequence
<220> FEATURE:
<223> OTHER INFORMATION: mRNA encoding of Rabies nucleprotein with
      termination codon

<400> SEQUENCE: 4

```
auggaug

```
<213> ORGANISM: Artificial Sequence
<220> FEATURE:
<223> OTHER INFORMATION: upstream of oligonucleotide used to amplify
      Rabies nucleoprotein without stop codon

<400> SEQUENCE: 6
ggctcgacag atcttaaggc t                                              21
```